(12) United States Patent
Kaplan et al.

(10) Patent No.: US 8,398,961 B2
(45) Date of Patent: Mar. 19, 2013

(54) POWDERY STYLING AGENTS AND THE DISPENSER SYSTEMS THEREOF

(75) Inventors: Anett (née Sälzer) Kaplan, Dusseldorf (DE); Bernd Richters, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 772 days.

(21) Appl. No.: 12/140,977

(22) Filed: Jun. 17, 2008

(65) Prior Publication Data

US 2008/0274071 A1    Nov. 6, 2008

Related U.S. Application Data

(63) Continuation of application No. PCT/EP2006/011913, filed on Dec. 11, 2006.

(30) Foreign Application Priority Data

Dec. 24, 2005 (DE) .......................... 10 2005 062 268

(51) Int. Cl.
*A61K 8/72* (2006.01)
*A61K 51/00* (2006.01)
*A61Q 5/06* (2006.01)

(52) U.S. Cl. ..................... 424/70.11; 424/1.13; 424/401

(58) Field of Classification Search .................. None
See application file for complete search history.

(56) References Cited

U.S. PATENT DOCUMENTS

| | | |
|---|---|---|
| 1,985,424 A | 12/1932 | Alfred |
| 2,016,962 A | 8/1935 | Flint |
| 2,703,798 A | 3/1955 | Schwartz |
| 3,083,917 A | 4/1963 | Abplanalp |
| 3,083,918 A | 4/1963 | Abplanalp |
| 3,320,292 A | 5/1967 | Arno et al. |
| 3,544,258 A | 12/1970 | Presant |
| 3,753,968 A | 8/1973 | Ward |
| 3,966,629 A | 6/1976 | Dumbrell |
| 4,062,647 A | 12/1977 | Storm et al. |
| 4,152,416 A | 5/1979 | Marra |
| 4,324,780 A | 4/1982 | Jacquet et al. |
| 4,393,886 A | 7/1983 | Strasilla et al. |
| 4,524,009 A | 6/1985 | Valenty |
| 4,630,954 A * | 12/1986 | Ladd, Jr. ....................... 401/123 |
| 4,639,325 A | 1/1987 | Valenty |
| 4,737,306 A | 4/1988 | Wichelhaus et al. |
| 4,814,101 A | 3/1989 | Schieferstein et al. |
| 4,816,553 A | 3/1989 | Baur et al. |
| 4,820,439 A | 4/1989 | Rieck |
| 4,865,774 A | 9/1989 | Fabry et al. |
| 4,931,218 A | 6/1990 | Schenker et al. |
| 4,985,553 A | 1/1991 | Fuertes et al. |
| 5,294,726 A | 3/1994 | Behler et al. |
| 5,312,932 A | 5/1994 | Behler et al. |
| 5,322,957 A | 6/1994 | Fabry et al. |
| 5,356,607 A | 10/1994 | Just |
| 5,484,531 A | 1/1996 | Kuehne |
| 5,494,488 A | 2/1996 | Arnoldi et al. |
| 5,501,814 A | 3/1996 | Engelskirchen et al. |
| 5,534,267 A | 7/1996 | Neunhoeffer |
| 5,541,316 A | 7/1996 | Engelskirchen et al. |
| 5,580,941 A | 12/1996 | Krause et al. |
| 5,773,595 A | 6/1998 | Weuthen |
| 5,780,420 A | 7/1998 | Breuer et al. |
| 5,821,360 A | 10/1998 | Engelskirchen et al. |
| 5,830,956 A | 11/1998 | Stockhausen et al. |
| 5,959,101 A | 9/1999 | Engelskirchen et al. |
| 6,187,055 B1 | 2/2001 | Kottwitz et al. |
| 6,235,913 B1 | 5/2001 | Raths et al. |
| 6,257,172 B1 * | 7/2001 | Leppanen ..................... 119/605 |
| 6,506,720 B1 | 1/2003 | Blasey |
| 7,008,912 B1 | 3/2006 | Rettenmaier |
| 7,217,777 B2 | 5/2007 | Lange et al. |
| 7,332,466 B2 | 2/2008 | Schmid |
| 2002/0014246 A1 | 2/2002 | Choi |
| 2003/0161675 A1 | 8/2003 | Lee |
| 2004/0262340 A1 | 12/2004 | Kress |

FOREIGN PATENT DOCUMENTS

| | | |
|---|---|---|
| DE | 3139438 A1 | 4/1983 |
| DE | 3725030 | 2/1989 |
| DE | 4204700 | 8/1993 |
| DE | 4417734 A1 | 11/1995 |
| DE | 19709991 | 9/1998 |
| DE | 19754053 A1 | 6/1999 |
| DE | 19756454 C1 | 6/1999 |
| DE | 10312270 A1 | 9/2004 |
| DE | 202004015369 U1 | 12/2004 |
| EP | 0026529 | 4/1981 |
| EP | 0028432 | 5/1981 |
| EP | 47714 | 3/1982 |
| EP | 0150930 | 8/1985 |
| EP | 217274 | 4/1987 |
| EP | 283817 | 9/1988 |
| EP | 0427349 | 5/1991 |
| EP | 466986 | 1/1992 |
| EP | 0472042 | 2/1992 |
| EP | 0542496 | 5/1993 |
| EP | 0561825 | 9/1993 |
| EP | 0561999 | 9/1993 |
| EP | 0690044 | 1/1996 |
| EP | 0740741 | 11/1996 |

(Continued)

OTHER PUBLICATIONS

DE 10312270, Machine tanslation, retrieved on Aug. 31, 2010, EPO databse, p. 1-15.*

(Continued)

*Primary Examiner* — Ernst Arnold
(74) *Attorney, Agent, or Firm* — David LeCroy

(57) ABSTRACT

The present invention relates to agents for the setting and styling of keratin fibers, in particular human hair, from a suitable dispenser system in the form of a fine powder, which is optionally freshly ground, shaved or rasped only directly prior to use, and to the use of this preparation for the treatment of keratin fibers, in particular human hair.

12 Claims, No Drawings

FOREIGN PATENT DOCUMENTS

| | | |
|---|---|---|
| GB | 962919 | 7/1964 |
| GB | 1473571 | 5/1977 |
| GB | 2104091 | 3/1983 |
| JP | 05339896 A | 12/1993 |
| WO | WO9108171 | 6/1991 |
| WO | WO9206984 | 4/1992 |
| WO | WO9218542 | 10/1992 |
| WO | WO9308251 | 4/1993 |
| WO | WO9316110 | 8/1993 |
| WO | WO9408970 | 4/1994 |
| WO | WO9428030 | 12/1994 |
| WO | WO9507303 | 3/1995 |
| WO | WO9512619 | 5/1995 |
| WO | WO9520029 | 7/1995 |
| WO | WO9520608 | 8/1995 |
| WO | WO9840462 | 9/1998 |
| WO | WO9840463 | 9/1998 |
| WO | WO9855583 | 12/1998 |
| WO | WO9855590 | 12/1998 |
| WO | WO0210257 | 2/2002 |

OTHER PUBLICATIONS

International Cosmetic Ingredient Dictionary and Handbook 7$^{th}$ ed. (1997), The Cosmetic Toiletry and Fragrance Association 1101 17$^{th}$ Street N.W., Suite 300, Washington, DC 20036-4702.

Encyclopedia of Polymer Science and Engineering, vol. 15, Second Edition, Seiten 204, bis 308, John Wiley & Sons, Inc. 1989.

Falbe (ed.) Surfactants in Consumer in Consumer Products, Springer Verlag, Berlin 1987, S. 54-124.

Biswas, A.K. et al., "Surface-Active Properties of Sodium Salts of Sulfated Fatty Acid Monoglycerides," in J. Am Oil. Chem. Soc., vol. 37, (Apr. 1960).

F.U. Ahmed, "Efficient Synthesis of Fatty Monoglyceride Sulfates from Fatty Acids and Fatty Acid Methyl Esters," in J. Oil. Chem. Soc., vol. 67, No. 8, (Jan. 1990).

Biermann et al. in Starch/Stäke, vol. 45, No. 8, p. 281-288 (1993).

B. Salka in Cosm. Toil. 108, (1993) p. 89-94.

J. Kahre et al. in SÖFW-Journal, Issue 8, p. 598-611 (1995).

H. Kelkenberg in Tenside Surfactant Detergents 25, (1988), p. 8-13.

Arctander, S., Perfume and Flavor Chemicals vols. I and II, self-published Montclair, NJ (1969).

Bauer, K. et al., Common Fragrance and Flavor Materials, 3$^{rd}$ Ed. Wiley-VCH Weinheim (1997).

Römp-Lexikon. Chemie. George Thieme Verlag, 10th Edition, 1997, pp. 1764.

Voight, R. Textbook of Pharmaceutical Technology. VCH, 6th Edition, 1997, pp. 182-184.

Dörfler, H.D. Grenzflachen-und Kolloidchemie, VCH Verlagsgesellschaft mbH, 1994.

Domsch, Andreas. Cosmetic Preparations: vol. II: Aqueous and surfactant-containing formulations. Verlag für chemische Industrie, 1994, pp. 259-293.

Engel, W. et al., "Characteristics of a Buffering Shampoo Containing Sericin," Arztichen Kosmetologie, 17, 1987, pp. 91-110.

Römp Chemical Encyclopedia, T-Z. George Thieme Verlag, vol. 6, 9th Edition, pp. 4440.

Beyer, Hans et al., Textbook of Organic Chemistry, S. Hirzel Verlag Stuggart, 19th Edition, 1981, pp. 393-433.

\* cited by examiner

POWDERY STYLING AGENTS AND THE DISPENSER SYSTEMS THEREOF

CROSS-REFERENCE TO RELATED APPLICATIONS

This application is a continuation under 35 U.S.C. Section 365(c) and 35 U.S.C. Section 120 of International Application No. PCT/EP2006/011913, filed Dec. 11, 2006. This application also claims priority under 35 U.S.C. Section 119 of German Patent Application No. DE 10 2005 062 268.2, filed Dec. 24, 2005. Both the International Application and the German Application are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

(1) Field of the Invention

The present invention relates to agents for the setting and styling of keratin fibers, in particular human hair, from a suitable dispenser system in the form of a fine powder, which is optionally freshly ground, shaved or rasped only directly prior to use, and to the use of this preparation for the treatment of keratin fibers, in particular human hair.

Cosmetic agents for the care and retention of the natural functions of skin and hair are becoming more and more important. Changed consumer practices and fashion trends, inter alia, contribute to this. Thus, for example, as a result of the intense use of sun studios, skin and hair are becoming more permanently damaged by UV light. This damage is evident on the skin and on the hair, for example, from a loss in elasticity.

A nice-looking hairstyle is nowadays generally regarded as an indispensable part of a cared-for appearance. In this connection, on account of current fashion trends, hairstyles regarded as chic are time and again those which, for many hair types, can only be created and/or maintained for a relatively long period up to several days using setting active ingredients.

Keratin fibers, in particular human hair, are nowadays subjected to a large number of treatments. In this connection, treatments which serve to permanently or temporarily shape the hair play an important role. Temporary shapings, which are intended to provide good hold without adversely affecting the healthy appearance of the hair, such as, for example, its shine, can be achieved, for example, through hairsprays, hair waxes, blow-waves etc.

Usually, hairsprays, pump spray setting compositions, hair gels or hair waxes are offered as single-phase products in opaque packagings. However, it has recently been found that besides placing demands on the hold and the care, the consumer is placing ever greater demands on the design and the ease of handling of the products, meaning that products are now increasingly being manufactured in transparent packagings which make it easier for the consumer to recognize the contents and give the products greater attractiveness.

It is, however, also the object to develop corresponding agents which satisfy the expectations of the consumer with regard to the application properties, for example the hold, fullness, the possibility of shaping hairstyles and the drying time in the case of setting hair care agents, and can easily be portioned, which are simply and easily packaged so that they can be taken along anywhere at any time and can thus be used anywhere anytime or are already publicly available anytime at any desired sites.

Thus, in the past, for example, aqueous-based agents have replaced agents based on volatile organic compounds. Here, the problem of the lower volatility of water compared to the alcohols arose, which resulted in longer drying times on the hair. Furthermore, on account of the often poorer solubility of polymeric compounds in aqueous systems, this switch is also often associated with the disadvantage that upon applying the desired amount of polymer to the hair, water automatically reaches the hair in amounts such that the drying times become unacceptably long. These problems also result in considerable deviations in the dosing of the agents by the consumer. A further demand by the consumer for an ecological alternative to hair care agents with a setting effect in the form of foams or sprays is also still not satisfied to an adequate degree with agents based predominantly on water as solvent.

Further hair care products for creating hairstyles are hair waxes. Hair waxes generally comprise, as shaping component, vegetable, animal or mineral waxes, and also synthetic polymers and are supplied as solid formulations, mostly in small pots. To use, a certain amount is removed from the pot, then rubbed in the hand and distributed on the hair. These hair waxes bring about, on the basis of natural raw materials, good hold of the hair at the same time as providing high shine. Nevertheless, the hair waxes on the market still do not completely satisfy the wishes of the consumer with regard to simple application and ease of distribution on the hair. Thus, here too, precise, simple and consistently reproducible dosing is a problem. Either too much or too little product is often removed from the customary pots and tubes or, particularly from the tubes, the squeezing of a strand often leads to product losses as a result of contamination with the immediate surroundings. A further problem which should not be underestimated is microbiological contamination by the user.

It was therefore also the object to develop easy-to-handle, exactly dosable packaged amounts of cosmetic agents each sufficient for one application.

The setting active ingredients, which are generally polymeric compounds, can be incorporated into customary hair cleansers or conditioners. In many cases, however, it is advantageous to apply them in the form of special agents such as hair-setting agents, hair gels, hair waxes or hairsprays.

Setting hair treatment agents are likely to be applied several times in the day. Here, the corresponding hair treatment agent is often carried by the consumer always ready to hand. In this connection, however, the large volume of customary aerosol cans is a severe disadvantage. Although the aerosol cans could be reduced in volume, for example to cans with a content of 100 ml or 50 ml, the contents would then only suffice for a few applications. This is not acceptable for the consumer and additionally increases the amount of waste. Compact hairsprays, which have been commercially available for some time, do not present a satisfactory solution either. In the formulations, the largest part is solvent and propellant gas. Both are a burden on the environment.

Hair treatment agents which give the hair more volume and hold are known. The cosmetic polymers usually used for this purpose exhibit good setting properties in aqueous, aqueous-alcoholic or alcoholic solutions, which, following application, shape and set the hair more or less well and which can additionally also give the hair more volume. However, this effect often does not last long and even upon combing the hair through, the desired volume effect is partially lost again. Many of the setting or volumizing polymers often have undesired side effects which are evident from the fact that the treated hair has too rough a feel, is too heavily weighed down or has unsatisfactory elasticity, or too many visible residues form on the hair. Inadequate ability of these hair treatment agents to be washed out following application may also be a problem.

However, the cause of irritation to the skin, nails or the hair is often not the cosmetic agent per se, but more likely individual ingredients of the particular compositions. This is the case very particularly frequently for the preservatives present in the cosmetic agents. During the manufacture and packaging of the cosmetic agents, even though all of the precautions on the part of the manufacturer of the agents for a germ-free production can be met, the cosmetic agent in question is generally contaminated with germs at the latest by the consumer while using said pack, which often lasts weeks. For a long time, on the part of the consumer there has therefore been the hitherto virtually unsatisfied wish for preservative-free cosmetic preparations.

The setting active ingredients, which are generally polymeric compounds, can be incorporated into customary hair cleansers or conditioners. However, in many cases it is advantageous to apply them in the form of special agents such as hair-setting agents, hair gels, hair waxes or hairsprays.

Hairsprays usually comprise synthetic polymers as shaping component. Preparations which comprise a dissolved or dispersed polymer can be applied to the hair by means of propellant gases or by a pump mechanism.

Polymeric compounds are used widely and with increasing importance in cosmetic agents. They have numerous functions and effects, are often themselves multifunctional and in a single structure exhibit equally several desired effects for the cosmetic agent in question. Thus, polymers can be used to adjust cosmetic agents in a targeted manner to the desired rheological properties. For example, they can bind water and, as a result, build up viscosity. At the same time, however, bound water in cosmetic agents also means a reduction in water activity, which may be important for the build-up of germs in the agent in question. If the activity of the free water is too low, then no more germs can dissolve and develop therein. The agent in question then does not have to be preserved at all or only has to be preserved to a significantly lesser degree. In this connection, multifunctional means that the use of one polymeric raw material fulfills several functions at the same time.

There have been many attempts to further develop and optimize the hair-setting agents. Thus, in the past, for example, aqueous-based agents have replaced agents based on volatile organic compounds. Here, the problem of the lower volatility of water compared to the alcohols arose, which resulted in longer drying times on the hair. Furthermore, on account of the often poorer solubility of polymeric compounds in aqueous systems, this switch is also often associated with the disadvantage that upon applying the desired amount of polymer to the hair, water automatically reaches the hair in amounts such that the drying times become unacceptably long. These problems also result in considerable deviations in the dosing of the agents by the consumer. A further demand by the consumer for an ecological alternative to hair care agents with a setting effect in the form of foams or sprays is also still not satisfied to an adequate degree with agents based predominantly on water as solvent.

There has recently been a series of developments in the cosmetics field which have created a need for new types of active ingredients or active ingredient combinations, novel formulation forms or novel administration forms. Many of these developments are here not based exclusively on application disadvantages or shortcomings of the known agents, but, for example, on environmental protection considerations, legal stipulations or other "nontechnical" reasons. In particular, the changed way of life of consumers leads to the consumer of a cosmetic agent nowadays expecting a simple, uniform and good dosing and also rapid application of the products that is possible at any time.

Setting hair treatment agents are likely to be applied several times in the day. Here, the corresponding hair treatment agent is often carried by the consumer always ready to hand. In this connection, however, the large volume of customary aerosol cans is a severe disadvantage. Although the aerosol cans could be reduced in volume, for example to cans containing 100 ml or 50 ml, the contents would then only suffice for a few applications. This is not acceptable for the consumer and additionally increases the amount of waste. Even highly concentrated, at least two to five-times as highly concentrated hairspray formulations based on the content of setting polymers were unable to provide remedy.

On the other hand, products in solid form, which are dissolved in water directly prior to actual use, have hitherto found no acceptance by the consumer. This may lie in the inadequate dosing possibility because, for example in the case of tablets, only a whole styling tablet or at best half a tablet can be dissolved in the hand with a little water. Compositions that are powdery, flowable or can be rubbed off from a block in a suitable dispenser system could provide remedy here.

BRIEF SUMMARY OF THE INVENTION

It is therefore furthermore the object to develop corresponding highly concentrated agents which satisfy the expectations of the consumer with regard to the application properties, for example the long-lasting hold of the hairstyle, in particular a long-lasting (up to days) high volume, fullness, ease of combability of the wet and dry hair to shape the hairstyles, in particular in the area of the hair ends, the shine, the velvety, supple feel of the hair, the possibility of shaping hairstyles and a short drying time in the case of setting hair care agents, and also the flexibility of the shaped hairstyle and the ability of the compositions to be washed out. Additionally, the consumer desires low packaging which can be comfortably transported and thus available everywhere. A system which were publicly accessible as a service, for example like soap dispensers in toilets, would likewise be advantageous for the consumer. Despite the desired low packaging, however, the contents should suffice for numerous applications and correspond to or exceed the number of applications of a standard commercial hairspray.

It has now been found that the object is achieved by a setting hair treatment agent in solid form which has:
at least 1.0% by weight of at least one film-forming and/or setting polymer,
at least 0.1% by weight of a dissolution accelerator and furthermore is characterized in that the composition is in the form of a solid, in particular powder or granules or a solid block,
and the hair treatment agent is applied with the help of a dispenser system.

The present invention also encompasses more or less spherical shaped bodies of several millimeters in diameter which are ground or grated to give a powder only directly prior to use. All of the compositions of this type are wetted here as finely divided powder either in the hand or after applying the powder to the hair with a little water. Subsequently, these preparations are used to style, construct and/or set the hairstyle as usual.

Compared with the prior art, the method has the major advantage that there is only one composition for all different degrees of setting. The amount regulates whether the setting should be slight or range to strong setting. It is a further advantage that, where appropriate, no setting products of any kind have to be taken along on the part of the consumer.

Concepts of this type have hitherto been neither commercially available, nor described in the literature. They can be translated, for example, into one of the following embodiments:

Embodiments of the Dispenser System.

In a first embodiment according to the invention, the dispenser system comprises a container provided with a grinder. The compositions are added in block form to the storage section of the dispenser container. The measurements in the three spatial dimensions and in the diameter in the case of elliptical or spherical cross sections of the receiving container for the block with the composition according to the invention are from 0.5 cm to 25 cm. The entire system can be mounted, for example, in toilets. As in the case of known soap dispensers, which are filled with solid soap bars from which, by means of a grater, a certain amount is rasped off prior to use, so too can these setting solid compositions be stored in such graters in order to be available at any time to the consumer at any opportunity. The solid block of the composition according to the invention can here assume all shapes and geometries. This is restricted by the shape of the storage container above the grinder.

Furthermore, the presentation form can be varied through the choice of grinder type. Similarly to kitchen equipment, a grinder with longitudinal slits serves to produce strip-shaped products. Choosing different rasp-like grinders makes it possible to dispense product powder in varying degrees of fineness. Within the context of the invention, it is conceivable to make available to the end user of the dispenser system various grinders so that he can adjust the fineness of the product powder in a variable manner depending on the situation and desired type of styling. This adjustability can be generated either as a result of the exchangeability of the grinder or through the adjustability of the individual grinding elements relative to one another.

BRIEF DESCRIPTION OF THE SEVERAL VIEWS OF THE DRAWING(S)

Not Applicable

DETAILED DESCRIPTION OF THE INVENTION

For high users, such as, for example, hairdressing salons, electrical operation of the grinder is also conceivable. In this case, the amount of product required in each case can be freshly dispensed rapidly and without loss of time. These dispenser systems can either be designed to be stationary, for example attached to the wall, or else mobile, like electric pepper cellars.

In one variant according to the invention of this embodiment, a composition for the arranging and/or styling and/or setting of hair is formulated as a solid block. The required and desired amount of the composition can then be rubbed off from this solid block using a grater. In this connection, a container surrounding the block is not absolutely necessary. Instead, the block can also be packaged just in paper or film. A hand grater can be used as grater. According to the invention, all types of graters can be used. In this connection, the grater may, for example, have a flat or curved structure or be like a nutmeg grater. The geometric shape of the block here is arbitrary. The block according to the invention can be present in the form of a sphere, a cuboid, a tetrahedron, a cube etc.

Preferably, the packaging surrounding the block is made of a material which can also be grated and does not have an adverse effect on the desired properties of the product. Liquid-soluble packagings in particular are possible. In order to ensure that this packaging does not undesirably dissolve during storage or transportation, it is useful to configure the dissolution property in such a way that dissolution is possible only at a large surface area/volume ratio, i.e. in the grated state. It is thus advantageous to couple the dissolution property with a high volume-based surface area.

In a second embodiment, a composition for arranging and/or setting and/or styling hair is already formulated as a finished, flowable and pourable powder. The dispenser system used for such a composition can in principle be any standard commercial product from which solids can be spread as powders. For example, salt and pepper cellars, shakers for icing sugar, etc., can be used here. However, it is essential here that the size and the shape of the openings in the shaker head are matched to the size and the shape of the powder or granules. It is also possible, as with known pepper or spice shakers, for a plurality of sieve-like perforated plates tailored to the size and the shape of the powder or granules to be housed in the closure section for the vessel. The bores in the sieve plate may then be different so that different amounts of powder or granules can be removed in one shaking operation.

In such an embodiment, it is also advantageous to provide a mechanical or other device for comminuting and/or smashing undesired agglomerates in the powdery or granulated product. One possible variant is the provision of at least one flattened element which can be moved along on the inside of the openings on this. One simple variant is a rotating element with two or more scraping elements which smash or comminute agglomerates appearing at the openings until they pass through the opening. These devices are helpful if the product is stored for a prolonged period, particularly if it is a hygroscopic product.

In a third form according to the invention, a composition for arranging and/or setting and/or styling hair is formulated as a solid body with a size of a few millimeters in diameter. These shaped bodies can then be supplied in a dispenser system such as, for example, a standard commercial mill, as is also supplied for spices or salt, and be removed in freshly ground portions. The grinding of the shaped bodies can take place here mechanically by hand or with the help of a corded or cordless battery-operated grinder.

In all of the embodiments hitherto, the finely divided powder can, after it has been applied to the hair, be better distributed on the hair with the help of a paintbrush, a comb or a brush. Also, the water can be applied to the powder and the hair using a moistened paintbrush. This procedure on the one hand allows the hands not to become soiled, and on the other hand allows targeted and even application to the hair. A suitable paintbrush is in principle any paintbrush as is customarily used in connection with cosmetic applications on the skin or the hair. A glitter paintbrush is very particularly suitable. Such glitter paintbrushes have dense bristles and a relatively large, in most cases round or oval, diameter ranging from a few millimeters to 5 centimeters. However, any other external shape of the paintbrush, such as cuboid, cube, pyramid, tetrahedron etc. is also suitable according to the invention. According to the invention, the use of a corresponding brush, a brush for example as for mascara, is also suitable. The bristles of the paintbrush can be made of synthetic material or of natural material. Natural material is preferred. Natural bristles can be made of horse hair, camel hair, sheep's wool etc. Preference is given to using horse hair.

In a fourth particularly preferred embodiment, the paintbrush itself is also the dispenser system. For this, the paintbrush overall is designed so that the paintbrush handle has a cavity on the inside. This cavity contains the finely divided powder. This powder is pressed from the inside cavity into the fibers of the paintbrush with the help of a pressure mechanism, as is also used, for example, in ballpoint pens for pressing out the refill before writing. In this connection, with each press on the pushing mechanism, only a certain amount of powder is dispensed into the fiber bristles of the paintbrush. This amount is at least 0.1 g per press on the mechanism. Amounts of 0.25 g are preferred, particular preference is given to amounts of 0.5 g, and very particular preference to amounts of 1 g per press on the mechanism. According to the invention, it is also possible, depending on the type of desired setting, to provide in this embodiment corresponding paintbrushes which can also accommodate larger volumes of the powder through the choice of the dimensions of the paintbrush overall. In this case, the amount which is released per press on the trigger mechanism can very likely also be more than 1 g ranging to 25 g. Matching the desired dispensed amount and the measurements of the paintbrush does not represent a problem for the person skilled in the art.

In a fifth embodiment, the finely powdered composition is packaged in a small pot or in a hinged-lid box, as is also used, for example, for mascara or powder. In this variant there is again a standard commercial paintbrush with which the finely divided composition is removed from the container and is applied evenly with the paintbrush to the hair. All of the paintbrushes as already described previously are suitable. These paintbrushes are preferably contained directly in the pot or the hinged-lid box. For example, they are attached or inserted under the lid, above the seal.

In the last embodiment, the compositions according to the invention can be used in the form of solids sprays either in aerosol or in nonaerosol.

The compositions according to the invention can be packaged in standard commercial aerosol cans. The cans can be made of tinplate or aluminum. Furthermore, the cans can be coated on the inside in order to reduce the risk of corrosion as far as possible.

If the compositions according to the invention is used as nonaerosol spray application, no propellant gas is present. However, the spray heads are in any case to be selected according to the corresponding required spray rates.

The cans are equipped with a suitable spray head. Depending on the spray head, ejection rates, based on completely filled cans, of from 0.1 g/s to 5.0 g/s are possible. The spray rate here is determined by firstly weighing an aerosol can filled with propellant gas and the corresponding composition and sealed with the valve in question at room temperature (about 23° C.). The can including the contents is shaken vigorously by hand 10 times so that the contents are thoroughly mixed. The valve of the vertical can is then actuated for 10 s. It is then weighed again. The process is carried out 5 times in succession and the statistical average is calculated from the results. The difference in the two weighings is the spray rate per 10 s. From this, the spray rate per second can be determined by simple division. In the case of nonaerosols, the spray mechanism is correspondingly actuated 10 times. In the latter case, spray rate is to be understood as meaning the average dispensed amount per spray stroke (pump stroke). Spray rates of from 0.1 to 0.5 g/s are preferred here. Spray rates of from 0.1 to 0.4 g/s are particularly preferred.

If the compositions according to the invention are used as nonaerosol spray application, no propellant gas is present. However, the spray heads are in any case to be selected according to the corresponding required spray rates.

For the design of the invention as aerosol application, any corresponding aerosol valve can be used which permits the spray rate according to the invention and/or the corresponding droplet sizes. Here, it may be advantageous if the valve opening has a diameter of at most 0.4 mm. An opening of 0.35 mm is preferred here. Very particular preference is given to valve openings of at most 0.3 mm. Corresponding aerosol valves are described, for example, in the patent specifications U.S. Pat. Nos. 4,152,416, 3,083,917, 3,083,918, 3,544,258. Such valves can be obtained commercially, for example, from Seaquist Perfect Dispensing GmbH or Coster Technologie Speciali S.p.A. In a very particularly preferred embodiment, the valve used is the Ariane M type valve from Seaquist. In this connection, it may be particularly preferred if this valve is used together with a special choker. The choker is located here either in the stem of the valve or in the spray head. A further particularly preferred embodiment uses, as valve, a valve with side bore, as is supplied, for example, by Coster under the brand name K125 SL184/3/6.

To use the compositions according to the invention as aerosol sprays, propellant gases have to be used. The propellant gases preferred according to the invention are selected from the hydrocarbons having 3 to 5 carbon atoms, such as propane, n-butane, isobutane, n-pentane and isopentane, dimethyl ether, carbon dioxide, dinitrogen oxide, fluorocarbons and chlorofluorocarbons, and also mixtures of these substances. Very particularly preferred propellant gases are propane, butane, isobutane, pentane, isopentane, dimethyl ether and the mixtures of these aforementioned propellant gases with one another. Propellant gases most preferred according to the invention are the mixtures of dimethyl ether with hydrocarbons. Within the group of hydrocarbons, n-butane and propane are preferred as propellant gases.

According to a preferred embodiment, the preparations according to the invention comprise the specified hydrocarbons or mixtures of the specified hydrocarbons with dimethyl ether as the sole propellant. However, the invention also expressly covers the co-use of propellants of the fluorochlorocarbon type, but in particular of the fluorocarbon type.

The propellant gases are present in amounts of 5-98% by weight, preferably 10-98% by weight and particularly preferably 20-98% by weight, very particularly preferably from 40 to 98% by weight, in each case based on the total aerosol composition.

For the design of the invention as nonaerosol, any spray pump can be used which permits the spray rate according to the invention. Appropriate systems are commercially available, for example, under the name Calmar Mark II from Calmar Inc.

The cans are equipped with a suitable spray head. Depending on the spray head, ejection rates, based on completely filled cans, of from 0.1 g/s to 5.0 g/s are possible. The spray rate is determined here by firstly weighing an aerosol can filled with propellant gas and the corresponding composition and sealed with the valve in question at room temperature (about 23° C.). The can together with the contents is shaken 10 times vigorously by hand so that the contents are thoroughly mixed. The valve of the vertical can is then actuated for 10 s. It is then weighed again. The process is carried out 5 times in succession and the statistical average is calculated from the results. The difference in the two weighings is the spray rate per 10 s. The spray rate per second can be determined from this by simple division. In the case of nonaerosols, the spray mechanism is correspondingly actuated 10 times. In the latter case, the spray rate is understood as meaning the average dispensed amount per spray stroke (pump stroke). Spray rates of from 0.1 to 0.5 g/s are preferred here. Spray rates of from 0.1 to 0.4 g/s are particularly preferred.

A further characteristic influence on the efficiency and formulatability as compact spray is the spray pattern. The spray pattern is decisively influenced by the valve and its nature. If, for example, in a hairspray formulation, the film former is increased by up to five-fold compared with a conventional formulation, then, besides the increased viscosities of the formulation that are to be observed and avoided, the already discussed spray rates are also essential features to be taken into consideration for the formulation. Additionally, however, especially also the spray pattern, i.e. the opening cone of the valve, and the droplet size have to be taken into consideration.

If the opening cone has too large an opening angle, then the product is applied to too small an area of hair at a customary distance of the spray can from the head of the user of about 10 to 40 cm. This leads to a change in the effectiveness of the composition. This gives rise to either agglutinations as a result of excessively large product amounts or to too slight low a setting effect as a result of the applied amount of product being too small. In the latter case, the opening cone is too large, meaning that too large an area of the hair is treated with the composition. It has now been found that the opening cone must ideally be between 25° and 65°. An angle from 30° to 60° is preferred here. Very particular preference is given to opening cones between 35° and 50°.

The influence of the droplet size is as follows: if the droplets are too large, the distribution of the formulation on the hair is not even, meaning that excessively large amounts of product occur in many places. By contrast, in other places the product amounts that arise are too small. In numerous experiments, it has now been found that the average droplet size should ideally be less than 50 µm. Droplet sizes less than 45 µm are preferred here. Very particular preference is given to droplet sizes less than 40 µm.

The droplet size is determined here using a laser diffraction measuring instrument of the Mastersizer type, Series 2600 Droplet and Particle Size Analyzer from Malvern. For this, the sample is sprayed at a defined distance through the light beam of the laser and the particle size distribution is determined by reference to the laser diffraction.

The viscosity of the formulation to be sprayed can likewise exhibit an influence depending on the concentration of the film-forming polymers. Simultaneously, however, valves are also known with the help of which even gels can be sprayed.

Finally, the problem of the sticking of the valves can additionally be positively influenced for the targeted selection of the film-forming polymers also by appropriate careful processing, material selection and/or pretreatment of the valves. It is essential here that all of the parts of the valve that come into contact with the composition have the smoothest surface possible. The smoother the surface, the less the composition is able to stick to it through adhesion. Sticking of the nozzle is thereby counteracted. Achieving particularly smooth surfaces is known to the person skilled in the art, for example by designing the surface in the form of nanoparticles to achieve a lotus flower effect or polishing of these surfaces such as, for example, electropolishing.

As regards further design, reference is expressly made to Andreas Domsch, "Die kosmetischen Präparate" [Cosmetic Preparations], volume II, chapter 4, Aerosols, p. 259 et seq., Verlag für die chemische Industrie, H. Ziolkowsky Kg, Augsburg, 1992. It is encompassed according to the invention that the aerosol container can be made of alumonoblock cans, but also of plastics such as PET, or glass.

In all of the embodiments, the finely divided composition can in principle be applied to dry hair or to slightly damp to wet hair. Application is preferably to slightly damp to wet hair. In cases where a paintbrush is used, the paintbrush can also be already wet in order to apply larger amounts to the hair. The paintbrush can, however, also be dry and only the hair be damp to wet.

The Powder, Granules or Block Body According to the Invention.

In the text below, predominantly the term "shaped body" is used. For the purposes of the present invention, shaped body is to be understood as meaning both the powder and also granules. The term "block body" is to be understood as meaning a solid piece. The term "solid piece" is therefore also used below.

Furthermore, the granules can be produced by customary tableting methods. The term "tablet" and its modifications are therefore synonymous for the purposes of the invention with the granules according to the invention.

One variant consists in formulating the compositions according to the invention as block bodies. This variant is therefore described in detail below. The geometric spatial measurements of this embodiment are to be matched to the geometry of the storage containers. The measurements of these storage containers have already been described in the description of this embodiment. Preferably, these block bodies have dimensions and measurements like, for example, syndet or soap bars.

The shaped bodies according to the invention can assume any geometric shape, such as, for example, concave, convex, biconcave, biconvex, cubic, tetragonal, orthorhombic, cylindrical, spherical, cylinder-segment-like, disk-shaped, tetrahedral, dodecahedral, octahedral, conical, pyramidal, ellipsoidal, pentagonal-, heptagonal and octagonal-prismatic and also rhombohedric shapes. Completely irregular base areas such as arrow or animal shapes, trees, clouds etc. can also be realized. Configuration as slabs, rod or bar form, cubes, cuboids and corresponding spatial elements with plane side areas and in particular cylindrical configurations with a circular or oval cross section and shaped bodies with spherical geometry are preferred according to the invention. Particular preference is given to shaped bodies in a shape of spherical geometry.

The cylindrical configuration includes here the supply form from the tablet to compact cylinder sections with a ratio of height to diameter of greater than 1. If the basic shaped body has corners and edges, then these are preferably rounded off. As an additional optical differentiation, an embodiment with rounded corners and beveled ("chamfered") edges is preferred.

In a preferred embodiment, the portioned compacts can be designed here in each case as individual elements separate from the others which correspond to the predetermined dosage amount of the cosmetic active ingredient. However, it is likewise possible to design compacts which combine a plurality of such mass units in one compact, with the provision in particular of pregiven breakage points to make it easy to separate off portioned smaller units. Design of the portioned compacts as tablets in cylindrical or cuboid form may be expedient, in which case a diameter/height ratio in the range from about 0.1:10 to 10:0.1 is preferred. Standard commercial hydraulic presses, eccentric presses or rotary presses are suitable devices in particular for producing such compacts.

The preferred three-dimensional shape of the shaped bodies according to the invention has a rectangular base area, where the height of the shaped bodies is smaller than the smaller rectangular side of the base area. Rounded corners are preferred in the case of this supply form.

A further preferred shaped body which can be produced has a plate-like or table-like structure with alternating thick long segments and thin short segments, such that individual segments can be broken off from this "bar" at the intended breakage points, which represent the short thin segments, and be used portioned in this way. This principle of the "bar-shaped" shaped body can also be realized in other geometric shapes, for example perpendicular triangles which are joined together only along one of their sides.

If the shaped bodies according to the invention comprise at least two cosmetic active ingredients, it may be advantageous in a further embodiment, to compress the different components not exclusively to give a uniform tablet. During tableting, in this embodiment, shaped bodies are obtained which have a plurality of layers, i.e. at least two layers. In this connection, it is also possible for the different layers to have different solubility rates. Advantageous application properties of the shaped bodies can result from this. If, for example, components are present in the shaped bodies which have an adverse effect on one another, then it is possible to integrate one component in the more rapidly dissolving layer, and to incorporate the other component into a more slowly dissolving layer so that the components do not react with one another during the dissolution process.

The layer structure of the shaped bodies here can either be in the form of a stack, with a dissolution operation of the inner layer(s) already taking place at the edges of the shaped body when the outer layers have still not completely dissolved. In the case of a stack-like arrangement, the stack axis can be arranged arbitrary to the tablet axis. The stack axis can thus, for example, in the case of a cylindrical tablet, lie parallel or perpendicular to the height of the cylinder.

According to a further embodiment, it may, however, also be preferred if complete coating of the inner layer(s) is achieved by the outer layer(s) in each case, which leads to premature dissolution of constituents in the inner layer(s) being prevented. Preference is given to shaped bodies in which the layers with different active ingredients surround one another. For example, a layer (A) may be completely surrounded by the layer (B) and this in turn may be completely surrounded by the layer (C). Likewise, preference may be given to shaped bodies in which, for example, layer (C) is completely surrounded by layer (B) and this in turn is completely surrounded by layer (A).

Similar effects can also be achieved by coating individual constituents of the composition to be compressed or of the entire shaped body. For this, the bodies to be coated are sprayed, for example, with aqueous solutions or emulsions, or else are given a coating via the method of melt coating.

The (cavity) shaped bodies produced according to the invention can be provided completely or partially with a coating. Methods in which an aftertreatment consists in applying a coating layer to the shaped body surface(s) in which the filled cavity(ies) is/are located, or in applying a coating layer to the entire shaped body are preferred according to the invention.

After the compression, the shaped bodies have high stability. The fracture resistance of cylindrical shaped bodies can be ascertained via the measurement parameter of the diametral fracture stress. This can be determined according to $$\sigma = \frac{2P}{\pi Dt}$$

Here, $\sigma$ is the diametral fracture stress (DFS) in Pa, P is the force in N which leads to the pressure exerted on the shaped body which causes fracture of the shaped body, D is the diameter of the shaped body in meters and t is the height of the shaped body.

The shaped bodies of the present invention preferably have a density of from 0.3 g/cm$^3$ to 2.0 g/cm$^3$, in particular from 0.5 g/cm$^3$ to 1.1 g/cm$^3$.

Furthermore, the shaped bodies according to the invention can consist of a shaped body described by the term "basic shaped body" and produced per se by known tableting operations and which has a cavity. Preferably, the basic shaped body is firstly produced and the further compressed part is introduced into or onto this basic shaped body in a further process step. The resulting product is referred to below by the generic terms "cavity shaped bodies" or "cavity tablet."

According to the invention, the basic shaped body can in principle assume all realizable three dimensional shapes. Particular preference is given to the three dimensional shapes already specified above. The shape of the cavity can be chosen freely, preference being given according to the invention to shaped bodies in which at least one cavity can assume a concave, convex, cubic, tetragonal, orthorhombic, cylindrical, spherical, cylinder-segment-like, disk-shaped, tetrahedral, dodecahedral, octahedral, conical, pyramidal, ellipsoidal, pentagonal-, heptagonal- and octagonal-prismatic and rhombohedric shape. Completely irregular cavity shapes such as arrow or animal shapes, trees, clouds, etc. can also be realized. As with the basic shaped bodies, cavities with rounded corners and edges or with rounded corners and beveled edges are preferred.

The size of the cavity relative to the entire shaped body is governed by the desired intended use of the shaped body. The size of the cavity can vary depending on whether a smaller or larger amount of active substance is to be contained in the second compressed part. Irrespective of the intended use, preference is given to shaped bodies in which the weight ratio of basic shaped body to cavity filling is in the range from 1:1 to 100:1, preferably from 2:1 to 80:1, particularly preferably from 3:1 to 50:1 and in particular from 4:1 to 30:1.

Similar statements can be made regarding the surface components which make up the basic shaped body and/or the cavity filling relative to the overall area of the shaped body. Here, preference is given to shaped bodies in which the surface of the pressed-in cavity filling constitutes 1 to 25%, preferably 2 to 20%, particularly preferably 3 to 15% and in particular 4 to 10%, of the total surface of the filled basic shaped body.

If, for example, the total shaped body has measurements of 20×20×40 mm and thus a total area of 40 cm$^2$, then preference is given to cavity fillings which have an area of 0.4 to cm$^2$, preferably 0.8 to 8 cm$^2$, particularly preferably of 1.2 to 6 cm$^2$ and in particular from 1.6 to 4 cm$^2$.

The cavity filling and the basic shaped body are preferably colored so as to be optically distinguishable. Besides the optical differentiation, cavity tablets have application advantages on the one hand as a result of varying solubilities of the different areas, but on the other hand also as a result of the separate storage of the active ingredients in the different areas of the shaped body.

Shaped bodies in which the pressed-in cavity filling dissolves more slowly than the basic shaped body may be preferred according to the invention. By incorporating certain constituents, the solubility of the cavity filling can on the one hand be varied in a targeted manner, on the other hand the release of certain ingredients from the cavity filling can lead to advantages in the application process. As a result of varying rates of dissolution, incompatibilities of individual constituents can be prevented during dissolution.

It may be preferred according to the invention to separately encapsulate individual active ingredients prior to their incorporation into the shaped body; thus, it is, for example, conceivable to use particularly reactive components or else the fragrances in encapsulated form.

The shaped bodies according to the invention are produced firstly through the dry mixing of the constituents, which may be completely or partially pregranulated, and subsequent shaping, in particular compression to give tablets, for which it is possible to have recourse to known methods. To produce the shaped bodies according to the invention, the premix is compacted in a die between two punches to give a solid compact. This operation, which is referred to below for short as tableting, consists of four sections: metering, compaction (elastic deformation), plastic deformation and ejection.

Firstly, the premix is introduced into the die, the fill amount and thus the weight and the shape of the resulting shaped body being determined by the position of the bottom punch and the shape of the compression tool. Uniform metering, even at high shaped body throughputs, is preferably achieved via volumetric metering of the premix. In the further course of tableting, the top punch comes into contact with the premix and descends further in the direction of the bottom punch. During this compaction, the particles of the premix are pressed closer together, during which the void volume in the filling between the punches continuously decreases. Plastic deformation, during which the particles coalesce resulting in the formation of the shaped body, starts from a certain position of the top punch (and thus from a certain pressure on the premix). Depending on the physical properties of the premix, some of the premix particles are also crushed, resulting in sintering of the premix at even higher pressures. As the compression rate increases, thus at high throughputs, the elastic deformation phase becomes increasingly shorter, meaning that the resulting shaped bodies can have more or less large voids. In the final step of tableting, the finished shaped body is forced out from the die by the bottom punch and conveyed by following transportation devices. At this point, only the weight of the shaped body is definitely established since the compacts can still change shape and size as a result of physical processes (re-elongation, crystallographic effects, cooling etc.).

Tableting takes place in standard commercial tablet presses which may, in principle, be equipped with single or double punches. In the latter case, not only is the top punch used to build up pressure, the bottom punch also moves towards the top punch during the compression operation while the top punch presses downwards. For small production volumes, it is preferred to use eccentric tablet presses in which the punch(es) is/are fixed to an eccentric disk which, in turn, is mounted on an axis with a certain rotary speed. The movement of these punches is comparable with the operation of a conventional four-stroke engine. Compression can take place with a top punch and a bottom punch, although it is also possible for a plurality of punches to be fixed to one eccentric disk, in which case the number of die bores is correspondingly increased. The throughputs of eccentric presses vary according to type from a few hundred to at most 3,000 tablets per hour.

For larger throughputs, rotary tablet presses are chosen; in these, a relatively large number of dies is arranged in a circle on a die table. The number of dies varies according to model between 6 and 55, although even larger dies are commercially available. A top punch and bottom punch is allocated to each die on the die table, it again being possible for the compression pressure to be actively built up only by the top punch or bottom punch, but also by both punches. The die table and the punches move about a common vertical axis, the punches being brought into the positions for filling, compaction, plastic deformation and ejection by means of curved guide rails. At those places where the punches have to be raised or lowered to a particularly significant extent (filling, compaction, ejection), these guide rails are supported by additional push-down members, pull-down rails and ejection paths. The die is filled from a rigidly arranged feed unit, the filling shoe, which is connected to the storage container for the premix. The pressure on the premix can be individually adjusted via the tools for the top and bottom punches, pressure being built up by the rolling of the punch shank heads past adjustable pressure rollers.

To increase the throughput, rotary presses can also be provided with two filling shoes so that only half a circle has to be passed through to produce a tablet. To produce two-layer or multiple-layer shaped bodies, two or more filling shoes are arranged one behind the other without the lightly compacted first layer being ejected before further filling. By means of suitable process control, it is also possible to produce shell and bull's-eye tablets, which have a structure resembling an onion, in this way, where, in the case of the bull's-eye tablets, the upper surface of the core or the core layers is not covered and thus remains visible. Rotary tablet presses can also be equipped with single or multiple tools so that, for example, an outer circle with 50 bores and an inner circle with 35 bores can be simultaneously used for the compression. The throughputs of modern rotary tablet presses are more than one million shaped bodies per hour.

In the case of tableting using rotary presses, it has proven to be advantageous to carry out the tableting with the lowest possible fluctuations in the weight of the tablets. In this way, it is also possible to reduce the fluctuations in the hardness of the tablet. Small weight fluctuations can be achieved in the following way:
  use of plastic inserts with low thickness tolerances
  low rotor speed
  large filling shoe
  adaptation of the rotation speed of the filling shoe blade to the rotor speed
  filling shoe with constant powder height
  decoupling the filling shoe from the powder supply.

Any of the nonstick coatings known from the art may be used to reduce caking on the punch. Plastic coatings, plastic inserts or plastic punches are particularly advantageous. Rotating punches have also proven advantageous, in which case top punch and lower punch should, if possible, be designed for rotation. In the case of rotating punches, it is generally possible to dispense with a plastic insert. Here, the surfaces of the punch should be electropolished.

It has also been found that long compression times are advantageous. These can be established by using pressure rails, several pressure rollers or low rotor speeds. Since fluctuations in tablet hardness are caused by fluctuations in the compression forces, systems which limit the compression force should be used. Here, elastic punches, pneumatic compensators or spring elements in the force path can be used. The pressure roll can also be spring-mounted.

Tableting machines suitable for the purposes of the present invention are available, for example, from the following companies: Apparatebau Holzwarth GbR, Asperg, Wilhelm Fette GmbH, Schwarzenbek, Fann Instruments Company, Houston, Tex. (USA), Hofer GmbH, Weil, Horn & Noack Pharmatechnik GmbH, Worms, IMA Verpackungssysteme GmbH, Viersen, KILIAN, Cologne, KOMAGE, Kell am See, KORSCH Pressen AG, Berlin, and Romaco Gmbh, Worms. Other suppliers are, for example, Dr. Herbert Pete, Vienna (AT), Mapag Maschinenbau Ag, Berne (CH), BWI Manesty, Liverpool (GB), I. Holand Ltd., Nottingham (GB), Courtoy N. V., Halle (BE/LU) and Mediopharm Kamnik (SI). Of particular suitability is, for example, the hydraulic double-pressure press HPF 630 from LAEIS, D. Tableting tools are available, for example, from Adams Tablettierwerkzeuge, Dresden, Wilhelm Fett GmbH, Schwarzenbek, Klaus Hammer, Solingen, Herber & Söhne GmbH, Hamburg, Hofer GmbH, Weil, Horn & Noack, Pharmatechnik GmbH, Worms, Ritter Pharamatechnik GmbH, Hamburg, Romaco, GmbH, Worms and Notter Werkzeugbau, Tamm. Further suppliers are, for example, Senss AG, Reinach (CH) and Medicopharm, Kamnik (SI).

However, the method for producing the shaped bodies is not limited to compressing just one particulate premix to give a shaped body. Rather, the method can also be expanded to produce multilayer shaped bodies in a manner known per se by preparing two or more premixes which are compressed onto one another. In this process, the premix introduced firstly is lightly precompressed in order to obtain a smooth upper side that runs parallel to the base of the shaped body, and, after introducing the second premix, is end-compressed to give the finished shaped body. In the case of three-layered or multi-layered shaped bodies, further precompression takes place after each addition of premix before the shaped body is end-compressed after adding the last premix.

The compression of the particulate composition into the cavity can take place analogously to the production of the basic shaped body on tablet presses. Preference is given to a procedure in which firstly the basic shaped body with cavity is produced, then filled and then compressed again. This can be carried out by ejection of the basic shaped body from a first tablet press, filling and transportation to a second tablet press, where end-compression takes place. Alternatively, the end-compression can also take place by means of pressure rollers which roll over the shaped bodies positioned on a conveyor belt. However, it is also possible to provide a rotary tablet press with different sets of punches so that a first set of punches presses indentations into the shaped bodies and the second set of punches ensures, after filling, a planar shaped body surface through postcompression.

The shaped bodies according to the invention can be packaged after their production, the use of certain packaging systems having proven to be particularly effective because, on the one hand, these packaging systems increase the storage stability of the ingredients but, on the other hand, in some cases, also significantly improve the long-term adhesion of the cavity filling. For the purposes of the present invention, the term "packaging system" always characterizes here the primary packaging of the shaped bodies, i.e. the packaging which comes into direct contact on its inside with the shaped body surface. No requirements of any kind are placed on an optional secondary packaging, meaning that, in this regard, all customary materials and systems can be used.

According to the invention, preference is given to packaging systems which have only a low water vapor transmission. In this way, the shaped body according to the invention can be retained over a prolonged period, even if, for example, hygroscopic components are used in the shaped bodies. Particular preference is given to packaging systems which have a water vapor transmission rate of 0.1 g/m²/day to less than 20 g/m²/day when the packaging system is stored at 23° C. and a relative equilibrium moisture content of 85%. The specified temperature and moisture conditions are the test conditions specified in the DIN standard 53122, according to which minimal deviations are acceptable (23±1° C., 85±2% relative humidity). The water vapor transmission rate of a given packaging system or material can be determined by other standard methods and is also described, for example, in ASTM standard E-96-53T ("Test for measuring Water Vapor transmission of Materials in Sheet Form") and in TAPPI standard T464 m-45 ("Water Vapor Permeability of Sheet Materials at high temperature and Humidity"). The measurement principle of current methods is based here on the water absorption of anhydrous calcium chloride which is stored in a container in the corresponding atmosphere, the container being closed on top by the material to be tested. The water vapor transmission rate can be calculated from the surface of the container closed by the material to be tested (permeation surface), the increase in weight of the calcium chloride and the exposure time according to $$FDDR = \frac{24 \cdot 10000}{A} \cdot \frac{x}{y} [g/m^2/24\,h]$$

where A is the surface area of the material to be tested in cm², x is the increase in weight of the calcium chloride in g and y is the exposure time in h.

The relative equilibrium humidity, often referred to as "relative air humidity" in the measurement of the water vapor transmission rate for the purposes of the present invention is 85% at 23° C. The absorption capacity of air for water vapor increases with temperature to a particular maximum content, the saturation content, and is expressed in g/m³. Thus, for example, 1 m³ of air at 17° is saturated with 14.4 g of water vapor. A saturation at a temperature of 11° is already present with 10 g of water vapor. The relative air humidity is the ratio expressed in percent between the water vapor content actually present and the saturation content corresponding to the prevailing temperature. If, for example, air at 17° contains 12 g/m³ of water vapor, then the relative air humidity=(12/14.4) ·100=83%. If this air is cooled, saturation (100% relative humidity) is reached at the dew point (in the example: 14°), i.e. a deposit in the form of mist (dew) is formed upon further cooling. Hygrometers and psychrometers are used for the quantitative determination of humidity.

The relative equilibrium humidity of 85% at 23° C. can be adjusted to an accuracy of +/−2% relative humidity, depending on the type of instrument, for example in humidity-controlled laboratory chambers. Saturated solutions of certain salts also form, in closed systems at a given temperature, constant and well-defined relative air humidities, which are based on the phase equilibrium between partial pressure of the water, saturated solution and the sediment.

The combinations of shaped body and packaging system can for their part be packaged in secondary packagings, for example cardboard boxes or trays, with no further requirements having to be placed on the secondary packaging. Accordingly, the secondary packaging is possible, but not necessary.

The packaging system of the combination according to the invention can consist of diverse materials and assume any desired external forms. For reasons of cost and for reasons of easier processability, however, preference is given to packaging systems in which the packaging material has a low weight, is easy to process and cost-effective and also ecologically compatible.

The Composition.

In order to achieve rapid and complete dissolution with water, the composition according to the invention can comprise at least one dissolution accelerator. The term "dissolution accelerator" includes here gas-evolving components, preformed and incorporated gases, disintegrants, and mixtures thereof.

The terms "dissolution accelerator," "shaped body disintegrant" and "disintegrant" are to be understood as meaning substances which are added to tablets in order to accelerate their disintegration when bringing them into contact with water or other solvents. Reviews on this topic are given, for example, in J. Pharm. Sci. 61 (1972), Römpp Chemistry Lexikon, 9th Edition, Volume 6, p. 4440, and Voigt "Lehrbuch der pharmazeutischen Technologie [Textbook of pharmaceutical technology]" (6th Edition, 1987, pp. 182-184). As solvent enters, for example water, these substances increase their volume where, on the one hand, the intrinsic volume can be increased (swelling), and on the other hand the release of gases can also generate a pressure which disintegrates the tablet into smaller particles. In pharmacy, cellulose modifications or polymers are used for this purpose.

In one embodiment of the present invention, the dissolution accelerators used are gas-evolving components. Upon contact with water, these components react with one another with the in situ formation of gases which generate a pressure in the tablet which disintegrates the tablet into smaller particles. One example of such a system is specific combinations of suitable acids with bases. Preference is given to mono-, di- or tribasic acids with a $pK_a$ value of from 1.0 to 6.9. Preferred acids are citric acid, malic acid, maleic acid, malonic acid, itaconic acid, tartaric acid, oxalic acid, glutaric acid, glutaminic acid, lactic acid, fumaric acid, glycolic acid, and mixtures thereof. Particular preference is given to citric acid. It may be very particularly preferred to use the citric acid in particle form, where the particles have a diameter below 1,000 µm, in particular less than 700 µm, very particularly preferably less than 400 µm. Further alternative suitable acids are the homopolymers or copolymers of acrylic acid, maleic acid, methacrylic acid or itaconic acid with a molecular weight of from 2,000 to 200,000. Particular preference is given to homopolymers of acrylic acid and copolymers of acrylic acid and maleic acid. According to the invention, preferred bases are alkali metal silicates, carbonates, hydrogencarbonates, and mixtures thereof. Metasilicates, hydrogencarbonates and carbonates are particularly preferred, hydrogencarbonates are very particularly preferred. Particular preference is given to particulate hydrogencarbonates with a particle diameter of less than 1,000 µm, in particular less than 700 µm, very particularly preferably less than 400 µm. Sodium or potassium salts of the above-mentioned bases are particularly preferred. These gas-evolving components are present in the coloring shaped bodies according to the invention preferably in an amount of at least 10% by weight, in particular of at least 20% by weight.

In a further embodiment of the present invention, the gas is preformed or incorporated, meaning that upon the onset of dissolution of the shaped body, gas starts to evolve and accelerates further dissolution. Examples of suitable gases are air, carbon dioxide, $N_2O$, oxygen and/or further nontoxic, nonflammable gases.

In a further, particularly preferred embodiment of the present invention, disintegration auxiliaries, shaped body disintegrants, are incorporated as dissolution accelerators into the composition according to the invention present as shaped body in order to shorten the disintegration times.

These substances, also termed "disintegrants" on account of their effect, increase their volume as water enters "swelling." Swelling disintegration auxiliaries are, for example, synthetic polymers, such as polyvinylpyrrolidine (PVP) or natural polymers or modified natural substances such as cellulose and starch and their derivatives, alginates or casein derivatives.

For the purposes of the present invention, preferred disintegrants used are disintegrants based on cellulose, meaning that preferred shaped bodies comprise such a cellulose-based disintegrant in amounts of from 0.5 to 50% by weight, preferably 3 to 30% by weight, based on the total shaped body. Pure cellulose has the formal gross composition (C6H10O5)n and, considered formally, represents a β-1,4-polyacetal of celloboise, which in turn is composed of two molecules of glucose. Suitable celluloses consist here of about 500 to 5,000 glucose units and accordingly have average molar masses of from 50,000 to 500,000. For the purposes of the present invention, cellulose-based disintegrants that can be used are also cellulose derivatives which are obtainable by polymer-analogous reactions from cellulose. Such chemically modified celluloses here include, for example, products from esterifications or etherifications in which hydroxy-hydrogen atoms have been substituted. However, celluloses in which the hydroxy groups have been replaced by functional groups which are not bonded by an oxygen atom can also be used as cellulose derivatives. The group of cellulose derivatives includes, for example, alkali metal celluloses, carboxymethylcellulose (CMC), cellulose esters and cellulose ethers, and also aminocelluloses. The specified cellulose derivatives are preferably not used as the sole cellulose-based disintegrant, but in a mixture with cellulose. The content of cellulose derivatives in these mixtures is preferably below 50% by weight, particularly preferably below 20% by weight, based on the cellulose-based disintegrant. As cellulose-based disintegrant, particular preference is given to using pure cellulose which is free from cellulose derivatives.

The cellulose used as disintegration auxiliary cannot be used in finely divided form, but, prior to admixing with the premixes to be compressed, is converted to a coarser form, for example granulated or compacted. The particle sizes of such disintegrants are mostly above 200 µm, preferably to at least 90% by weight between 300 and 1,600 µm and in particular to at least 90% by weight between 400 and 1,200 µm. The disintegration auxiliaries according to the invention are commercially available, for example, under the name Arbocel® from Rettenmaier. A preferred disintegration auxiliary is, for example, Arbocel® TF-30-HG.

A cellulose-based disintegrant or constituent of this component used is preferably microcrystalline cellulose. This microcrystalline cellulose is obtained by partial hydrolysis of celluloses under conditions which attack and completely dissolve only the amorphous areas (about 30% of the total cellulose mass) of the celluloses, but leave the crystalline areas (about 70%) intact. Subsequent deaggregation of the microfine celluloses that form as a result of the hydrolysis produces the microcrystalline celluloses which have primary particle sizes of about 5 µm and can be compacted to give granules with an average particle size of 200 µm. Suitable microcrystalline cellulose is commercially available, for example, under the trade name Avicel®.

Further disintegrants which may be present for the purposes of the invention, such as, for example, collidone, alginic acid and alkali metal salts thereof, amorphous and also partially crystalline sheet silicates (bentonites), polyacrylates, polyethylene glycols, are given, for example, in the printed specifications WO 98/40462 (Rettenmaier), WO 98/55583 and WO 98/55590 (Unilever) and WO 98/40463, DE 19709991 and DE 19710254 (Henkel). Reference is expressly made to the teaching of these specifications. The disintegrants obtainable by the method according to the invention can be present, when viewed macroscopically, in homogeneous distribution but, when viewed microscopically, they form zones of increased concentration as a result of the preparation.

The accelerated dissolution of the cosmetic compositions according to the invention present as shaped bodies can also be achieved according to the invention by pregranulation of the further constituents of the shaped body.

In a preferred embodiment of the cosmetic compositions according to the invention present as shaped bodies, these comprise a mixture of starch and at least one saccharide in addition to the dissolution accelerator. The use of disaccharides according to this embodiment is preferred. Said mixture is preferably present in a weight ratio of starch and the saccharides used of from 10:1 to 1:10, particularly preferably from 1:1 to 1:10, very particularly preferably from 1:4 to 1:7, in the shaped body.

The disaccharides used are preferably selected from lactose, maltose, sucrose, trehalose, turanose, gentiobiose, melibiose and cellobiose. Particular preference is given to using lactose, maltose and sucrose and very particular preference is given to using lactose in the shaped bodies according to the invention.

The starch-disaccharide mixture is present in the shaped body in an amount of from 5 to 60% by weight, preferably from 20 to 40% by weight, based on the mass of the total shaped body.

A further essential constituent of the compositions according to the invention present as shaped bodies may be builders. Typical examples of builders, which are suitable as optional component, are zeolites, waterglasses, sheet silicates, phosphates and polycarboxylates. The finely crystalline, synthetic and bonded-water-containing zeolite often used as detergent builder is preferably zeolite A and/or P. As zeolite P, particular preference is given, for example, to zeolite MAP® (commercial product from Crosfield). However, zeolite X and mixtures of A, X and/or P and also Y are also suitable. Of particular interest is also a cocrystallized sodium/potassium-aluminum silicate of zeolite A and zeolite X, which is commercially available as VEGOBOND AX® (commercial product from Condea Augusta S.p.A.). The zeolite can be used as spray-dried powder or else as undried stabilized suspension still moist from its preparation. In cases where the zeolite is used as suspension, the latter can comprise small additions of nonionic surfactants as stabilizers, for example 1 to 3% by weight, based on zeolite, of ethoxylated C12-C18-fatty alcohols having 2 to 5 ethylene oxide groups, C12-C14-fatty alcohols having 4 to 5 ethylene oxide groups or ethoxylated isotridecanols. Suitable zeolites have an average particle size of less than 10 μm (volume distribution; measurement method: Coulter Counter) and comprise preferably 18 to 22% by weight, in particular 20 to 22% by weight, of bonded water.

Suitable substitutes or partial substitutes for phosphates and zeolites are crystalline, layered sodium silicates of the formula NaMSixO2x+1.yH2O, where M is sodium or hydrogen, x is a number from 1.9 to 4 and y is a number from 0 to 20 and preferred values for x are 2, 3 or 4. Such crystalline sheet silicates are described, for example, in the European patent application EP 0164514 A1. Preferred crystalline sheet silicates of the given formula are those in which M is sodium and x assumes the values 2 or 3. In particular, preference is given to both β- and also δ-sodium disilicates Na2Si2O5.yH2O, where β-sodium disilicate can be obtained, for example, by the method described in the international patent application WO 91/08171. Further suitable sheet silicates are known, for example, from the patent applications DE 2334899 A1, EP 0026529 A1 and DE 3526405 A1. Their applicability is not limited to a specific composition or structural formula. However, preference is given here to smectites, in particular bentonites. Suitable sheet silicates which belong to the group of water-swellable smectites are, for example, those of the general formulae

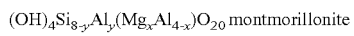 montmorillonite

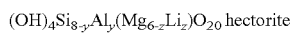 hectorite

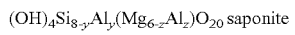 saponite where x=0 to 4, y=0 to 2, z=0 to 6. Additionally, small amounts of iron may be incorporated into the crystal lattice of the sheet silicates according to the above formulae. In addition, on account of their ion-exchanging properties, the sheet silicates can contain hydrogen ions, alkali metal ions, alkaline earth metal ions, in particular $Na^+$ and $Ca^{2+}$. The amount of water of hydration is mostly in the range from 8 to 20% by weight and is dependant on the swell state and/or on the type of processing. Sheet silicates that can be used are known, for example, from U.S. Pat. Nos. 3,966,629, 4,062,647, EP 0026529 A1 and EP 0028432 A1. Preference is given to using sheet silicates which, on account of an alkali treatment, are largely free from calcium ions and highly coloring iron ions.

Preferred builder substances also include amorphous sodium silicates with an Na2O:SiO2 modulus of from 1:2 to 1:3.3, preferably from 1:2 to 1:2.8 and in particular from 1:2 to 1:2.6, which have delayed dissolution. The dissolution delay compared with conventional amorphous sodium silicates can have been brought about in various ways, for example through surface treatment, compounding, compaction/compression or by overdrying. For the purposes of this invention, the term "amorphous" is also understood as meaning "X-ray amorphous." This means that, in X-ray diffraction experiments, the silicates do not produce sharp X-ray reflections, as are typical for crystalline substances, but at best one or more maxima of the scattered X-ray radiation which have a breadth of several degree units of the diffraction angle. However, builder properties, even particularly good builder properties, can very likely result if the silicate particles produce blurred or even sharp diffraction maxima in electron diffraction experiments. This is to be interpreted to the effect that the products have microcrystalline ranges of the order 10 to a few hundred nm, with values up to a maximum of 50 nm and in particular up to a maximum of 20 nm are preferred. Those X-ray amorphous silicates which likewise have dissolution delay compared with conventional waterglasses are described, for example, in the German patent application DE 4400024 A1. Particular preference is given to compressed/compacted amorphous silicates, compounded amorphous silicates and overdried X-ray amorphous silicates.

A use of the generally known phosphates as builder substances is also possible provided such a use is not to be avoided for ecological reasons. In particular, the sodium salts of the orthophosphates, of the pyrophosphates and in particular of the tripolyphosphates are suitable. Their content is generally not more than 25% by weight, preferably not more than 20% by weight, in each case based on the finished composition. In some cases, it has been found that in particular tripolyphosphates, even in small amounts up to at most 10% by weight, based on the finished composition, in combination with other builder substances lead to a synergistic improvement in the secondary detergency.

Useful organic builder substances which are contemplated as cobuilders are, for example, the polycarboxylic acids that can be used in the form of their sodium salts, such as citric acid, adipic acid, succinic acid, glutaric acid, tartaric acid, sugar acids, aminocarboxylic acids, nitrilotriacetic acid (NTA), provided such a use is not objectionable on ecological grounds, and also mixtures of these. Preferred salts are the salts of the polycarboxylic acids, such as citric acid, adipic acid, succinic acid, glutaric acid, tartaric acid, sugar acids and mixtures of these. The acids per se can also be used. Besides their builder effect, the acids typically also have the property of an acidifying component and thus also serve to establish a lower and more mild pH of detergents or cleaners. In particular, citric acid, succinic acid, glutaric acid, adipic acid, gluconic acid and any mixtures of these are to be mentioned here.

Further suitable organic builder substances are dextrins, for example oligomers or polymers of carbohydrates, which can be obtained by partial hydrolysis of starches. The hydrolysis can be carried out by customary, for example acid-catalyzed or enzyme-catalyzed, methods. They are preferably hydrolysis products with mean molar masses in the range from 400 to 500,000. Here, a polysaccharide with a dextrose equivalent (DE) in the range from 0.5 to 40, in particular from 2 to 30, is preferred, where DE is a customary measure of the reducing effect of a polysaccharide compared to dextrose, which has a DE of 100. It is possible to use either maltodextrins with a DE between 3 and 20 and dry glucose syrups with a DE between 20 and 37, or else yellow dextrins and white dextrins with higher molar masses in the range from 2,000 to 30,000. A preferred dextrin is described in the British patent application GB 9419091 A1. The oxidized derivatives of such dextrins are their reaction products with oxidizing agents which are able to oxidize at least one alcohol function of the saccharide ring to the carboxylic acid function. Such oxidized dextrins and processes for their preparation are known, for example, from the European patent applications EP 0232202 A1, EP 0427349 A1, EP 0472042 A1 and EP 0542496 A1, and the international patent applications WO 92/18542, WO 93/08251, WO 93/16110, WO 94/28030, WO 95/07303, WO 95/12619 and WO 95/20608. An oxidized oligosaccharide according to the German patent application DE 19600018 A1 is likewise suitable. A product oxidized on $C_6$ of the saccharide ring may be particularly advantageous.

Further suitable cobuilders are oxydisuccinates and other derivatives of disuccinates, preferably ethylenediaminedisuccinate. In this connection, particular preference is also given to glycerol disuccinates and glycerol trisuccinates, as are described, for example, in the US-American patent specifications U.S. Pat. Nos. 4,524,009, 4,639,325, in the European patent application EP 0150930 A1 and the Japanese patent application JP 93/339896. Suitable use amounts in zeolite-containing and/or silicate-containing formulations are 3 to 15% by weight. Further useful organic cobuilders are, for example, acetylated hydroxycarboxylic acids and salts thereof, which may optionally also be present in lactone form and contain at least 4 carbon atoms and at least one hydroxy group and also at most two acid groups. Cobuilders of this type are described, for example, in the international patent application WO 95/20029.

Suitable polymeric polycarboxylates are, for example, the sodium salts of polyacrylic acid or of polymethacrylic acid, for example those with a relative molecular mass of from 800 to 150,000 (based on acid and measured in each case against polystyrenesulfonic acid). Suitable copolymeric polycarboxylates are in particular those of acrylic acid with methacrylic acid and of acrylic acid or methacrylic acid with maleic acid. Copolymers of acrylic acid with maleic acid which contain 50 to 90% by weight of acrylic acid and 50 to 10% by weight of maleic acid have proven particularly suitable. Their relative molecular mass, based on free acids, is generally 5,000 to 200,000, preferably 10,000 to 120,000 and in particular 50,000 to 100,000 (in each case measured against polystyrenesulfonic acid). The (co)polymeric polycarboxylates can either be used as powder or as aqueous solution, with 20 to 55% strength by weight aqueous solutions being preferred. Granular polymers are in most cases mixed in subsequently to one or more base granules. Biodegradable polymers of more than two different monomer units, for example those which, according to DE 4300772 A1, contain, as monomers, salts of acrylic acid and of maleic acid and also vinyl alcohol or vinyl alcohol derivatives or, according to DE 4221381 C2, contain, as monomers, salts of acrylic acid and of 2-alkylallylsulfonic acid and also sugar derivatives are particularly preferred. Further preferred copolymers are those which are described in the German patent applications DE 4303320 A1 and DE 4417734 A1 and have, as monomers, preferably acrolein and acrylic acid/acrylic acid salts or acrolein and vinyl acetate. As further preferred builder substances, polymeric aminodicarboxylic acids, salts thereof or precursor substances thereof are likewise to be mentioned. Particular preference is given to polyaspartic acids and salts and derivatives thereof.

Further suitable builder substances are polyacetals which can be obtained by reacting dialdehydes with polyol carboxylic acids which have 5 to 7 carbon atoms and at least 3 hydroxyl groups, for example as described in the European patent application EP 0280223 A1. Preferred polyacetals are obtained from dialdehydes such as glyoxal, glutaraldehyde, terephthalaldehyde and mixtures thereof and from polyol carboxylic acids such as gluconic acid and/or glucoheptonic acid.

The solid bars and granules can furthermore comprise framework substances. The framework substances used are water-soluble structurants, such as, for example, starch, preferably wheat starch or corn starch.

Particular preference is given to the use of wheat starch and/or corn starch which can be used untreated or in digested form, i.e. partially hydrolyzed or acid-degraded form. Untreated starch has the advantage that it is present in the form of small solid grains in the solid bars. Hydrolyzed starch leads to products with better shapeability and homogeneity.

Particular preference is given to the use of wheat starch and/or corn starch which can be used untreated or preferably in digested, i.e. partially hydrolyzed, form.

Builders that can be present are also finely divided, water-insoluble alkali metal aluminum silicates, with the use of synthetic crystalline sodium alumosilicates containing bonded water and here, in particular, of zeolite A being particularly preferred; zeolite NaX and mixtures thereof with zeolite NaA can likewise be used. Suitable zeolites have a calcium binding capacity in the range from 100 to 200 mg CaO/g. Liquid builders that can be used are also NTA and/or EDTA.

Talc is a hydrated magnesium silicate of theoretical composition $3MgO.4SiO_2.H_2O$ or $Mg_3 (Si_4O_{10}).(OH)_2$ which, however, can contain fractions of hydrated magnesium aluminum silicate in an amount which can constitute an $Al_2O_3$ content of up to 12% by weight.

The particle diameter (equivalent spherical diameter) of the talc should be in the range from 0.5 to 50 μm. In general, those talc grades which comprise not more than 5% by weight of particles below 1 μm and not more than 5% by weight of particles above 50 μm in size have proven useful. Preferably, the fraction of particles which is greater than 40 μm in diameter (of residue) is at most 2% by weight, the average particle diameter is preferably 5 to 15 μm.

The content of accompanying substances should not constitute more than 1.6% by weight of $Fe_2O_3$, 1% by weight of CaO and 1% by weight of unbonded water (dry loss at 105° C.). The content of hydrated magnesium aluminum silicate can constitute up to 60% by weight (calculated as $Al_2O_3$ up to 12% by weight).

Suitable finely divided, water-insoluble alkali metal aluminum silicates are synthetic crystalline sodium alumosilicates containing bonded water, preferably zeolite NaA. It is also possible to use zeolite NaX and mixtures thereof with zeolite NaA. Suitable zeolites have a calcium binding capacity which is determined according to the details in DE 24 12 837 and which is in the range from 100 to 200 mg of CaO/g. Preferably, the zeolite NaA obtainable with the trade name Wessalith P (Degussa) with a content of about 20% by weight of bonded water is used in an amount of 8-15% by weight.

Suitable plasticizers are fatty alcohols, fatty acid partial glycerides or wax esters having in each case 12 to 22 carbon atoms in the fatty radicals. In this regard, reference may also be made to the statements regarding the fatty substances (D).

For example, the preferred pH is between 2 and 11, with values from 2 to 8 being particularly preferred.

To improve the processability, hydrotropes, such as, for example, ethanol, isopropyl alcohol, or polyols, can also be used. Polyols which are suitable here preferably have 2 to 15 carbon atoms and at least two hydroxyl groups. As hydrotropes it is also possible to use many of the compounds described below under the polyhydroxy compounds. Typical examples are glycerol;
in order to achieve rapid and complete dissolution with water, alkylene glycols, such as, for example, ethylene glycol, diethylene glycol, propylene glycol, butylene glycol, hexylene glycol, and polyethylene glycols with an average molecular weight of from 100 to 1,000 Daltons;
technical-grade oligoglycerol mixtures with a degree of self-condensation of from 1.5 to 10, such as, for example, technical-grade diglycerol mixtures with a diglycerol content of from 40 to 50% by weight;
methyol compounds, such as, in particular, trimethylolethane, trimethylolpropane, trimethylolbutane, pentaerythritol and dipentaerythritol;
lower alkyl glucosides, in particular those with 1 to 8 carbon atoms in the alkyl radical, such as, for example, methyl glucoside and butyl glucoside;
sugar alcohols having 5 to 12 carbon atoms, such as, for example, sorbitol or mannitol,
sugars having 5 to 12 carbon atoms, such as, for example, glucose or sucrose; amino sugars, such as, for example, glucamine.

A common feature of all pulverulent formulations is that they comprise at least one polymer (G). In a preferred embodiment of the pulverulent or bar-shaped bodies according to the invention, polymers are therefore added to the compositions used according to the invention, with both cationic, anionic, amphoteric and also nonionic polymers having proven suitable in principle. Within the group of polymers, the charged polymers have proven more advantageous over the nonionic polymers. Within the charged polymers, the cationic polymers and the amphoteric polymers are in turn preferred.

Some examples of particularly preferred polymers are described below.

The polymers that can be used according to the invention can here be differentiated on account of the charges of the polymers and/or on account of their applications-related particularly marked properties. The expression "particularly marked properties" reflects the fact that polymers generally combine two or more properties in one molecule. However, one of the properties is quite particularly at the fore and is decisive for selecting precisely this polymer.

Firstly, polymers are described on the basis of their particular charges.

Cationic polymers are to be understood as meaning polymers which have, in the main chain and/or side chain, a group which can be "temporarily" or "permanently" cationic. According to the invention, "permanently cationic" is the term used to refer to those polymers which, irrespective of the pH of the composition, have a cationic group. These are generally polymers which contain a quaternary nitrogen atom, for example in the form of an ammonium group. Preferred cationic groups are quaternary ammonium groups. In particular, those polymers in which the quaternary ammonium group is bonded via a C1-4 hydrocarbon group to a polymer main chain composed of acrylic acid, methacrylic acid or derivatives thereof have proven to be particularly suitable.

Further cationic polymers according to the invention are the "temporarily cationic" polymers. These polymers usually contain an amino group which, at a certain pH, is present in the form of a quaternary ammonium group and thus cationic.

The cationic polymers according to the invention can be either setting and/or film-forming and/or antistatic and/or finishing polymers, or else polymers with conditioning and/or thickening properties. Suitable cation-active polymers are preferably hair-setting and/or hair-conditioning polymers. Polymers are to be understood as meaning both natural and synthetic polymers which may be cationically or amphoterically charged.

Preference is given to those polymers which have adequate solubility in water or alcohol to completely dissolve in the composition according to the invention when applied to damp to wet hair. The cationic charged density is preferably 1 to 7 meq/g.

The cationic polymers may be homopolymers or copolymers, where the quaternary nitrogen groups are present either in the polymer chain or preferably as substituent on one or more of the monomers. The monomers containing ammonium groups can be copolymerized with noncationic monomers.

Suitable cationic monomers are unsaturated, free-radically polymerizable compounds which carry at least one cationic group, in particular ammonium-substituted vinyl monomers, such as, for example, trialkylmethacryloxyalkylammonium, trialkylacryloxyalkylammonium, dialkyldiallylammonium and quaternary vinylammonium monomers with cyclic groups containing cationic nitrogens, such as pyridinium, imidazolium or quaternary pyrrolidones, e.g., alkylvinylimidazolium, alkylvinylpyridinium, or alkylvinylpyrrolidone salts. The alkyl groups of these monomers are preferably lower alkyl groups, such as, for example, C1- to C7-alkyl groups, particularly preferably C1- to C3-alkyl groups.

The monomers containing ammonium groups can be copolymerized with noncationic monomers. Suitable comonomers are, for example, acrylamide, methacrylamide; alkyl- and dialkylacrylamide, alkyl- and dialkylmethacrylamide, alkyl acrylate, alkyl methacrylate, vinylcaprolactone, vinylcaprolactam, vinylpyrrolidone, vinyl esters, e.g., vinyl acetate, vinyl alcohol, propylene glycol or ethylene glycol, where the alkyl groups of these monomers are preferably C1- to C7-alkyl groups, particularly preferably C1- to C3-alkyl groups.

Suitable polymers having quaternary amine groups are, for example, the polymers described in the CTFA Cosmetic Ingredient Dictionary under the names Polyquaternium, such as methylvinylimidazolium chloride/vinylpyrrolidone copolymer (Polyquaternium-16) or quaternized vinylpyrrolidone/dimethylaminoethyl methacrylate copolymer (Polyquaternium-11) and also quaternary silicone polymers and oligomers, such as, for example, silicone polymers with quaternary end groups (quaternium-80).

Of the cationic polymers which may be present in the agent according to the invention, vinylpyrrolidone/dimethylaminoethyl methacrylate methosulfate copolymer, which is sold under the trade names Gafquat® 755 N and Gafquat® 734 by Gaf Co., USA, and of which Gafquat® 734 is particularly preferred, for example, is suitable. Further cationic polymers are, for example, the copolymer of polyvinylpyrrolidone and imidazolium methochloride sold by BASF, Germany under the trade name Luviquat® HM 550, the terpolymer of dimethyldiallylammonium chloride, sodium acrylate and acrylamide sold by Calgon/USA under the trade name Merquat® Plus 3300 and the vinylpyrrolidone/methacrylamidopropyltrimethylammonium chloride copolymer sold under the trade name Gafquat® HS 100.

Homopolymers of the general formula (G1-I)

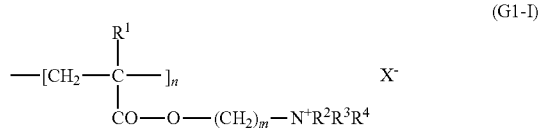

(G1-I)

in which $R^1$=—H or —$CH_3$, $R^2$, $R^3$ and $R^4$, independently of one another, are selected from C1-4-alkyl, -alkenyl or -hydroxyalkyl groups, m=1, 2, 3 or 4, n is a natural number and $X^-$ is a physiologically compatible organic or inorganic anion, and also copolymers consisting essentially of the monomer units detailed in formula (G1-I), and also nonionogenic monomer units are particularly preferred cationic polymers. Within the scope of these polymers, preference is given according to the invention to those for which at least one of the following conditions applies:

$R^1$ is a methyl group
$R^2$, $R^3$ and $R^4$ are methyl groups
m has the value 2.

Suitable physiologically compatible counterions $X^-$ are, for example, halide ions, sulfate ions, phosphate ions, methosulfate ions and organic ions such as lactate, citrate, tartrate and acetate ions. Preference is given to halide ions, in particular chloride.

A particularly suitable homopolymer is the poly(methacryloyloxyethyltrimethylammonium chloride), if desired crosslinked, having the INCI name Polyquaternium-37. Such products are commercially available, for example, under the names Rheocare® CTH (Cosmetic Rheologies) and Synthalen® CR (3V Sigma). The crosslinking can take place, if desired, with the help of polyolefinically unsaturated compounds, for example divinylbenzene, tetraallyloxyethane, methylenebisacrylamide, diallyl ether, polyallyl polyglycerol ether, or allyl ethers of sugars or sugar derivatives such as erythritol, pentaerythritol, arabitol, mannitol, sorbitol, sucrose or glucose. Methylenebisacrylamide is a preferred crosslinking agent.

The homopolymer is preferably used in the form of a nonaqueous polymer dispersion which should have a polymer fraction not below 30% by weight. Such polymer dispersions are commercially available under the names Salcare® SC 95 (about 50% polymer fraction, further components: mineral oil (INCI name: Mineral Oil) and tridecylpolyoxypropylene polyoxyethylene ether (INCI name: PPG-1-Trideceth-6)) and Salcare® SC 96 (about 50% polymer fraction, further components: mixture of diesters of propylene glycol with a mixture of caprylic acid and capric acid (INCI name: Propylene Glycol Dicaprylate/Dicaprate) and tridecylpolyoxypropylene polyoxyethylene ether (INCI name: PPG-1-Trideceth-6)).

Copolymers with monomer units according to formula (G1-l) contain, as nonionogenic monomer units, preferably acrylamide, methacrylamide, $C_{1-4}$-alkyl esters of acrylic acid and $C_{1-4}$-alkyl esters of methacrylic acid. Among these nonionogenic monomers, acrylamide is particularly preferred. As in the case of the homopolymers described above, these copolymers can also be crosslinked. A copolymer preferred according to the invention is the crosslinked acrylamide-methacryloyloxyethyltrimethylammonium chloride copolymer. Such copolymers in which the monomers are present in a weight ratio of about 20:80 are commercially available as about 50% strength nonaqueous polymer dispersion under the name Salcare® SC 92.

Suitable cation-active silicone compounds preferably have either at least one amino group or at least one ammonium group. Suitable silicone polymers with amino groups are known under the INCI name Amodimethicones. These are polydimethylsiloxanes with aminoalkyl groups. The aminoalkyl groups can be lateral or terminal. The N-containing silicone as cationic polymer (C1) according to the invention can preferably be selected from the group comprising siloxane polymers with at least one amino group, siloxane polymers with at least one terminal amino group, aminodimethicone, trimethylsilylamodimethicones, and/or aminoethylaminopropylsiloxane-dimethylsiloxane copolymer. Suitable silicone polymers with two terminal quaternary ammonium groups are known under the INCI name Quaternium-80. These are dimethylsiloxanes with two terminal aminoalkyl groups.

According to the invention, preference is given to the use of an aminosiloxane corresponding to the general formula (G1-II) below

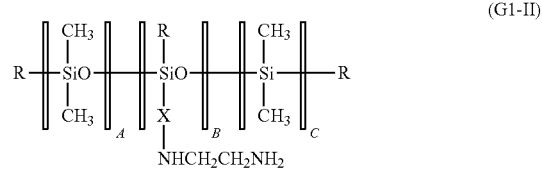

(G1-II)

where R=OH or $CH_3$; X=alkyl group having 1 to 4 carbon atoms, preferably propyl or isopropyl, and A, B and C=copolymer units which can form tactic and/or atactic polymer blocks.

According to the invention, amodimethicone, amodimethicone-containing emulsions or fluids are most preferred. Emulsions which can preferably be used according to the invention are Dow Corning® 949, which is a cationic emulsion comprising amodimethicone, cetrimonium chloride and trideceth-12; Dow Corning® 939, which is an emulsion comprising amodimethicone, cetrimonium chloride and trideceth-12; Dow Corning® 929, which is a cationic emulsion comprising amodimethicone, talc trimonium chloride and nonoxynol-10; Dow Corning® 7224 or 1401, based on trimethylsilylamodimethicone, octoxynol-40, isolaureth-6 and glycol; Dow Corning® 2-8194 Microemulsion (26% strength) based on an amine-functionalized silicone polymer; Dow Corning® 2-8177 Microemulsion (12% strength) based on an amine-functionalized silicone polymer; Dow Corning® 2-8566 amino fluid based on an amine-functionalized polydimethylsiloxane; available from Dow Corning.

The molecular weight of the aminosilicones is preferably between 500 and 100,000. The amine fraction (meq/g) is preferably in the range from 0.05 to 2.3, particularly preferably from 0.1 to 0.5

The silicone as cationic polymer according to the invention is used in an amount of from 0.01 to 20% by weight, based on the total agent, preferably in amounts of from 0.05 to 15% by weight and very particularly preferably in amounts of from 0.05 to 10% by weight.

Suitable cationic polymers which are derived from natural polymers are cationic derivatives of polysaccharides, for example cationic derivatives of cellulose, starch or guar. Also suitable are chitosan and chitosan derivatives. Cationic polysaccharides have the general formula (G1-III) G-O—B—N+$R_a R_b R_c X^-$ G is an anhydroglucose radical, for example starch anhydroglucose or cellulose anhydroglucose;

B is a divalent joining group, for example alkylene, oxyalkylene, polyoxyalkylene or hydroxyalkylene;

$R_a$, $R_b$ and $R_c$, independently of one another, are alkyl, aryl, alkylaryl, arylalkyl, alkoxyalkyl or alkoxyaryl having in each case up to 18 carbon atoms, where the total number of carbon atoms in $R_a$, $R_b$ and $R_c$ is preferably at most 20;

$X^-$ is a customary counterion and is preferably chloride.

A cationic cellulose is sold under the name polymer JR® by Amerchol and has the INCI name Polyquaternium-10. A further cationic cellulose bears the INCI name Polyquaternium-24 and is sold under the trade name Polymer LM-200 by Amerchol. A suitable cationic guar derivative is sold under the trade name Jaguar® and has the INCI name Guar Hydroxypropyltrimonium Chloride.

Particularly preferred cation-active substances are chitosan, chitosan salts and chitosan derivatives. The chitosan derivatives are one example of a cationic polymer which has marked properties as film former. The chitosans to be used according to the invention are completely or partially deacetylated chitins. For the preparation of chitosan, the starting point is preferably the chitin present in the shell residues of crustations, which is available as an inexpensive and natural raw material in large amounts. The molecular weight of chitosan can be distributed over a broad spectrum, for example from 20,000 to about 5 million g/mol. A low molecular weight chitosan with a molecular weight of from 30,000 to 70,000 g/mol, for example, is suitable. Preferably, however, the molecular weight is above 100,000 g/mol, particularly preferably from 200,000 to 700,000 g/mol. The degree of deacetylation is preferably 10 to 99%, particularly preferably 60 to 99%.

A suitable chitosan is sold, for example, by Kyowa Oil & Fat, Japan under the trade name Flonac®. It has a molecular weight of from 300,000 to 700,000 g/mol and is 70 to 80% deacetylated. A preferred chitosan salt is chitosonium pyrrolidone carboxylate which is sold, for example, under the name Kytamer® PC by Amerchol, USA. The chitosan present has a molecular weight of from about 200,000 to 300,000 g/mol and is 70 to 85% deacetylated. Suitable chitosan derivatives are quaternized, alkylated or hydroxyalkylated derivatives, for example hydroxyethyl chitosan or hydroxybutyl chitosan. Further chitosan derivatives are freely commercially available under the trade names Hydagen® CMF, Hydragen® HCMF and Chitolam® NB/101.

The chitosans or chitosan derivatives are preferably present in neutralized or partially neutralized form. The degree of neutralization for the chitosan or the chitosan derivative is preferably at least 50%, particularly preferably between 70 and 100%, based on the number of free base groups. Neutralizing agents which can be used are in principle all cosmetically compatible inorganic or organic acids, such as, for example, formic acid, tartaric acid, maleic acid, lactic acid, citric acid, pyrrolidone carboxylic acid, hydrochloric acid etc., of which pyrrolidone carboxylic acid is particularly preferred.

Further preferred cationic polymers are, for example, quaternized cellulose derivatives, as are commercially available under the names Celquat® and Polymer JR®. The compounds Celquat® H 100, Celquat® L 200 and Polymer JR® 400 are preferred quaternized cellulose derivatives, cationic alkyl polyglycosides as in the DE patent specification 44 13 686, cationized honey, for example the commercial product Honeyquat® 50, cationic guar derivatives, such as in particular the product sold under the trade names Cosmedia® Guar and Jaguar®, polymeric dimethyldiallylammonium salts and copolymers thereof with esters and amides of acrylic acid and methacrylic acid. The products commercially available under the names Merquat® 100 (poly(dimethyldiallylammonium chloride)) and Merquat®550 (dimethyldiallylammonium chloride-acrylamide copolymer) are examples of such cationic polymers, copolymers of vinylpyrrolidone with quaternized derivatives of dialkylaminoalkyl acrylate and methacrylate, such as, for example, vinylpyrrolidone-dimethylaminoethyl methacrylate copolymers quaternized with diethyl sulfate. Such compounds are commercially available under the names Gafquat® 734 and Gafquat® 755, vinylpyrrolidone-vinylimidazolium methochloride copolymers, as are supplied under the names Luviquat® FC 370, FC 550, FC 905 and HM 552, quaternized polyvinyl alcohol, and the polymers with quaternary nitrogen atoms in the polymer main chain known under the names Polyquaternium 2, Polyquaternium 17, Polyquaternium 18 and Polyquaternium 27, vinylpyrrolidone-vinylcaprolactam-acrylate terpolymers, as are supplied with acrylic acid esters and acrylamides as third monomer building block commercially for example under the names Gaffix® VC 713 or Aquaflex® SF 40.

Cationic polymers that can likewise be used are the polymers known under the names Polyquaterium-24 (commercial product e.g., Quatrisoft® LM 200). The copolymers of vinylpyrrolidone as are available as commercial product copolymer 845 (manufacturer: ISP), Gaffix®VC 713 (manufacturer: ISP), Gafquat®ASCP 1011, Gafquat® HS 110, Luviquat® 8155 and Luviquat® MS 370 can likewise be used according to the invention.

Further cationic polymers that can be used in the agents according to the invention are the "temporarily cationic" polymers. These polymers usually contain an amino group which, at certain pH values, is present in the form of a quaternary ammonium group and thus cationic. Preference is given, for example, to chitosan and derivatives thereof, as are freely commercially available, for example, under the tradenames Hydagen® CMF, Hydagen® HCMF, Kytamer® PC and Chitolam® NB/101.

Cationic polymers preferred according to the invention are cationic cellulose derivatives and chitosan and derivatives thereof, in particular the commercial products Polymer® JR 400, Hydagen® HCMF and Kytamer® PC, cationic guar derivatives, cationic honey derivatives, in particular the commercial product Honeyquat® 50, cationic alkyl polyglycosides as in DE patent specification 44 13 686 and polymers of the Polyquaternium-37 type.

Furthermore, cationized protein hydrolysates are types of cationic polymers, where the parent protein hydrolysate can originate from animal, for example from collagen, milk or keratin, from plant, for example from wheat, corn, rice, potatoes, soya or almonds, from marine life forms, for example from fish collagen or algae, or biotechnologically obtained protein hydrolysates. The protein hydrolysates on which the cationic derivatives according to the invention are based can be obtained from the corresponding proteins by a chemical, in particular alkaline or acidic, hydrolysis, by an enzymatic hydrolysis and/or a combination of the two types of hydrolysis. The hydrolysis of proteins generally gives a protein hydrolysate with a molecular weight distribution ranging from about 100 Daltons to several thousand Daltons. Preference is given to those cationic protein hydrolysates whose underlying protein moiety has a molecular weight of from 100 to 25,000 Daltons, preferably 250 to 5,000 Daltons. Furthermore, cationic protein hydrolysates are to be understood as meaning quaternized amino acids and mixtures thereof. The quaternization of the protein hydrolysates or of the amino acids is often carried out by means of quaternary ammonium salts, such as, for example, N,N-dimethyl-N-(n-alkyl)-N-(2-hydroxy-3-chloro-n-propyl)ammonium halides. Furthermore, the cationic protein hydrolysates can also be yet further derivatized. Typical examples of the cationic protein hydrolysates and derivatives according to the invention that may be mentioned are the products specified under the INCI names in the "International Cosmetic Ingredient Dictionary and Handbook," (Seventh Edition 1997, The Cosmetic, Toiletry, and Fragrance Association 1101 17th Street, N.W., Suite 300, Washington, D.C. 20036-4702) and are commercially available: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxpropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

The cationic protein hydrolysates and protein derivatives are very particularly preferably plant-based.

The cationic polymers are present in the agents according to the invention preferably in amounts of from 0.05 to 10% by weight, based on the total agent. Amounts of from 0.1 to 5% by weight are particularly preferred.

The anionic polymers (G2) are anionic polymers which have carboxylate and/or sulfonate groups. Examples of anionic monomers of which such polymers can consist are acrylic acid, methacrylic acid, crotonic acid, maleic anhydride and 2-acrylamido-2-methylpropanesulfonic acid. Here, the acid groups can be present completely or partially as sodium, potassium, ammonium, mono- or triethanolammonium salt. Preferred monomers are 2-acrylamido-2-methylpropanesulfonic acid and acrylic acid.

Anionic polymers which contain 2-acrylamido-2-methylpropanesulfonic acid as the sole monomer or comonomer, where the sulfonic acid group can be present completely or partially as sodium, potassium, ammonium, mono- or triethanolammonium salt, have proven very particularly effective.

Particular preference is given to the homopolymer of 2-acryl-amido-2-methylpropanesulfonic acid, which is commercially available, for example, under the name Theothik® 11-80.

Within this embodiment, it may be preferred to use copolymers of at least one anionic monomer and at least one nonionogenic monomer. With regard to the anionic monomers, reference is made to the substances listed above. Preferred nonionogenic monomers are acrylamide, methacrylamide, acrylic acid esters, methacrylic acid esters, vinylpyrrolidone, vinyl ether and vinyl ester.

Preferred anionic copolymers are acrylic acid-acrylamide copolymers and in particular polyacrylamide copolymers with monomers containing sulfonic acid groups. A particularly preferred anionic copolymer consists of 70 to 55 mol % of acrylamide and 30 to 45 mol % of 2-acrylamido-2-methylpropanesulfonic acid, where the sulfonic acid group is present completely or partially as sodium, potassium, ammonium, mono- or triethanolammonium salt. This copolymer can also be present in crosslinked form, in which case the crosslinking agents used are preferably polyolefinically unsaturated compounds such as tetraallyloxyethane, allylsucrose, allylpentaerythritol and methylenebisacrylamide. One such polymer is present in the commercial product Sepigel® 305 from SEPPIC. The use of this compound which, besides the polymer component, comprises a hydrocarbon mixture ($C_{13}$-$C_{14}$-isoparaffin) and a nonionogenic emulsifier (laureth-7) has proven particularly advantageous within the scope of the teaching according to the invention.

The sodium acryloyldimethyltaurate copolymers sold under the name Simulgel® 600 as compound with isohexadecane and polysorbate-80 have also proven to be particularly effective according to the invention.

Likewise preferred anionic homopolymers are uncrosslinked and crosslinked polyacrylic acids. Here, allyl ethers of pentaerythritol, of sucrose and of propylene may be preferred crosslinking agents. Such compounds are commercially available, for example, under the trade name Carbopol®.

Copolymers of maleic anhydride and methyl vinyl ether, in particular those with crosslinkages, are likewise color-retaining polymers. A maleic acid-methyl vinyl ether copolymer crosslinked with 1,9-decadienes is commercially available under the name Stabileze® QM.

The anionic polymers are present in the agents according to the invention preferably in amounts of from 0.05 to 10% by weight, based on the total agent. Amounts of from 0.1 to 5% by weight are particularly preferred.

A further very particularly preferred group of polymers are polyurethanes. The polyurethanes consist of at least two different monomer types,
a compound (V1) with at least 2 active hydrogen atoms per molecule and
a di- or polyisocyanate (V2).

The compounds (V1) may, for example, be diols, triols, diamines, triamines, polyetherols and polyesterols. Here, the compounds with more than 2 active hydrogen atoms are usually used only in small amounts in combination with a large excess of compounds with 2 active hydrogen atoms.

Examples of compounds (V1) are ethylene glycol, 1,2- and 1,3-propylene glycol, butylene glycols, di-, tri-, tetra- and poly-ethylene and -propylene glycols, copolymers of lower alkylene oxides, such as ethylene oxide, propylene oxide and butylene oxide, ethylenediamine, propylenediamine, 1,4-diaminobutane, hexamethylenediamine and □,□-diamines based on long-chain alkanes for polyalkylene oxides.

Polyurethanes in which the compounds (V1) are diols, triols and polyetherols may be preferred according to the invention. In particular, polyethylene glycols and polypropylene glycols with molar masses between 200 and 3,000, in particular between 1,600 and 2,500, have proven to be particularly suitable in individual cases.

Polyesterols are usually obtained through modification of the compound (V1) with dicarboxylic acids such as phthalic acid, isophthalic acid and adipic acid.

The compounds (V2) used are predominantly hexamethylene diisocyanate, 2,4- and 2,6-toluene diisocyanate, 4,4'-methylenedi(phenyl isocyanate) and in particular isophorone diisocyanate.

Furthermore, the polyurethanes used according to the invention can also comprise building blocks such as, for example, diamines, as chain extenders and hydroxycarboxylic acids. Dialkylolcarboxylic acids, such as, for example, dimethylolpropionic acid are particularly suitable hydroxycarboxylic acids. As regards the further building blocks, there is no fundamental restriction whether they are nonionic, anionic or cationic building blocks.

As regards further information on the structure and the preparation of the polyurethanes, reference is made expressly to the article in the relevant review works, such as Römpps Chemistry Lexicon and Ullmans Encyclopedia of Industrial Chemistry.

Polyurethanes which have proven particularly suitable according to the invention in many cases are those which can be characterized as follows:
exclusively aliphatic groups in the molecule
no free isocyanate groups in the molecule
polyether and polyester polyurethanes
anionic groups in the molecule.

In some cases, it has likewise proven to be advantageous if the polyurethane does not dissolve in the system, but is stably dispersed.

Furthermore, it has proven advantageous for the preparation of the agents according to the invention if the polyurethanes have not been mixed directly with the other components, but have been introduced in the form of aqueous dispersions. Such dispersions usually have a solids content of about 20-50%, in particular about 35-45% and are also commercially available.

A very particularly preferred polyurethane according to the invention is commercially available under the trade name Luviset® PUR (BASF).

Furthermore, amphoteric polymers (G3) can be used as polymers. The term "amphoteric polymers" is understood as meaning both those polymers which contain both free amino groups and also free —COOH or $SO_3H$ groups in the molecule and are capable of forming internal salts, and also zwitterionic polymers which contain quaternary ammonium groups and —COO$^-$ or —$SO_3^-$ groups in the molecule, and includes those polymers which contain —COOH or $SO_3H$ groups and quaternary ammonium groups.

Like the cationic polymers, amphoteric polymers are likewise very particularly preferred polymers.

One example of an amphopolymer which can be used according to the invention is the acrylic resin available under the name Amphomer®, which is a copolymer of tert-butylaminoethyl methacrylate, N-(1,1,3,3-tetramethylbutyl)acrylamide and two or more monomers from the group acrylic acid, methacrylic acid and monoesters thereof.

Preferably used amphoteric polymers are those polymers which are composed essentially of
(a) monomers with quaternary ammonium groups of the general formula (G3-I)

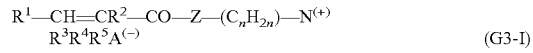

(G3-I)

in which $R^1$ and $R^2$, independently of one another, are hydrogen or a methyl group, and $R^3$, $R^4$ and $R^5$, independently of one another, are alkyl groups having 1 to 4 carbon atoms, Z is an NH group or an oxygen atom, n is an integer from 2 to 5 and $A^{(-)}$ is the anion of an organic or inorganic acid, and
(b) monomeric carboxylic acids of the general formula (G3-II),

(G3-II)

in which $R^6$ and $R^7$, independently of one another, are hydrogen or methyl groups.

These compounds can be used according to the invention either directly and also in salt form, which is obtained through neutralization of the polymers, for example with an alkali metal hydroxide. Very particular preference is given to those polymers in which monomers of type (a) are used in which $R^3$, $R^4$ and $R^5$ are methyl groups, Z is an NH group and $A^{(-)}$ is a halide, methoxysulfate or ethoxysulfate ion; acrylamidopropyltrimethylammonium chloride is a particularly preferred monomer (a). As monomer (b) for the specified polymers, preference is given to using acrylic acid.

Suitable starting monomers are, for example, dimethylaminoethylacrylamide, dimethylaminoethylmethacrylamide, dimethylaminopropylacrylamide, dimethylaminopropylmethacrylamide and diethylaminoethylacrylamide when Z is an NH group, or dimethylaminoethyl acrylate, dimethylaminoethyl methacrylate and diethylaminoethyl acrylate when Z is an oxygen atom.

The monomers containing a tertiary amino group are then quaternized in a known manner, with methyl chloride, dimethyl sulfate or diethyl sulfate being particularly suitable as alkylating reagents. The quaternization reaction can take place in aqueous solution or in the solvent.

Advantageously, those monomers of the formula (G3-l) are used which are derivatives of acrylamide or methacrylamide. Furthermore, preference is given to those monomers which contain halide, methoxysulfate or ethoxysulfate ions as counterions. Preference is likewise given to those monomers of the formula (G3-l) in which $R^3$, $R^4$ and $R^5$ are methyl groups.

Acrylamidopropyltrimethylammonium chloride is a very particularly preferred monomer of the formula (G3-I).

Suitable monomeric carboxylic acids of the formula (G3-II) are acrylic acid, methacrylic acid, crotonic acid and 2-methylcrotonic acid. Preference is given to using acrylic acid or methacrylic acid, in particular acrylic acid.

The zwitterionic polymers that can be used according to the invention are prepared from monomers of the formulae (G3-I) and (G3-II) by polymerization methods known per se. The polymerization can take place either in aqueous or aqueous-alcoholic solution. The alcohols used are alcohols having 1 to 4 carbon atoms, preferably isopropanol, which simultaneously serve as polymerization regulators. However, it is also possible to add other components to the monomer solution as regulators, e.g., formic acid or mercaptans, such as thioethanol and thioglycolic acid. Initiation of the polymerization takes place with the help of radical-forming substances. For this purpose, it is possible to use redox systems and/or thermally decomposing free-radical formers of the azo compound type, such as, for example, azoisobutyronitrile, azobis(cyanopentanoic acid) or azobis(amidinopropane) dihydrochloride. Suitable redox systems are, for example, combinations of hydrogen peroxide, potassium or ammonium peroxodisulfate, and tertiary butyl hydroperoxide with sodium sulfite, sodium dithionite or hydroxylamine hydrochloride as reduction component.

The polymerization can be carried out isothermally or under adiabatic conditions, where the temperature range for the course of the reaction can fluctuate between 20 and 200° C. depending on the concentration ratios as a result of the liberated heat of polymerization, and the reaction optionally has to be carried out under the superatmospheric pressure that is established. Preferably, the reaction temperature is between 20 and 100° C.

The pH during the copolymerization can fluctuate within a wide range. Polymerization is advantageously carried out at low pH values; however, pH values above neutral are also possible. After the polymerization, an aqueous base, e.g., sodium hydroxide solution, potassium hydroxide solution or ammonia, is used to adjust the pH to between 5 and 10, preferably 6 to 8. Further details regarding the polymerization process can be found in the examples.

Those polymers in which the monomers of the formula (G3-I) were present in excess compared with the monomers of the formula (G3-II) have proven to be particularly effective. According to the invention, it is therefore preferred to use such polymers which consist of monomers of the formula (G3-I) and the monomers of the formula (G3-II) in a molar ratio of 60:40 to 95:5, in particular from 75:25 to 95:5.

The amphoteric polymers are present in the agents according to the invention preferably in amounts of from 0.05 to 10% by weight, based on the total agent. Amounts of from 0.1 to 5% by weight are particularly preferred.

Further amphoteric polymers that can be used according to the invention are the compounds specified in the British laid-open specification 2 104 091, the European laid-open specification 47 714, the European laid-open specification 217 274, the European laid-open specification 283 817 and the German laid-open specification 28 17 369. In addition, suitable zwitterionic polymers are methacroylethylbetaine/methacrylate copolymers, which are commercially available under the name Amersette® (AMERCHOL).

In a further embodiment, the agents according to the invention can comprise nonionogenic polymers (G4) as ingredient b).

Suitable nonionogenic polymers are, for example:

Vinylpyrrolidone/vinyl ester copolymers, as are sold, for example, under the trade name Luviskol® (BASF). Luviskol® VA 64 and Luviskol® VA 73, in each case vinylpyrrolidone/vinyl acetate copolymers, are likewise preferred nonionic polymers.

Cellulose ethers, such as hydroxypropylcellulose, hydroxyethylcellulose and methylhydroxypropylcellulose, as are sold, for example, under the trade names Culminal® and Benecel® (AQUALON) and Natrosol® grades (Hercules).

Starch and derivatives thereof, in particular starch ethers, for example Structure® XL (National Starch), a multifunctional, salt-tolerant starch;

Shellac

Polyvinylpyrrolidones, as are sold, for example, under the name Luviskol® (BASF).

Siloxanes. These siloxanes may either be water-soluble or water-insoluble. Both volatile and nonvolatile siloxanes are suitable, with nonvolatile siloxanes being understood as meaning those compounds whose boiling point at atmospheric pressure is above 200° C. Preferred siloxanes are polydialkylsiloxanes, such as, for example, polydimethylsiloxane, polyalkylarylsiloxanes, such as, for example, polyphenylmethylsiloxane, ethoxylated polydialkylsiloxanes, and polydialkylsiloxanes which contain amine and/or hydroxy groups.

Glycosidically substituted silicones.

The nonionic polymers are present in the agents according to the invention preferably in amounts of from 0.05 to 10% by weight, based on the total agent. Amounts of from 0.1 to 5% by weight are particularly preferred.

According to the invention, the term "polymer" is likewise to be understood as meaning special preparations of polymers such as spherical polymer powders. Various methods are known for producing such microbeads from various monomers, e.g., by special polymerization methods or by dissolution of the polymer in a solvent and spraying into a medium in which the solvent can evaporate or diffuse out of the particles. One such method is known, for example, from EP 466 986 B1. Suitable polymers are, for example, polycarbonates, polyurethanes, polyacrylates, polyolefins, polyesters or polyamides. Those spherical polymer powders whose primary particle diameter is below 1 μm are particularly suitable. Such products based on a polymethacrylate copolymer are commercially available, for example, under the trade name Polytrap® Q5-6603 (Dow Corning). Other polymer powders, e.g., based on polyamides (Nylon 6, Nylon 12) are available with a particle size of 2-10 μm (90%) and a specific surface area of about 10 $m^2$/g under the trade name Orgasol® 2002 DU Nat Cos (Atochem S.A., Paris). Further spherical polymer powders which are suitable for the purpose according to the invention are, for example, the polymethacrylates (Micropearl M) from SEPPIC or (Plastic Powder A) from NIKKOL, the styrene-divinylbenzene copolymers (Plastic Powder FP) from NIKKOL, the polyethylene and polypropylene powders (ACCUREL EP 400) from AKZO, or else silicone polymers (Silicone Powder X2-1605) from Dow Corning or else spherical cellulose powders.

The polymer powders described above are present in the agents according to the invention preferably in amounts of from 0.05 to 10% by weight, based on the total agent. Amounts of from 0.1 to 5% by weight are particularly preferred.

Polymers can be characterized irrespective of their chemical structure and charge also according to their function in cosmetic agents. The description of the polymers according to their function in the agents according to the invention does not necessarily correspond to an assessment or significance of these polymers. Rather, all of the polymers are in principle to be regarded as equivalent for the use in the agents according to the invention, even though some of these polymers may be preferred. In addition, some polymers are repeated in two or more descriptions for different effects on account of the polyfunctionality of polymers. Polymers which can bring about two or more desired effects are accordingly particularly preferred for use in the agents according to the invention.

The choice of suitable polymers is also governed by the use of the composition according to the invention. Thus, for example, a film-forming cationic or amphoteric polymer is particularly preferably selected if the composition is to be used as styling composition or setting composition.

Since polymers are often multifunctional, their functions can not always be clearly and unambiguously delimited from one another. In particular, this is true for film-forming and setting polymers. Nevertheless, some film-forming polymers are to be described by way of example. However, at this point, reference is explicitly made to the fact that, for the purposes of the present invention, both film-forming and also setting polymers are essential. Since both properties are also not completely independent of one another, the term "setting polymers" is also always understood as meaning "film-forming polymers," and vice versa.

The preferred properties of the film-forming polymers include film formation. Film-forming polymers are to be understood as meaning those polymers which, upon drying, leave behind a continuous film on the skin, the hair or the nails. Film formers of this type can be used in highly diverse cosmetic products, such as, for example, face masks, make-up, hair-setting compositions, hairsprays, hair gels, hair waxes, hair treatments, shampoos or nail varnishes. Preference is given in particular to those polymers which have adequate solubility in alcohol or water/alcohol mixtures to be present in completely dissolved form in the agent according to the invention during use. On account of their excellent property of film formation, these polymers are very particularly preferred in the agents according to the invention. The use of at least one of these polymers is therefore likewise very particularly preferred according to the invention.

The film-forming polymers may be of synthetic or natural origin.

According to the invention, film-forming polymers are furthermore to be understood as meaning those polymers which, upon use in 0.01 to 20% by weight aqueous, alcoholic or aqueous-alcoholic solution, are capable of depositing a transparent polymer film on the hair. The film-forming polymers here may be anionic, amphoteric, nonionic, permanently cationic or temporarily cationic.

Suitable synthetic, film-forming, hair-setting polymers are homopolymers or copolymers which are composed of at least one of the following monomers: vinylpyrrolidone, vinylcaprolactam, vinyl esters, such as, for example, vinyl acetate, vinyl alcohol, acrylamide, methacrylamide, alkyl- and dialkylacrylamide, alkyl- and dialkylmethacrylamide, alkyl acrylate, alkyl methacrylate, propylene glycol or ethylene glycol, where the alkyl groups of these monomers are preferably C1- to C7-alkyl groups, particularly preferably C1- to C3-alkyl groups.

Homopolymers of vinylcaprolactam, of vinylpyrrolidone or of N-vinylformamide, for example, are suitable. Further suitable synthetic film-forming, hair-setting polymers are, for example, copolymers of vinylpyrrolidone and vinyl acetate, terpolymers of vinylpyrrolidone, vinyl acetate and vinyl propionate, polyacrylamides which are sold, for example, under the trade names Akypomine® P 191 by CHEM-Y, Emmerich, or Sepigel® 305 by Seppic; polyvinyl alcohols, which are sold, for example, under the trade names Elvanol® by Du Pont or Vinol® 523/540 by Air Products, and also polyethylene glycol/polypropylene glycol copolymers, which are sold, for example, under the trade names Ucon® by Union Carbide. Particular preference is given to polyvinylpyrrolidone and polyvinylpyrrolidone/vinyl acetate copolymers.

Suitable natural film-forming polymers are, for example, cellulose derivatives, e.g., hydroxypropylcellulose with a molecular weight of from 30,000 to 50,000 g/mol, which is sold, for example, under the trade name Nisso SI® by Lehmann & Voss, Hamburg.

Examples of customary film formers are *Abies balsamea* (Balsam Canada) resin, Acetylenediurea/Formaldehyde/Tosylamide Crosspolymer, Acrylamide/Ammonium Acrylate Copolymer, Acrylamides Copolymer, Acrylamides/DMAPA Acrylates/Methoxy PEG Methacrylate Copolymer, Acrylamide/Sodium Acrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/Behenyl Methacrylate/Dimethicone Methacrylate Copolymer, Acrylates/t-Butylacrylamide Copolymer, Acrylates Copolymer, Acrylates/Diacetoneacrylamide Copolymer, Acrylates/Dimethicone Copolymer, Acrylates/Dimethicone Methacrylate Copolymer, Acrylates/Dimethiconol Acrylate Copolymer, Acrylates/dimethylaminoethyl Methacrylate Copolymer, Acrylates/Ethyhexyl Acrylate Copolymer, Acrylates/Ethylhexyl Acrylate/HEMA/Styrene Copolymer, Acrylates/Ethylhexyl Acrylate/Styrene Copolymer, Acrylates/Hydroxyesters Acrylates Copolymer, Acrylates/Lauryl Acrylate/Stearyl Acrylate/Ethylamine Oxide Methacrylate Copolymer, Acrylates/octylacrylamide Copolymer, Acrylates/Propyl Trimethicone Methacrylate Copolymer, Acrylates/Stearyl Acrylate/Dimethicone Methacrylate Copolymer, Acrylates/Stearyl Acrylate/Ethylamine Oxide Methacrylate Copolymer, Acrylates/TDI/Trimethylolpropane Copolymer, Acrylates/VA Copolymer, Acrylates/VA Crosspolymer, Acrylates/VP Copolymer, Acrylates/VP/Dimethylaminoethyl Methacrylate/Diacetone Acrylamide/Hydroxypropyl Acrylate Copolymer, Acrylic Acid/Acrylonitrogens Copolymer, Adipic Acid/CHDM/MA/Neopentyl Glycol/Trimellitic Anhydride Copolymer, Adipic Acid/Diethylene Glycol/Glycerin Crosspolymer, Adipic Acid/Diethylenetriamine Copolymer, Adipic Acid/Dilinoleic Acid/Hexylene Glycol Copolymer, Adipic Acid/Dimethylaminohydroxypropyl Diethylenetriamine Copolymer, Adipic Acid/Epoxypropyl Diethylenetriamine Copolymer, Adipic Acid/Fumaric Acid/Phthalic Acid/Tricyclodecane Dimethanol Copolymer, Adipic Acid/isophthalic Acid/Neopentyl Glycol/Trimethylolpropane Copolymer, Adipic Acid/Neopentyl Glycol/Trimellitic Anhydride Copolymer, Adipic Acid/PPG-10 Copolymer, Albumen, Allyl Stearate/VA Copolymer, Aloe Barbadensis Leaf Polysaccharides, Aminoethylacrylate Phosphate/Acrylates Copolymer, Aminoethyl propanediol-Acrylates/Acrylamide Copolymer, Aminoethylpropanediol-AMPD-Acrylates/Diacetoneacrylamide Copolymer, Ammonium Acrylates/Acrylonitrogens Copolymer, Ammonium Alginate, Ammonium Polyacrylate, Ammonium Styrene/Acrylates Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates Copolymer, AMP-Acrylates/Diacetoneacrylamide Copolymer, AMP-Acrylates/Dimethylaminoethylmethacrylate Copolymer, *Astragalus* Gummifer Gum, *Avena sativa* (Oat) Kernel Protein, Behenyl Methacrylate/Perfluorooctylethyl Methacrylate Copolymer, Benzoguanamine/Formaldehyde/Melamine Crosspolymer, Benzoic Acid/Phthalic Anhydride/Pentaerythritol/Neopentyl Glycol/Palmitic Acid Copolymer, Bis-Hydrogenated Tallow Amine Dilinoleic Acid/Ethylenediamine Copolymer, Bis-PEG-15 Dimethicone/IPDI Copolymer, Bis-PPG-15 Dimethicone/IPDI Copolymer, Bis-Stearyl Dimethicone, *Brassica Campestris*/Aleurites Fordi Oil Copolymer, Butadiene/Acrylonitrile Copolymer, 1,4-Butandiol/Succinic Acid/Adipic Acid/HDI Copolymer, Butoxy Chitosan, Butyl Acrylate Crosspolymer, Butyl Acrylate/Ethylhexyl Methacrylate Copolymer, Butyl Acrylate/Hydroxyethyl Methacrylate Copolymer, Butyl Acrylate/Hydroxypropyl Dimethicone Acrylate Copolymer, Butyl Acrylate/Styrene Copolymer, Butylated Polyoxymethylene Urea, Butylated PVP, Butyl Benzoic Acid/Phthalic Anhydride/Trimethylolethane Copolymer, Butylene/Ethylene/Propylene Copolymer, Butyl Ester of Ethylene/MA Copolymer, Butyl Ester of PVM/MA Copolymer, Butylethylpropanediol Dimer Dilinoleate, Butyl Methacrylate/DMAPA Acrylates/Vinylacetamide Crosspolymer, C23-43 Acid Pentaerythritol Tetraester, Calcium Carboxymethyl Cellulose, Calcium Carrageenan, Calcium Potassium Carbomer, Calcium/Sodium PVM/MA Copolymer, C5-6 Alkane/Cycloalkane/Terpene Copolymer, C30-45 Alkyl Dimethicone/Polycyclohexene Oxide Crosspolymer, C1-5 Alkyl Galactomannan, Candelilla Wax Hydrocarbons, Carboxybutyl Chitosan, Carobxymethyl Chitosan, Carboxymethyl Chitosan Succinamide, Carboxymethyl Dextran Carboxymethyl Hydroxyethylcellulose, Castor Oil/IPDI Copolymer, Cellulose acetate, Cellulose Acetate Butyrate, Cellulose Acetate Propionate, Cellulose Acetate Propionate Carboxylate, Cellulose Gum, Cetearyl Dimethicone/Vinyl Dimethicone Crosspolymer, Chitosan, Chitosan Adipate, Chitosan Ascorbate, Chitosan Formate, Chitosan Glycolate, Chitosan Lactate, Chitosan PCA, Chitosan Salicylate, Chitosan Succinamide, C5-6 Olefin/C8-10 Naphtha Olefin Copolymer, Collodion, Copaifera Officinalis (Balsam Copaiba) resin, Copal, Corn Starch/Acrylamide/Sodium Acrylate Copolymer, Corn Starch Modified, C6-14 perfluoroalkylethyl Acrylate/HEMA Copolymer, DEA-Styrene/Acrylates/DVB Copolymer, Dibutylhexyl IPDI, Didecyltetradecyl IPDI, Diethylene glycolamine/Epichlorohydrin/piperazine Copolymer, Diethyhexyl IPDI, Diglycol/CHDM/Isophthalates/SIP Copolymer, Diglycol/Isophthalates/SIP Copolymer, Dihydroxyethyl Tallowamine/IPDI Copolymer, Dilinoleic Acid/Glycol Copolymer Dilinoleic Acid/Sebacic Acid/piperazine/Ethylenediamine Copolymer, Dilinoleyl Alcohol/IPDI Copolymer, Dimethicone PEG-8 Polyacrylate, Dimethicone/Vinyltrimethylsiloxysilicate Crosspolymer, Dimethicone/IPDI Copolymer, Dimethylamine/Ethylenediamine/Epichlorohydrin Copolymer, Dioctyldecyl IPDI, Dioctyldodecyl IPDI, Di-PPG-3 Myristyl Ether Adipate, Divinyldimethicone/Dimethicone Copolymer, Dinvinyldimethicone/Dimethicone Crosspolymer, DMAPA Acrylates/Acrylic Acid/Acrylonitrogens Copolymer, Dodecanedioic Acid/Cetearyl Alcohol/Glycol Copolymer, Ethylcellulose, Ethylene/Acrylic Acid Copolymer, Ethylene/Acrylic Acid/VA Copolymer, Ethylene/Calcium Acrylate Copolymer, Ethylene/MA Copolymer, Ethylene/Magnesium Acrylate Copolymer, Ethylene/Methacrylate Copolymer, Ethylene/Octene Copolymer, Ethylene/Propylene Copolymer, Ethylene/Sodium Acrylate Copolymer, Ethylene/VA Copolymer, Ethylene (Zinc Acrylate Copolymer, Ethyl Ester of PVM/MA Copolymer, *Euphorbia cerifera* (Candelilla) Wax, *Euphorbia cerifera* (Candelilla) Wax Extract, Fibroin/PEG-40/Sodium Acrylate Copolymer, Flexible Collodion, Formaldehyde/Melamine/Tosylamide Copolymer, Galactoarabinan, Glycereth-7 Hydroxystearate/IPDI Copolymer, Glycerin/Phthalic Acid Copolymer Castorate, Glycerin/Succinic Acid Copolymer Castorate, Glyceryl Diricinoleate/IPDI Copolymer, Glyceryl Polyacrylate, Glyceryl Polymethacrylate, Glyceryl Undecyl Dimethicone, Glycidyl C8-11 Acidate/Glycerin/Phthalic Anhydride Copolymer, Glycol Rosinate, Gutta Percha, Hexylene Glycol/Neopentyl Glycol/Adipic Acid/SMDI/DMPA Copolymer, Hydrogenated *Brassica campestris*/Aleurites Fordi Oil Copolymer, Hydrogenated Caprylyl Olive Esters, Hydrogenated Cetyl Olive Esters, Hydrogenated Decyl Olive Esters, Hydrogenated Hexyl Olive Esters, Hydrogenaeted Lauryl Olive Esters, Hydrogenated Myristyl Olive Esters, Hydrogenated Resin, Hydrogenated Styrene/Butadiene Copolymer, Hydrolyzed Candelilla Wax, Hydrolyzed Carnauba Wax, Hydrolyzed Chitosan, Hydrolyzed Gadidae Protein, Hydrolyzed Jojoba Esters, Hydrolyzed Sunflower Seed Wax, Hydrolyzed Wheat Protein, Hydrolyzed Wheat Protein/Cystine Bis-PG-Propyl Silanetriol Copolymer, Hydrolyzed Wheat Protein/Dimethicone PEG-7 Acetate, Hydrolyzed Wheat Protein/Dimethicone PEG-7 Phosphate Copolymer, Hydrolyzed Wheat Protien/PVP Crosspolymer, Hydroxybutyl Methylcellulose, Hydroxyethylcellulose, Hydroxyethyl Chitosan, Hydroxyethyl Ethylcellulose, Hydroxyethyl/Methoxyethyl, Acrylate/Butyl Acrylate Copolymer, Hydroxyethyl/Methoxyethyl Acrylate Copolymer, Hydroxypropylcellulose, Hydroxypropyl Chitosan, Hydroxpropyl Guar, Hydroxypropyl Methylcellulose, Hydroxypropyl Methylcellulose Acetate/Succinate, Hydroxypropyl Oxidized Starch, Hydroxypropyltrimonium Hyaluronate, Hydroxypropyl Xanthan Gum, Isobutylene/Ethylmaleimide/Hydroxyethylmaleimide Copolymer, Isobutylene/MA Copolymer, Isobutylene/Sodium Maleate Copolymer, Isobutylmethacrylate/Bis-Hydroxypropyl Dimethicone Acrylate Copolymer, Isomerized Linoleic Acid, Isophorone Diamine/Cyclohexylamine/Isophthalic Acid/Azelaic Acid Copolymer, Isophoronediamine/Isophthalic Acid/Pentaerythritol Copolymer, Isophorone Diamine/Isophthalic Acid/Trimethylolpropane Copolymer, Isopropyl Ester of PVM/MA Copolymer, 4,4'-Isopropylidenediphenol/Epichlorohydrin Copolymer, Lauryl Acrylate/VA Copolymer, Lauryl Methacrylate/Glycol Dimethacrylate Crosspolymer, Maltodextrin, Mannan, Melia Azadirachta Conditioned Media/Culture, Methoacrylic Acid/Sodium Acrylamidomethyl Propane Sulfonate Copolymer, Methacryloyl Ethyl Betaine/Acrylates Copolymer, Methacryloyl Propyltrimethoxysilane, methoxypolyoxymethylene Melamine, Methyl Ethylcellulose, Methyl Methacrylate/Acrylonitrile Copolymer, Methyl Methacrylate Crosspolymer, Methyl Methacrylate/Glycol Dimethacrylate Crosspolymer, *Myrica Cerifera* (Bayberry) Fruit Wax, Myroxylon Balsamum (Balsam Tolu) Resin, Myroxylon Pereirae (Balsam Peru) Resin, Nitrocellulose, Nylon-12/6/66 Copolymer, Octadecene/MA Copolymer, Octylacrylamide/ Acrylates/Butylaminoethyl Methacrylate Copolymer, Oxymethylene/Melamine Copolymer, Palmitic Acid/Pentaerythritol/Stearic Acid/Terephthalic Acid Copolymer, PEG-150/Decyl Alcohol/SMDI Copolymer, PEG-7 Dimethicone, PEG/PPG-25/25 Dimethicone/Acrylates Copolymer, PEG-150/Stearyl Alcohol/SMDI Copolymer, Pentaerythritol/Terephthalic Acid Copolmer, Pentaerythrityl Cyclohexane Dicarboxylate, perfluorononylethyl Stearyl Dimethicone, Phenylpropyldimethylsiloxysilicate, Phthalic Acid Denatured With Epoxy Resin Alkyd Resin, Phthalic Anhydride/Adipic Acid/Castor Oil/Neopentyl Glycol/PEG-3/Trimethylolpropane Copolymer, Phthalic Anhydride/Benzoic Acid/Glycerin Copolymer, Phthalic Anhydride/Benzoic Acid/Trimethylolpropane Copolymer, Phthalic Anhydride/ Butyl Benzoic Acid/Propylene Glycol Copolymer, Phthalic Anhydride/Glycerin/Glycidyl Decanoate Copolymer, Phthalic Anhydride/Trimellitic Anhydride/Glycols Copolymer, Piperylene/Butene/Pentene Copolymer, Piperylene/ Butene/Pentene/Pentadiene Copolymer, Pistacia Lentiscus (Mastic) Gum, Polianthes Tuberosa Extract, Polyacrylamide, Polyacrylamidomethylpropane Sulfonic Acid, Polyacrylate-1, Polyacrylate-2, Polyacrylate-5, Polyacrylate-6, Polyacrylic Acid, Polyamide-1, Polybeta-Alanine, Polybeta-Alanine/Glutaric Acid Crosspolymer, Polybutyl Acrylate, Polybutylene Terephthalate, Polychlorotrifluoroethylene, Polydiethyleneglycol Adipate/IPDI Copolymer, Polydimethylaminoethyl Methacrylate, Polyester-1, Polyester-2, Polyester-3, Polyethylacrylate, Polyethylene, Polyethylene Naphthalate, Polyethylene Terephthalate, Polyethylglutamate, Polyethylmethacrylate, Polyglucuronic Acid, Polyglyceryl-2 Diisostearate/IPDI Copolymer, Polyisobutene, Polylysine, Polymethacrylamide, Polymethacrylamidopropyltrimonium Methosulfate, Polymethacrylic Acid, Polymethyl Acrylate, Polymethylglutamate, Polymethyl Methacrylate, Polyoxyisobutylene/Methylene Urea Copolymer, Polyoxymethylene Melamine, Polypentaerythrityl Terephthalate, Polypentene, Polyperfluoroperhydrophenanthrene, Poly-p-Phenylene Terephthalamide, Polyphosphorylchloride Glycol Acrylate, Polyquaternium-1, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-43, Polyquaternium-44, Polyquaternium-45, Polyquaternium-46, Polyquaternium-47, Polyquaternium-48, Polyquaternium-49, Polyquaternium-50, Polyquaternium-51, Polyquaternium-56, Polyquaternium-57, Polyquaternium-61, Polysilicone-6, Polysilicone-8, Polysilicone-11, Polysilicone-14, Polystyrene, Polyurethane-1, Polyurethane-2, Polyurethane-4, Polyurethane-5 Polyurethane-6, Polyurethane-7, Polyurethane-8, Polyurethane-10, Polyurethane-11, Polyurethane-12, Polyurethane-13, Polyvinylacetal, Diethylaminoacetate, Polyvinyl Acetate, Polyvinyl Alcohol, Polyvinyl Butyral, Polyvinylcaprolactam, Polyvinyl Chloride, Polyvinyl Imidazolinium Acetate, Polyvinyl Isobutyl Ether, Polyvinyl Laurate, Polyvinyl Methyl Ether, Polyvinyl Stearyl Ether, Potassium Acrylates/Acrylamide, Copolymer, Potassium Acrylates/C10-30 Alkyl Acrylate Crosspolymer, Potassium Acrylates/Ethyhexyl Acrylate Copolymer, Potassium Butyl Ester of PVM/MA Copolymer, Potassium Carbomer, Potassium Carrageenan, Potassium Ethyl Ester of PVM/MA Copolymer, PPG-26/HDI Copolymer, PPG-17/IPDI/DMPA Copolymer, PPG-12/SMDI Copolymer, PPG-7/Succinic Acid Copolymer, PPG-26/TDI Copolymer, PPG-10 Tocophereth-30, PPG-20 Tocophereth-50, Propylene Glycol Diricinoleate/IPDI Copolymer, *Pseudotsuga menziesii* (Balsam Oregon) Resin, Pullulan, PVM/MA Copolymer, PVM/MA Decadiene Crosspolymer, PVP, PVP Montmorillonite, PVP/ VA/Itaconic Acid Copolymer, PVP/VA/Vinyl Propionate Copolymer, Quaternium-22, Rhizobian Gum, Rosin, Rubber Latex, Serum, Albumin, Shellac, Sodium Acrylates/Acrolein Copolymer, Sodium Acrylates/Acrylonitrogens Copolymer, Sodium Acrylates/C10-30 Alkyl Acrylates Crosspolymer, Sodium Acrylates Copolymer, Sodium Acrylate/Vinyl Alcohol Copolymer, Sodium Butyl Ester of PVM/MA Copolymer, Sodium Carbomer, Sodium Carboxymethyl Chitin, Sodium Carboxymethyl Starch, Sodium Carrageenan, Sodium C4-12 Olefin/Maleic Acid Copolymer, Sodium DVB/Acrylates Copolymer, Sodium Ethyl Ester of PVM/ MA Copolymer, Sodium Isooctylene/MA Copolymer, Sodium MA/Diisobutylene Copolymer, Sodium MA/Vinyl Alcohol Copolymer, Sodium PG-Propyldimethicone Thiosulfate Copolymer, Sodium Polyacrylate, Sodium Polymethacrylate, Sodium Polystyrene Sulfonate, Sodium PVM/ MA/Decadiene Crosspolymer, Sodium Styrene/Acrylates Copolymer, Sodium Tauride Acrylates/Acrylic Acid/Acrylonitrogens Copolymer, Starch/Acrylates/Acrylamide Copolymer, Starch Diethylaminoethyl Ether, Stearamidopropyl Dimethicone, Steareth-10, Allyl Ether/Acrylates Copolymer, Stearoyl Epoxy Resin, Stearyl HDI/PEG-50 Copolymer, Stearyl Methacrylate/Perfluorooctylethyl Methacrylate Copolymer, Stearylvinyl Ether/MA Copolymer, *Styrax benzoin* Gum, Styrene/Acrylates/Acrylonitrile Copolymer, Styrene/Acrylates/Ammonium Methacrylate Copolymer, Styrene/Acrylates Copolymer, Styrene/Allyl Benzoate Copolymer, Styrene/DVB Crosspolymer, Styrene/Isoprene Copolymer, Styrene/MA Copolymer, Styrene/Methacrylamide/Acrylates Copolymer, Styrene/Methylstyrene/Indene Copolymer, Styrene/VA Copolymer, Styrene/VP Copolymer, Sucrose Benzoate/Sucrose Acetate Isobutyrate/Butyl Benzyl Phthalate Copolymer Sucrose Benzoate/Sucrose Acetate Isobutyrate/Butyl Benzyl Phthalate/Methyl Methacrylate Copolymer, Sucrose Benzoate/Sucrose Acetate Isobutyrate Copolymer, TEA-Acrylates/Acrylonitrogens Copolymer, TEA-Diricinoleate, TEA-Diricinoleate/IPDI Copolymer, Terephthalic Acid/Isophthalic Acid/Sodium Isophthalic Acid Sulfonate/Glycol Copolymer, Tetradecyloctadecyl Behenate, Tetradecyloctadecyl Myristate, Tetradecyloctadecyl Stearate, Titanium Isostearates, Tosylamide/Epoxy Resin, Tosylamide/Formaldehyde Resin, Tricontanyl PVP, Triethylene Glycol Rosinate, Trimethylol Propane Cyclohexene, Dicarboxylate, Trimethylolpropane Triacrylate, Trimethylpentanediol/Isophthalic Acid/Trimellitic Anhydride Copolymer, Trimethylsiloxysilicate/Dimethiconol Crosspolymer, Trimethylsiloxysilylcarbamoyl Pullulan, *Triticum vulgare* (Wheat) Protein, Tromethamine Acrylates/Acrylonitrogens Copolymer, VA/Butyl Maleate/Isobornyl Acrylate Copolymer, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/Crotonic Acid/PEG-20M Copolymer, VA/DBM Copolymer, VA/Isobutyl Maleate/Vinyl Neodecanoate Copolymer, VA/Vinyl Butyl Benzoate/Crotonates Copolymer, VA/Vinyl Chloride Copolymer, Vinyl Acetate, Vinylamine/Vinyl Alcohol Copolymer, Vinyl Caprolactam/VP/Dimethylaminoethyl Methacrylate Copolymer, Vinyl Chloride/Vinyl Laurate Copolymer, VP/Dimethiconyl-acrylate/Polycarbamyl/Polyglycol Ester, VP/Dimethylaminoethylmethacrylate Copolymer, VP/Dimethylaminoethylmethacrylate/Polycarbamyl Polyglycol Ester, VP/Eicosene Copolymer, VP/Hexadecene Copolymer, VP/Polycarbamyl Polyglycol Ester, VP/VA Copolymer, Welan Gum, Yeast Beta-Glucan, Yeast Polysaccharides, Zein.

Polymers which fix the hair, the setting polymers, contribute to the hold and/or to the build-up in hair volume, hair fullness of the overall hairstyle. Film-forming polymers and gums are therefore generally typical substances of hair treatment agents such as hair-setting compositions, hair foams, hair waxes, hairsprays. As such, they are preferably used in the powders or shaped bodies according to the invention. Substances which furthermore impart hydrophobic properties to the hair are preferred here because they reduce the tendency of the hair to absorb moisture, i.e. water. As a result, the lank hanging down of the hair tresses is reduced and thus a long-lasting construction and retention of the hairstyle is ensured. The test method used for this is often the color retention test. The use of at least one of these polymers in the agents according to the invention is therefore preferred according to the invention. From this group of polymers, very particular preference is given to those which additionally also have setting properties. However, it is also preferred according to the invention if at least one setting and one film-forming polymer are used in the agents according to the invention. It is most preferred if both polymers have both setting and film-forming properties at the same time, albeit possibly to different degrees.

Setting polymers contribute to the hold and/or to the build-up in the hair volume, to the hair fullness of the overall hairstyle. These setting polymers are at the same time also film-forming polymers and therefore generally typical substances of hair treatment agents such as hair-setting compositions, hair foams, hair waxes, hairsprays. Film formation may here be entirely punctiform and join only a few fibers together.

On account of the importance particularly of the setting polymers, these should therefore be listed explicitly in the form of their INCI names. This list of the polymers to be used very particularly preferably according to the invention thus-also includes the cationic polymers.

Examples of customary film-forming, setting polymers are:

Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octyl-acrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMP D-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, *Bacillus*/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octyl-acrylamide/Acrylates/Butylaminoethyl Methacrylate Copolymer, PEG/P PG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terepthalate, Polyester-1, Polyethylacrylate, Polyethylene Terephthalate, Polymethacryloyl Ethyl, Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinyl-formamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10, Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens gum, Terephthalic Acid/Isophthalic Acid/Sodium Isophthalic Acid Sulfonate/Glycol Copolymer, Trimethylolpropane Triacrylate, Trimethylsiloxysilylcarbamoyl, Pullulan, VA/Crotonates Copolymer, VA/Crotonates/Methacryloxybenzophenone-1 Copolymer, VA/Crotonates/Vinyl Nedecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Di methylaminoethyl Methacrylate Copolymer, VP/Acrylates/Lauryl Methacrylate Copolymer, VP/Dimethylaminoethylmethacrylate Copolymer, VP/DMAPA Acrylates Copolymers, VP/Hexadecene Copolymer, VP/VA Copolymer, VP/Vinyl Caprolactam/DMAPA Acrylates Copolymer, Yeast Palmitate.

Very particular preference is given to Acrylates/t-Butylacrylamide Copolymer, Octylacrylamide/Acrylates/Butylaminoethyl Methacrylate Copolymer, Polyurethane-1, Polyvinylcaprolactam and VP/VA Copolymer.

The film-forming and/or setting polymer (A) is present in the agent according to the invention preferably in an amount of from 3.0 to 40 percent by weight, particularly preferably from 3.0 to 30 percent by weight, very particularly preferably in an amount of from 3.0 to 20 percent by weight. It is also possible for a plurality of film-forming and/or setting polymers to be present in the agent according to the invention. Here, these film-forming and/or setting polymers may either be permanently or temporarily cationic, anionic, nonionic or amphoteric. Furthermore, the present invention also encompasses the finding that when using at least two film-forming and/or setting polymers, these can have self-evidently different charges. According to the invention, it may be preferred if an ionic film-forming and/or setting polymer is used together with an amphoteric and/or nonionic film-forming and/or setting polymer. The use of at least two oppositely charged film-forming and/or setting polymers is also preferred. In the latter case, a particular embodiment can in turn additionally comprise at least one further amphoteric and/or nonionic film-forming and/or setting polymer.

Finally, the antistatic effect of polymers is a further function essential for cosmetic agents. With the help of the electric properties of these polymers, the surfaces of the substrates skin, nails and keratin fibers treated with cosmetic agents are influenced in their electric potential. For example, in hair care, the effect referred to as the "fly away effect" and based on the electrostatic repulsion of the hair fibers is reduced in this way. However, the skin feel on the skin surface is also influenced in this way. Some of these polymers develop their optimum effect in a certain pH range. In the agents according to the invention, from this group of polymers, preference is given to those which are at the same time also to be assigned to at least one of the groups of the fixing and/or film-forming polymers. The teaching according to the invention also encompasses the finding that, in the agents according to the invention, in each case at least one antistatic, at least one fixing and at least one film-forming polymer can also be used. However, it is preferred to select the polymers such that at least one of the polymers has at least two of the desired properties. It is most preferred according to the invention if the polymer furthermore fulfills a further property in addition to the three very particularly essential properties setting, fixing and film forming.

Examples of such antistatic polymers are:
Acrylamidopropyltrimonium Chloride/Acrylamide Copolymer, Acrylamidopropyltrimonium Chloride/Acrylates Copolymer, AMP-Isostearoyl Gelatin/Keratin Amino Acids/Lysine Hydroxypropyltrimonium Chloride, Benzyltrimonium Hydrolyzed Collagen, Caesalpinia Spinosa Hydroxypropyltrimonium Chloride, Cocamidopropyldimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Dimethicone Hydroxypropyl Trimonium Chloride, Dimethicone Propylethylenediamine Behenate, Dimethicone Propyl PG-Betaine, Ditallow Dimonium Cellulose Sulfate, Gelatin/Keratin Amino Acids/Lysine Hydroxypropyltrimonium Chloride, Gelatin/Lysin/Polyacrylamide Hydroxypropyltrimonium Chloride, Beta-Glucan Hydroxypropyltrimonium Chloride, Guar Hydroxypropyltrimonium Chloride, Hydrogenated Starch Hydrolysate Hydroxypropyltrimonium Chloride, Hydroxypropyl Guar Hydroxypropyltrimonium Chloride, Hydroxypropyltrimonium Gelatin, Hydroxypropyltrimonium Honey Hydroxypropyltrimonium Hydrolyzed Casein, hydroxypropyltrimonium Hydrolyzed Collagen, Hydroxpropyltrimonium Hydrolyzed Conchiolin Protein, Hydroxypropyltrimonium Hydrolyzed Jojoba Protein, Hydroxypropyltrimonium Hydrolyzed Keratin, Hydroxypropyltrimonium Hydrolyzed Rice Bran Protein, Hydroxypropyltrimonium Hydrolyzed Silk, Hydroxypropyltrimonium Hydrolyzed Soy Protein, Hydroxypropyltrimonium Hydrolyzed Vegetable Protein, Hydroxypropyltrimonium Hydrolyed Wheat Protein, Hydroxypropyltrimonium Hydrolyzed Wheat Protein/Siloxysilicate, Hydroxypropyltrimonium Hydrolyzed Wheat Starch, Hydroxypropyltrimonium Hydrolyzed Whey, Laurdimonium Hydroxypropyl Hydrolyzed Jojoba Protein, Laurdimonium Hydroxypropyl Hydrolyzed Wheat Protein, Laurdimonium Hydroxypropyl Hydrolyzed Wheat Protein/Siloxysilicate, Laurdimonium Hydroxypropyl Hydrolyzed Wheat Starch, Laurdimonium Hydroxypropyl Wheat Amino Acids, Laur/Myrist/Palmitamidobutyl Guanidine Acetate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Oleamidopropyl Dimethylamine Hydrolyzed Collagen, Oleamidopropyldimonim Hydroxypropyl Hydrolyzed Collagen, PEG-2 Coco-Benzonium Chloride, PEG-10, Coco-Benzonium Chloride, PEG-2 Cocomonium Chloride, PEG-15 Cocomonium Chloride, PEG-5 Cocomonium Methosulfate, PEG-15 Cocomonium Methosulfate, PEG-15 Cocopolyamine, PEG-9 Diethylmonium Chloride, PEG-25 Diethylmonium Chloride, PEG-2 Dimeadowfoamamidoethylmonium Methosulfate, PEG-3 Dioleoylamidoethylmonium Methosulfate, PEG-3 Distearoylamidoethylmonium Methosulfate, PEG-4-Distearylethonium Ethosulfate, PEG-2 Hydrogenated Tallow Amine, PEG-5 Hydrogenated Tallow Amine, PEG-8 Hydrogenated Tallow Amine, PEG-10 Hydrogenated Tallow Amine, PEG-15 Hydrogenated Tallow Amine, PEG-20 Hydrogenated Tallow Amine, PEG-30 Hydrogenated Tallow Amine, PEG-40 Hydrogenated Tallow Amine PEG-50 Hydrogenated Tallow Amine, PEG-15 Hydrogenated Tallowmonium Chloride, PEG-5 Isodecyloxypropylamine, PEG-2 Lauramine, PEG-5 Oleamine, PEG-15 Oleamine, PEG-30 Oleamine, PEG-2 Oleammonium Chloride, PEG-15 Oleammonium Chloride, PEG-12

Palmitamine, PEG-8 Palmitoyl Methyl Diethonium Methosulfate, PEG/PPG-1/25 Diethymonium Chloride, PEG-2 Rapeseedamine, PEG-2 Soyamine, PEG-5 Soyamine, PEG-8 Soyamine, PEG-10 Soyamine, PEG-15 Soyamine, PEG-2 Stearamine, PEG-5 Stearamine, PEG-10 Stearamine, PEG-15 Stearamine, PEG-50 Stearamine, PEG-2 Stearmonium Chloride, PEG-15 Stearmonium Chloride, PEG-5 Stearyl Ammonium Chloride, PEG-5 Stearyl Ammonium Lactate, PEG-10 Stearyl Benzonium Chloride, PEG-6 Stearylguanidine, PEG-5 Tallow Amide, PEG-2 Tallow Amine, PEG-7 Tallow Amine, PEG-11 Tallow Amine, PEG-15 Tallow Amine, PEG-20 Tallow Amine, PEG-25 Tallow Amine, PEG-3 Tallow Aminopropylamine, PEG-10 Tallow Aminopropylamine, PEG-15 Tallow Aminopropylamine, PEG-20 Tallow Ammonium Ethosulfate, PEG-5 Tallow Benzonium Chloride, PEG-15 Tallow Polyamine, PEG-3 Tallow Propylenedimonium Dimethosulfate, PG-Hydroxyethylcellulose Cocodimonium Chloride, PG-Hydroxyethylcellulose Lauryldimonium Chloride, PG-Hydroxyethylcellulose Stearyldimonium Chloride, Polymethacrylamidopropyltrimonium Chloride, Polymethacrylamidopropyltrimonium Methosulfate, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13 Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-43, Polyquaternium-44, Polyquaternium-45, Polyquaternium-46, Polyquaternium-48, Polyquaternium-49, Polyquaternium-50, Polyquaternium-54, Polyquaternium-60, Polysilicone-1, Polyvinyl Imidazolinium Acetate, PPG-2 Cocamine, PPG-9 Diethylmonium Chloride, PPG-25 Diethylmonium Chloride, PPG-40 Diethylmonium Chloride, PPG-2 Hydrogenated Tallowamine, PPG-24-PEG-21 Tallowaminopropylamine, PPG-2 Tallowamine, PPG-3 Tallow Aminopropylamine, Propyltrimonium Hydrolyzed Collagen, Propyltrimonium Hydrolyzed Soy Protein, Polytrimonium Hydrolyzed Wheat Protein, Quaternium-8, Quaternium-14, Quaternium-15, Quaternium-16, Quaternium-18, Quaternium-18 Methosulfate, Quaternium-22, Quaternium-24, Quaternium-26, Quaternium-27, Quaternium-30, Quaternium-33, Quaternium-43, Quaternium-45, Quaternium-51, Quaternium-52, Quaternium-53, Quaternium-56, Quaternium-60, Quaternium-61, Quaternium-63, Quaternium-70, Quaternium-71, Quaternium-72, Quaternium-73, Quaternium-75, Quaternium-76 Hydrolyzed Collagen, Quaternium-77, Quaternium-78, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein, Quaternium-80, Quaternium-81, Quaternium-82, Quaternium-83, Quaternium-86, Quaternium-88, Quaternium-89, Quaternium-90, SiliconeQuaternium-2 Panthenol Succinate, Steardimonium Hydroxypropyl Hydrolyzed Casein, Steardimonium Hydroxypropyl Hydrolyzed Collagen, Steardimonium Hydroxypropyl Hydrolyzed Jojoba Protein, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Triethonium Hydrolyzed Collagen Ethosulfate, Trigonella Foenum-Graecum Hydroxypropyltrimonium Chloride, What Germamidopropyldimonium Hydroxypropyl Hydrolyzed Wheat Protein, Wheat Germamidopropyl Epoxypropyldimonium Chloride, Wheatgermamidopropyl Ethyldimonium Ethosulfate.

The emulsion-stabilizing polymers are also types of polymers preferred according to the invention. These are to be understood as meaning polymers which essentially assist the build-up and the stabilization of emulsions (O/W and W/O and multiple emulsions). Surfactants and emulsifiers are the essential constituents, although the stabilizing polymers contribute to a reduction in the coalescence of the emulsified droplets through a positive influence on the continuous or the dispersed phase. This positive influence can be based on electric repulsion, an increase in the viscosity or film formation on the droplet surface. These properties of the polymers in question can also be particularly advantageously used in the compositions according to the invention in order to dissolve the pulverant compositions according to the invention in water before and/or during use of the powder.

Examples of such polymers are Acrylamide/Sodium Acryloyldimethyltaurate Copolymer, Acrylates/Aminoacrylates/C10-30 Alkyl PEG-20 Itaconate Copolymer Acrylates/C10-30 Alkyl Acrylate Crosspolymer, Acrylates/Stearyl Methacrylate Copolymer, Acrylates/Vinyl Isodecanoate Crosspolymer, *Alcaligenes* Polysaccharides, Allyl Methacrylates Crosspolymer, Ammonium Acryloyldimethyltaurate/Beheneth-25 Methacrylate Crosspolymer, Ammonium Acryloyldimethyltaurate/Vinyl Formamide Copolymer, Ammonium Alginate, Ammonium Phosphatidyl Rapeseedate, Ammonium Polyacrylate, Ammonium Polyacryloyldimethyl Taurate, Ammonium Shellacate, Arachidyl Alcohol, *Astragalus* Gummifer Gum, Beeswax, Bentonite, Calcium, Cabroxymethyl Cellulose, Calcium Carrageenan, Calcium Potassium Carbomer, Calcium Starch Octenylsuccinate, $C_{1-5}$ alkyl Galactomannan, C18-38 Alkyl Hydroxystearoyl Stearate, Carbomer, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxylethylcellulose, Chitosan Lauroyl Glycinate, Cholesterol, Cholesterol/HDI/Pullulan Copolymer, Corn Starch/Acrylamide/Sodium Acrylate Copolymer, C12-14 Sec-Pareth-3, C12-14 Sec-Pareth-5, C12-14 Sec-Pareth-7, C12-14 Sec-Pareth-8, C12-14 Sec-Pareth-9, C12-14 Sec-Pareth-12, C12-14 Sec-Pareth-15, C12-14 Sec-Pareth-20, C12-14 Sec-Pareth-30, C12-14 Sec-Pareth-40, C12-14 Sec-Pareth-50, Cyamopsis, Tetragonoloba (Guar) Gum, Dimethicone Crosspolymer, Dimethicone Crosspolymer-2, Dimethicone Ethoxy Glucoside, *Euphorbia cerifera* (Candelilla) Wax, Gellan Gum, Hydrolyzed Beeswax, Hydrolyzed Candelilla Wax, Hydrolyzed Carnauba Wax, Hydrolyzed Collagen PG-Propyl Dimethiconol, Hydrolyzed Sunflower Seed Wax, Hydroxybutyl Methylcellulose, Hydroxyethyl Acrylate/Sodium Acryoyldi methyl Taurate Copolymer, Hydroxyethylcellulose, Hydroxyethyl Ethylcellulose, Hydroxyethyl Isostearyloxy Isopropanolamine, Hydroxypropylcellulose, Hydroxypropyl Cyclodextrin, Hydroxypropyl Guar, Hydroxypropyl Methycellulose, Hydroxypropyl Xanthan Gum, Isopropyl Ester of PVM/MA Copolymer, Lanolin, Lanolin Alcohol, Magnesium Alginate, Maltodextrin, Methoxy PEG-17/Dodecyl Glycol Copolymer, Methoxy PEG-22/Dodecyl Glycol Copolymer, Methylcellulose, Methyl Hydroxyethylcellulose, Microcrystalline Cellulose, Microcrystalline Wax, Montmorillonite, Moroccan Lava Clay, Myrica Cerifera (Bayberry) Fruit Wax, Octadecene/MA Copolymer, Oleic/Linoleic/Linolenic Polyglycerides, Ozokerite, Pectin, PEG-350, PEG-400, PEG-500, PEG-12 Carnauba, PEG-12 Dimethicone Crosspolymer, PEG-22/Dodecyl Glycol Copolymer, PEG-45/Dodecyl Glycol Copolymer, PEG-6 Hydrogenated Palamide, PEG-100/IPDI Copolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG/PPG-20/23 Dimethicone, PEG/PPG-23/6 Dimethicone, PEG/PPG-8/3 Laurate, PEG/PPG-10/3 Oleyl Ether Dimethicone, Polyacrylic Acid, Polyethylene, Polyethylene/Isopropyl Maleate/MA Copolyol, Polyglyceryl-2 Diisostearate/IPDI Copolymer, Polypropylene Terephthalate, Polysilicone-16, Polyvinyl Acetate, Potassium Alginate, Potassium Carbomer, Potassium Carrageenan, Potassium Dextrin Octenylsuccinate, Potassium Polyacrylate, Potassium Undecylenoyl Alginate, Potassium Undecylenoyl Carrageenan, Potassium Undecylenoyl Hydrolyzed Corn Protein, Potassium Undecylenoyl Hydrolyzed Soy Protein, Potassium Undecylenoyl Hydrolyzed Wheat Protein, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-2 Tocophereth-5, PPG-5 Tocophereth-2, PPG-10 Tocophereth-30, PPG-20 Tocophereth-50, PVM/MA Copolymer, PVP, PVP/Decene Copolymer, PVP Montmorillonite, *Pyrus malus* (Apple) Fiber, Saccharated Lime, Sclerotium Gum, Sodium Acrylate/Acryoyldimethyl Taurate Copolymer, Sodium Acrylates/Vinyl Isodecanoate Crosspolymer, Sodium Acrylate/Vinyl Alcohol Copolymer, Sodium Carbomer, Sodium Carboxymethyl Dextran, Sodium Carobxymethyl Starch, Sodium Carrageenan, Sodium Cellulose Sulfate, Sodium C4-12 Olefin/Maleic Acid Copolymer, Sodium Cyclodextrin Sulfate, Sodium Dextrin Octenylsuccinate, Sodium Polyacrylate, Sodium Polyacrylate Starch, Sodium Polyacryoyldimethyl Taurate, Sodium Polymethacrylate, Sodium Polynaphthalenesulfonate, Sodium Polystyrene Sulfonate, Sodium Starch Octenylsuccinate, Sodium/TEA-Undecylenoyl Alginate, Sodium/TEA-Undecylenoyl Carrageenan, Sodium Tocopheryl Phosphate, Starch Hydroxypropyltrimonium Chloride, Stearylvinyl Ether/MA Copolymer, Sterculia Urens Gum, Styrene/MA Copolymer, Sucrose Polypalmate, Synthetic Beeswax, Synthetic Wax, Tamarindus Indica Seed Gum, TEA-Alginate, TEA-Dextrin Octenylsuccinate, Undecylenoyl Inulin, Undecylenoyl Xanthan Gum, Welan Gum, Xanthan Gum, Zinc Undecylenoyl Hydrolyzed Wheat Protein.

Polymers can increase the viscosity of aqueous and non-aqueous phases in cosmetic preparations. In aqueous phases, their viscosity-increasing function is based on their solubility in water or their hydrophilic nature. They are applied in surface-active or else in emulsion-like systems. This property of the polymers too is advantageous in the powders according to the invention before and/or during use.

Some examples of typical polymeric thickeners for aqueous systems are listed below:

Acrylamides Copolymer, Acrylamide/Sodium Acrylate Copolymer, Acrylamide/sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylic Acid/Acrylonitrogens Copolymer, Agar, Agarose, *Alcaligenes* Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, *Astragalus* Gummifer Gum, Attapulgite, *Avena sativa* (Oat) Kernel Flour, Bentonite, Butoxy Chitosan, Caesalpinia Spinosa Gum, Calcium Alginate, Calium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Choleesteryl Hexyl Dicarbamate, Pullulan, Cyamopsis, Tetragonoloba (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acryonitrogens Copolymer, Ethylene/Sodium Acrylate Copolymer, Gelatin, Gellan Gum, Glyceryl Alginate, glycine Soja (Soybean) Flour, Guar, Hydroxpropyltrimonium Chloride, Hectorite, Hydrateed Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxypropyl Starch, Hydroxypropyl Starch Phosphate, Hydroxypropyl Xanthan Gum, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Triolate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethyacrylic Acid, Polyquaternium- 52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, *Solanum tuberosum* (Potato) Starch, Starch/Acrylates/Acrylamide Copolymer, STarch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, *Triticum vulgare* (Wheat) Starch, Tromethamine Acrylates/Acrylonitrogens Copolymer, Tromethamine, Magnesium Aluminum Silicate, Welan Gum, Xanthan Gum, Yeast Beta-Glucan, Yeast Polysaccharides, *Zea mays* (Corn) Starch.

A further way of increasing the viscosity of cosmetic agents is the thickening of the nonaqueous phase, of the lipid phase of the cosmetic agents. For this, use is made of polymers which are not water-soluble but compatible with lipids. They are also used for the gel formation of cosmetic agents with high lipid contents. This likewise makes a significant contribution to the exceptional application of the powders according to the invention. Using these polymers, the viscosity of the composition that forms upon dissolution is regulated in an exceptional manner.

Some of these polymers are listed below:

Acrylates/C10-30 Alkyl Acrylate Crosspolymer, Adipic Acid/PPG-10 Copolymer, Allyl Methacrylates Crosspolymer, Alumina Magnesium Metasilicate, Aluminum Starch Octenylsuccinate, Beeswax, Behenyl Methacrylate/Perfluorooctylethyl Methacrylate Copolymer, Bispolyethylene Dimethicone, Butadiene/Acrylonitrile Copolymer, Butylene/Ethylene Copolymer, Butylene/Ethylene/Styrene Copolymer, Butylene Glycol Montanate, Butyrospermum Parkii (Shea Butter), C29-70 Acid, C23-43 Acid Pentaerythritol Tetraester, C20-24 Alkyl Dimethicone, C24-28 Alkyl Dimethicone, C1-5 Alkyl Galactomannan, C18-38 Alkyl Hydroxystearoyl Stearate, C20-24 Alkyl Methicone, C24-28 Alkyl Methicone, C30-45 Alkyl Methicone, Candelilla Wax Hydrocarbons, C10-30 Cholesterol/Lanosterol Esters, Cellobiose Octanonanoate, Ceresin, Cerotic Acid, Cetearyl Dimethicone/Vinyl Dimethicone Crosspolymer, Chlorinated Paraffin, Cholesterol, Cholesteryl Acetate, Cholesteryl Hydroxystearate, Cholesteryl Isostearate, Cholesteryl Macadamiate, Cholesteryl Stearate, C10-40 Hydroxyalkyl Acid Cholesterol Esters, C10-40 Isoalkyl Acid Cholesterol Esters, C10-40 Isoalkyl Acid Octyldodecanol Esters, C10-40 Isoalkyl Acid Phytosterol Esters, C10-40 Isoalkyl Acid Triglyceride, C30-38 Olefin/isopropyl Maleate/MA Copolymer, Copal, Corn Starch Modified, C6-14 Perfluoroalkylethyl Acrylate/HEMA Copolymer, C6-14 Polyolefin, Decene/Butene Copolymer, Dihydrogenated Tallow Benzylmonium Hectorite, Dilinoleic Acid/Ethylenediamine Copolymer, Dilinoleic Acid/Sebacic Acid. piperazine/Ethylenediamine Copolymer, Dimethicone Crosspolymer, Dimethicone/Phenyl Vinyl Dimethicone Crosspolymer, Dimethicone/Vinyl Dimethicone Crosspolymer, Dimethicone/Vinyltrimethylsiloxysilicate Crosspolymer, Diphenyl Dimethicone/Vinyl Diphenyl Dimethicone/Silsesquioxane Crosspolymer, Divinyldimethicone/Dimethicone Crosspolymer, Dodecanedioic Acid/Cetearyl Alcohol/Glycol Copolymer, Ethylcellulose, Ethylene/Acrylic Acid Copolymer, Ethylene/Acrylic Acid/VA Copolymer, Ethylenediamine/Dimer Tallate Copolymer Bis-Hydrogenated Tallow Amide, Ethylenediamine/Stearyl Dimer Dilinoleate Copolymer, Ethylenediamine/Stearyl Dimer Tallate Copolymer, Ethylene/Octene Copolymer, Ethylene/Propylene Copolymer, Ethylene/Propylene/Styrene Copolymer, *Euphorbia* Cerifera (Candelilla) Wax, Hydrogenated Butylene/Ethylene/Styrene Copolymer, Hydrogenated Ethylene/Propylene/Styrene Copolymer, Hydrogenated Japan Wax, Hydrogenated Polyisobutene, Hydrogenated Styrene/Butadiene Copolymer, Hydrogenated Styrene/Methyl Styrene/Indene Copolymer, Hydroxypropylcellulose, Isobutylene/Isoprene Copolymer, Lithium Oxidized Polyethylene, Methoxy PEG-17/Dodecyl Glycol Copolymer, Methoxy PEG-22/Dodecyl Glycol Copolymer, Methyl Methacrylate Crosspolymer, Methylstyrene/Vinyltoluene Copolymer, Microcrystalline Wax, Montan Acid Wax, Montan Wax, Myrica Cerifera (Bayberry) Fruit Wax, Nylon-611/Dimethicone Copolymer, Octadecene/MA Copolymer, Oleic/Linoleic/Linolenic Polyglycerides, Ouricury Wax, Oxidized Beeswax, Oxidized Microcrystalline Wax, Oxidized Polyethylene, Oxidized Polypropylene, Ozokerite, Paraffin, PEG-18 Castor Oil Dioleate, PEG-10 Dimethicone Crosspolymer, PEG-12 Dimethicone Crosspolymer, PEG-5 Hydrogenated Castor Oil Isostearate, PEG-10 Hydrogenated Castor Oil Isostearate, PEG-20 Hydrogenated Castor Oil Isostearate, PEG-30 Hydrogenated Castor Oil Isostearate, PEG-40 Hydrogenated Castor Oil isostearate, PEG-50 Hydrogenated Castor Oil Isostearate, PEG-58 Hydrogenated Castor Oil Isostearate, PEG-50 Hydrogenated Castor Oil Succinate, PEG-5 Hydrogenated Castor Oil Triisostearate, PEG-10 Hydrogenated Castor Oil Triisostearate, PEG-15 Hydrogenated Castor Oil Triisostearate, PEG-20 Hydrogenated Castor Oil Triisostearate, PEG-15 Hydrogenated Castor Oil Triisostearate, PEG-20 Hydrogenated Castor Oil Triisostearate, PEG-30 Hydrogenated Castor Oil Triisostearate, PEG-40 Hydrogenated Castor Oil Triisostearate, PEG-60 Hydrogenated Castor Oil Triisostearate, PEG-5 Lanolinamide, PEG-5 Oleamide Dioleate, Phthalic Anhydride, Butyl Benzoic Acid/Propylene Glycol Copolymer, Phthalic Anhyddride/Glycerin/Glycidyl, Decanoate Copolymer, Phthalic Anhydride/Trimellitic Anhydride/Glycols Copolymer, Piperylene/Butene/Pentene Copolymer, Polybutene, Polybutylene Terephthalate, Polycyclopentadiene, Polydipentene, Polyethylene, Polyethylene Terephthalate, Polyglyceryl-3, Polyricinoleate, Polyglyceryl-4 Polyricinoleate, Polyglyceryl-5 Polyricinoleate, Polyglyceryl-10 Polyricinoleate, Polyisobutene, Polyisoprene, Polypentene, Polyperfluoroethoxymethoxy, difluoromethyl Distearamide, Polypropylene, Polysilicone-4, Polysilicone-5, Polysilicone-17, Polystyrene, Polyvinyl Butyral, Polyvinyl Laurate, Potassium Oxidized Microcrystalline Wax, Potassium PEG-50 Hydrogenated Castor Oil Succinate, PVM/MA Decadiene Crosspolymer, PVP/Decene Copolymer, *Rhus* Succedanea Fruit Wax, Rosin, Silica Dimethicone Silylate, Silica Dimethyl Silylate, Simmondsia Chinensis (Jojoba) Seed Wax, Sodium PVM/MA/Decadiene Crosspolymer, Spent Grain Wax, Steareth-10 Allyl Ether/Acrylates Copolymer, Steareth-60 Cetyl Ether, Stearoxymethicone/Dimethicone Copolymer, Stearyl Methacrylate/Perfluorooctylethyl Methacrylate Copolymer, Styrene/Methacrylamide/Acrylates Copolymer, Synthetic Beeswax, Synthetic Candelilla Wax, Synthetic Carnaubau, Synthetic Japan Wax, Synthetic Wax, TDI Oxidized Microcrystalline Wax, Tricontanyl PVP, Trifluoropropyl Dimethicone Crosspolymer, Trifluoropropyl Dimethicone/Trifluoropropyl divinyldimethicone Crosspolymer, Trifluoropropyl Dimethicone/Vinyl Trifluoropropyl Dimethicone/Silsesquioxane Crosspolymer, Trimethylpentanediol/Isophthalic Acid/Trimellitic Anhydride Copolymer, Trimethylsiloxysilicate/Dimethiconol Crosspolymer, Vinyl Dimethicone/Lauryl Dimethicone Crosspolymer, Vinyl Dimethicone/Methicone Silsesquioxane Crosspolymer, VP/Eicosene Copolymer, VP/Hexadecene Copolymer.

In the composition according to the invention it is also possible to use microparticles, filled or unfilled, both for achieving certain effects, such as the release of an active ingredient from the capsules, or to achieve particular optical, esthetic effects of the overall formulation. In this case, it may be particularly advantageous if polymers are incorporated as suspension auxiliaries. Suspension auxiliaries facilitate the distribution of solids in liquids. In this process, the polymers coat, through adsorption, the surface of the solid particles and thereby alter the surface properties of these solids. Examples of these polymers are listed below:

Acrylates Copolymer, Acrylates/Methoxy PEG-15 Methacrylate Copolymer, Acrylates/Vinyl Isodecanoate Crosspolymer, Acrylates/VP Copolymer, Acrylic Acid/Acrylamidomethyl Propane Sulfonic Acid Copolymer, Ammonium Styrene/Acrylates Copolymer, Ammonium VA/Acrylates/Sodium Acrylate Copolymer, C6-14 Perfluoroalkylethyl Acrylate/HEMA Copolymer, Diallyloxyneohexyl Zirconium Trideanoate, Dihydrogenated Tallow Benzylmonium Hectorie, Dimethicone Crosspolymer, Dimethiconol/Stearyl Methicone/Phenyl Trimethicone Copolymer, Dimethylol Urea/Phenol/Sodium Phenolsulfonate Copolymer, Disodium Methylene Dinaphthalenesulfonate, Disteardimonium Hectorite, Ethylene/MA Copolymer, Ethylene/VA Copolymer, Ethylhexyl Hydroxystearoyl Hydroxystearate, Hectorite Hydroxyethyl Acrylate/Sodium Acryloyldimethyl Taurate Copolymer, Hydroxyethyl PEI-1000, Hydroxyethyl PEI-1500, Hydroxypropyl Starch, Hydroxypropyltrimonium Maltodextrin Crosspolymer, Isobutylene/MA Copolymer, Isopropyl Ester or PVM/MA Copolymer, Maltodextrin, Methacryloyl Ethyl Betaine/Acrylates Copolymer, Methoxy PEG-17/Dodecyl Glycol Copolymer, Methoxy PEG-22/Dodecyl Glycol Copolymer, Myristoyl/PCA Chitin, Nitrocellulose, PEG-18 Castor Oil Diolelate, PEG-150/Decyl Alcohol/SMDI Copolymer, PEG-12 Dimethicone Crosspolymer, PEG-150/Steary Alcohol/SMDI Copolymer, PEI-7, PEI-10, PEI-15, PEI-30, PEI-45, PEI-250, PEI-275, PEI-700, PEI-1000, PEI-1400, PEI-1500, PEI-1750, PEI-2500, PEI-14M, Perfluorononyl Octyldodecyl Glycol Meadowfloamate, Perlite, Phosphonobutanetricarboxylic Acid, Polyacrylamidomethylpropane Sulfonic Acid, Polycaprolactone, Polyethylacrylate, Polyhydroxystearic Acid, Polyperfluoroethyoxymethoxy PEG-2 Phosphate, Polyvinyl Imidazolinium Acetate, Polyvinyl Methyl Ether, PPG-3 Myristyl Ether Neoheptanoate, PVM/MA Copolymer, PVP, PVP/VA/Itaconic Acid Copolymer, Quaternium-18 Bentonite, Quaternium-18/Benzalkonium Bentonite, Quaternium-18 Hectorite, Quaternium-90 Bentonite, Rhizobian Gum, Silica, Silica Dimethicone Silylate, Silica Dimethyl Silylate, Silica Silylate, Sodium Acrylate/Acryloyldimethyl Taurate Copolymer, Sodium Acrylates/Vinyl Isodecanoate Crosspolymer, Sodium Acrylic Acid/MA Copolymer, Sodium C4-12 Olefin/Maleic Acid Copolymer, Sodium Dextran Sulfate, Sodium Dimaltodextrin Phosphate, Sodium Glycereth-1 Polyphosphate, Sodium Isooctylene/MA Copolymer, Sodium Magnesium Fluorosilicate, Starch Hydroxypropyltrimonium Chloride, Stearalkonium Bentonite, Stearalkonium Hectorite, Stearylvinyl Ether/MA Copolymer, Styrene/Acrylates/Acrylonitrile Copolymer, Styrene/Acrylates/Ammonium Methyacrylate Copolymer, Styrene/MA Copolymer, Sucrose Benzoate/Sucrose Acetate Isobutyrate/Butyl Benzyl Phthalate Copolymer, Tosylamide/Epoxy Resin, Tosylamide/Formaldehyde Resin, VP/Dimethylaminoethylmethacrylate Copolymer, VP/Eicosene Copolymer, VP/Hexadecene Copolymer, VP/VA Copolymer.

It is also possible according to the invention for the preparations used to comprise a plurality, in particular two, different polymers of identical charge and/or in each case one ionic and one amphoteric and/or nonionic polymer.

Further preferred polymers are all polymers which are specified in the "International Cosmetic Ingredient Dictionary and Handbook," (Seventh Edition 1997, The Cosmetic, Toiletry, and Fragrance Association 1101 17th Street, N.W., Suite 300, Washington, D.C. 20036-4702) as polymers in one of the chapters on polymers, such as, for example, "film formers" or "hair fixatives" and are commercially available. Reference is expressly made to this publication and the cited sections therefrom.

In a preferred embodiment, it can be also be advantageous to formulate at least one finishing and/or at least one film-forming, setting polymer and/or at least one thickening polymer. Polymers are to be understood as meaning both natural and synthetic polymers, which may be anionically, cationically, amphoterically charged or nonionic. Thus, the polymer (G) according to the invention can be either a setting and/or film-forming polymer or a polymer with conditioning and/or finishing and/or thickening properties.

The polymers (G) are present in the agents used according to the invention preferably in amounts of from 0.01 to 30% by weight, based on the total agent. Amounts of from 0.01 to 25% by weight, in particular from 0.01 to 15% by weight, are particularly preferred.

The third component of the combination according to the invention is a cosmetic active ingredient. Selection of the active ingredient in question is governed by the desired effect which is to be achieved with the shaped body or the powder. For the shaped body or the powder according to the invention which are to set keratin fibers, are to impart hold, fullness and shine and also ease of styling to the fibers, the active ingredient groups described below are preferably selected according to the invention. According to the invention, at least one active ingredient from at least one active ingredient group is selected for this purpose. It is particularly preferred if at least two further active ingredients are selected from at least two different active ingredient groups. It is particularly preferred if at least three further active ingredients are selected from at least two different active ingredient groups.

The first active ingredient group to be mentioned is fatty substances (D). Fatty substances are to be understood as meaning fatty acids, fatty alcohols, natural and synthetic waxes, which may be present either in solid form or else in liquid form in aqueous dispersion, and to be understood as meaning natural and synthetic cosmetic oil components.

Fatty acids (D1) that can be used are linear and/or branched, saturated and/or unsaturated fatty acids having 6-30 carbon atoms. Preference is given to fatty acids having 10-22 carbon atoms. Among these, mention may be made, for example, of the isostearic acids, such as the commercial products Emersol® 871 and Emersol® 875, and isopalmitic acids, such as the commercial product Edenor® IP 95, and all further fatty acids sold under the trade names Edenor® (Cognis). Further typical examples of such fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroseleic acid, linoleic acid, linolenic acid, elaeostearic acid, arachic acid, gadoleic acid, behenic acid and erucic acid, and technical-grade mixtures thereof which are produced, for example, during the pressurized cleavage of natural fats and oils, during the oxidation of aldehydes from the Roelen oxo synthesis or the dimerization of unsaturated fatty acid. Particular preference is usually given to the fatty acid cuts obtainable from coconut oil or palm oil; the use of stearic acid is generally particularly preferred.

The use amount here is 0.1-5% by weight, based on the total agent. Preferably, the amount is 0.5-10% by weight, where amounts of 1-5% by weight may be very particularly advantageous.

Fatty alcohols (D2) that can be used are saturated, mono- or polyunsaturated, branched or unbranched fatty alcohols with $C_6$-$C_{30}$, preferably $C_{10}$-$C_{22}$ and very particularly preferably $C_{12}$-$C_{22}$ carbon atoms. For the purpose of the invention, decanol, octanol, octenol, dodecenol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, and also Guerbet alcohols thereof may be used, the intention being for this list to be illustrative and nonlimiting in character. However, the fatty alcohols originate from preferably natural fatty acids, in which case it is usually possible to start from an isolation from the esters of the fatty acids by reduction. Those fatty alcohol cuts which are produced by reduction of naturally occurring triglycerides, such as beef tallow, palm oil, peanut oil, rapeseed oil, cottonseed oil, soy oil, sunflower oil and linseed oil, or fatty acid esters arising from their transesterification products with corresponding alcohols, and thus constitute a mixture of different fatty alcohols can likewise be used. Such substances can be acquired commercially, for example, under the names Stenol®, e.g., Stenol® 1618 or Lanette®, e.g., Lanette® O or Lorol®, e.g., Lorol® C8, Lorol® C14, Lorol® C18, Lorol® C8-18, HD-Ocenol®, Crodacol®, e.g., Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. According to the invention it is also possible to use wool wax alcohols, as can be acquired commercially, for example under the names Corona®, White Swan®, Coronet® or Fluilan®. The fatty alcohols are used in amounts of 0.1-30% by weight, based on the total preparation, preferably in amounts of 0.1-20% by weight.

According to the invention, natural or synthetic waxes (D3) that can be used are solid paraffins or isoparaffins, carnauba waxes, beeswaxes, candelilla waxes, ozokerites, ceresin, spermaceti, sunflower wax, fruit waxes such as, for example, apple wax or citrus wax, microwaxes from PE or PP. Such waxes can be obtained, for example, via Kahl & Co., Trittau. The use amount is 0.1-50% by weight, based on the total agent, preferably 0.1-20% by weight and particularly preferably 0.1-15% by weight, based on the total agent.

The natural and synthetic cosmetic oil bodies (D4) include, for example:

vegetable oils. Examples of such oils are sunflower oil, olive oil, soy oil, rapeseed oil, almond oil, jojoba oil, orange oil, wheat germ oil, peach kernel oil and the liquid fractions of coconut oil. Also suitable, however, are other triglyceride oils, such as the liquid fractions of beef tallow, and also synthetic triglyceride oils.

liquid paraffin oils, isoparaffin oils and synthetic hydrocarbons, and di-n-octyl ethers having in total between 12 and 36 carbon atoms, in particular 12 to 24 carbon atoms, such as, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, and di-tert-butyl ether, diisopentyl ether, di-3-ethyldecyl ether, tert-butyl n-octyl ether, isopentyl n-octyl ether and 2-methylpentyl n-octyl ether. The compounds 1,3-di(2-ethylhexyl)cyclohexane (Cetiol® S) and di-n-octyl ether (Cetiol® OE) available as commercial products may be preferred.

ester oils. Ester oils are to be understood as meaning the esters of $C_6$-$C_{30}$-fatty acids with $C_2$-$C_{30}$-fatty alcohols. Preference is given to the monoesters of the fatty acids with alcohols having 2 to 24 carbon atoms. Examples of fatty acid fractions used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid, and technical-grade mixtures thereof which are produced, for example, during the pressurized cleavage of natural fats and oils, in the oxidation of aldehydes from the Roelen oxo synthesis or the dimerization of unsaturated fatty acids. Examples of the fatty alcohol fractions in the ester oils are isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical-grade mixtures thereof which are produced, for example, during the high-pressure hydration of technical-grade methyl esters based on fats and oils or aldehydes from the Roelen oxo synthesis, and as monomer fraction in the dimerization of unsaturated fatty alcohols. According to the invention, particular preference is given to isopropyl myristate (Rilanit® IPM), isononanoic acid C16-18-alkyl esters (Cetiol® SN), 2-ethylhexyl palmitate (Cegesoft® 24), 2-ethylhexyl stearate (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), hexyl laurate (Cetiol® A), di-n-butyl adipate (Cetiol® B), myristyl myristate (Cetiol® MM), cetearyl isononanoates (Cetiol® SN), decyl oleate (Cetiol® V).

dicarboxylic acid esters, such as di-n-butyl adipate, di(2-ethylhexyl) adipate, di(2-ethylhexyl) succinate and diisotridecyl azelate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate, symmetrical, asymmetrical or cyclic esters of carbonic acid with fatty alcohols, for example described in DE-A 197 56 454, glycerol carbonate or dicaprylyl carbonate (Cetiol® CC), trifatty acid esters of saturated and/or unsaturated linear and/or branched fatty acids with glycerol, fatty acid partial glycerides, i.e. monoglycerides, diglycerides and technical-grade mixtures thereof. When using technical-grade products, small amounts of triglycerides may also be present as a result of the preparation. The partial glycerides preferably conform to the formula (D4-I),

in which $R^1$, $R^2$ and $R^3$, independently of one another, are hydrogen or a linear or branched, saturated and/or unsaturated acyl radical having 6 to 22, preferably 12 to 18, carbon atoms, with the proviso that at least one of these groups is an acyl radical and at least one of these groups is hydrogen. The sum (m+n+q) is 0 or numbers from 1 to 100, preferably 0 or 5 to 25. Preferably, $R^1$ is an acyl radical and $R^2$ and $R^3$ are hydrogen and the sum (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachic acid, gadoleic acid, behenic acid and erucic acid, and technical-grade mixtures thereof. Preference is given to using oleic acid monoglycerides.

The use amount of the natural and synthetic cosmetic oil bodies in the agents used according to the invention is usually 0.1-30% by weight, based on the total agent, preferably 0.1-20% by weight, and in particular 0.1-15% by weight.

A final substance group which can be used as fatty substances comprises silicones.

A further substance class which is present as active ingredient in the agents according to the invention as an alternative to those described above is the silicone oils (S). Silicone oils bring about a very wide variety of effects. Thus, they simultaneously influence, for example, the dry and wet combabilities, the feel of the dry and wet hair and also the shine. However, the softness and the elasticity of the film which is formed by film-forming polymers on the hair for the purposes of setting and of styling is also positively influenced by silicones. The term "silicone oils" is understood by the person skilled in the art as meaning several structures of organosilicon compounds. Firstly, they are understood as meaning the dimethiconols (S1). Dimethiconols form the first group of silicones which are particularly preferred according to the invention. The dimethiconols according to the invention may either be linear or branched or cyclic or cyclic and branched. Linear dimethiconols can be depicted by the following structural formula (S1-I):

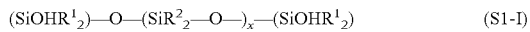

Branched dimethiconols can be depicted by the structural formula (S1-II):

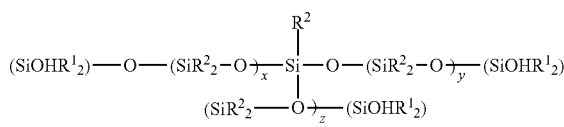

The radicals $R^1$ and $R^2$, independently of one another, are in each case hydrogen, a methyl radical, a C2 to C30 linear, saturated or unsaturated hydrogen radical, a phenyl radical and/or an aryl radical. Nonlimiting examples of the radicals represented by $R^1$ and $R^2$ include alkyl radicals, such as methyl, ethyl, propyl, isopropyl, butyl, isobutyl, pentyl, isopentyl, neopentyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halogen hydrocarbon radicals, such as 3-chloropropyl, 4-bromobutyl, 3,3,3-trifluoropropyl, chlorocyclohexyl, bromophenyl, chlorophenyl and the like, and also sulfur-containing radicals, such as mercaptoethyl, mercaptopropyl, mercaptohexyl, mercaptophenyl and the like; preferably, $R^1$ and $R^2$ is an alkyl radical which contains 1 to about 6 carbon atoms, and most preferably $R^1$ and $R^2$ are methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3$ CC(O)OCH$_2$CH$_2$—, —$C_6H_4C_6H_4$—, —$C_6H_4$—$CH_2C_6H_4$—; and —$(CH_2)_3C(O)SCH_2CH_2$—. Preferably, $R^1$ and $R^2$ are methyl, phenyl and C2 to C22-alkyl radicals. The C2 to C22 alkyl radicals are very particularly preferably lauryl, stearyl and behenyl radicals. The numbers x, y and z are integers and run, in each case independently of one another, from 0 to 50,000. The molecular weights of the dimethicones are between 1,000 D and 10,000,000 D. The viscosities are between 100 and 10,000,000 cPs measured at 25° C. with the help of a glass capillary viscosimeter according to the Dow Corning Corporate Test method CTM 0004 dated Jul. 20, 1970. Preferred viscosities are between 1,000 and 5,000,000 cPs, very particularly preferred viscosities are between 10,000 and 3,000,000 cPs. The most preferred range is between 50,000 and 2,000,000 cPs.

The teaching according to the invention also encompasses that the dimethiconols may already be present as emulsion. Here, the corresponding emulsion of the dimethiconols can be prepared both according to the preparation of the corresponding dimethiconols from these and the customary methods for emulsification known to the person skilled in the art. For this purpose, auxiliaries that can be used for producing the corresponding emulsions may be cationic, anionic, non-ionic or zwitterionic surfactants and emulsifiers as auxiliaries. The emulsions of the dimethiconols can also be prepared directly by an emulsion polymerization process. Such methods are also well known to the person skilled in the art. In this connection, reference may be made, for example, to the "Encyclopedia of Polymer Science and Engineering," Volume 15, Second Edition, pp. 204-308, John Wiley & Sons, Inc. 1989. Reference is expressly made to this standard work.

If the dimethiconols according to the invention are used as emulsion, then the droplet size of the emulsified particles is, according to the invention, 0.01 μm to 10,000 μm, preferably 0.01 to 100 μm, very particularly preferably 0.01 to 20 μm and most preferably 0.01 to 10 μm. The particle size is determined here in accordance with the light-scattering method.

If branched dimethiconols are used, then this is to be understood as meaning that branching is greater than coincident branching which arises by chance as a result of impurities of the particular monomers. For the purposes of the present compound, branched dimethiconols are therefore to be understood as meaning that the degree of branching is greater than 0.01%. Preference is given to a degree of branching greater than 0.1% and very particularly preferably greater than 0.5%. The degree of branching here is determined from the ratio of the unbranched monomers, i.e. the amount of monofunctional siloxane, to the branching monomers, i.e. the amount of tri- and tetrafunctional siloxanes. According to the invention, dimethiconols both with a low degree of branching and also with a high degree of branching may be very particularly preferred.

The following commercial products are specified as examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all of the above-mentioned Chemisil Silicones, Inc.), Dow Corning 1401 Fluid, Dow Corning 1403 Fluid, Dow Corning 1501 Fluid, Dow Corning 1784 HVF Emulsion, Dow Corning 9546 Silicon Elastomer Blend (all of the above-mentioned Dow Corning Corporation), Dub Gel SI 1400 (Stearinerie Dubois Fils), HVM 4852 Emulsion (Crompton Corporation), Jeesilc 6056 (Jeen International Corporation, Lubrasil, Lubrasil DS (both Guardian Laboratories), Nonychosine E, Nonychosine V (both Exsymol), SanSurf Petrolatum-25, Satin Finish (both Collaborative Laboratories, Inc.), Silatex-D30 (Cosmetic Ingredient Resources), Silsoft 148, Silsoft E-50, Silsoft E-623 (all of the above-mentioned Crompton Corporation), SM555, SM2725, SM2765, SM2785 (all of the above-mentioned GE Silicones), Taylor T-Sil CD-1, Taylor TME-4050E (all Taylor Chemical Company), TH V 148 (Crompton Corporation), Tioxgel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all of the above-mentioned Wacker-Chemie GmbH).

The dimethiconols (S1) are in the compositions according to the invention in amounts of from 0.01 to 10% by weight, preferably 0.01 to 8% by weight, particularly preferably 0.1 to 7.5% by weight and in particular 0.1 to 5% by weight, of dimethiconol, based on the composition.

According to the invention, it is also possible that the dimethiconols form their own phase in the compositions according to the invention. In this case, it may be appropriate if the composition is temporarily homogenized by shaking directly prior to use. In this case, the amount of dimethiconol can be up to 40% by weight, preferably in an amount of up to 25% by weight, based on the total composition.

Dimethicones (S2) form the second group of silicones which are particularly preferred according to the invention. The dimethicones according to the invention may either be linear or else branched or else cyclic or cyclic and branched. Linear dimethicones can be depicted by the following structural formula (S2-I):

$(SiR^1_3)-O-(SiR^2_2-O-)_x-(SiR^1_3)$ (S2-I).

Branched dimethicones can be depicted by the structural formula (S2-II):

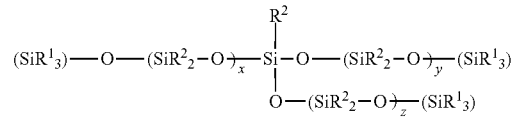

The radicals $R^1$ and $R^2$, independently of one another, are in each case hydrogen, a methyl radical, a C2 to C30 linear, saturated or unsaturated hydrocarbon radical, a phenyl radical and/or an aryl radical. Nonlimiting examples of the radicals represented by $R^1$ and $R^2$ include alkyl radicals, such as methyl, ethyl, propyl, isopropyl, butyl, isobutyl, pentyl, isopentyl, neopentyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halo hydrocarbon radicals, such as 3-chloropropyl, 4-bromobutyl, 3,3,3-trifluoropropyl, chlorocylcohexyl, bromophenyl, chlorophenyl and the like, and sulfur-containing radicals, such as mercaptoethyl, mercaptopropyl, mercaptohexyl, mercaptophenyl and the like; preferably, $R^1$ and $R^2$ is an alkyl radical which contains 1 to about 6 carbon atoms, and most preferably $R^1$ and $R^2$ is methyl.

Examples of $R^1$ include methylene, ethylene, propylene, hexamethylene, decamethylene, $-CH_2CH(CH_3)CH_2-$, phenylene, naphthylene, $-CH_2CH_2SCH_2CH_2-$, $-CH_2CH_2OCH_2-$, $-OCH_2CH_2-$, $-OCH_2-$, $-CH_2CH(CH_3)C(O)OCH_2-$, $-(CH_2)_3CC(O)OCH_2CH_2-$, $-C_6H_4C_6H_4-$, $-C_6H_4-CH_2C_6H_4-$; and $-(CH_2)_3C(O)SCH_2CH_2-$. Preferably, $R^1$ and $R^2$ are methyl, phenyl and C2 to C22-alkyl radicals. The C2 to C22 alkyl radicals are very particularly preferably lauryl, stearyl and behenyl radicals. The numbers x, y and z are integers and run, in each case independently of one another, from 0 to 50,000. The molecular weights of the dimethicones are between 1,000 D and 10,000,000 D. The viscosities are between 100 and 10,000,000 cPs measured at 25° C. with the help of a glass capillary viscosimeter according to the Dow Corning Corporate Test method CTM 0004 dated Jul. 20, 1970. Preferred viscosities are between 1,000 and 5,000,000 cPs, very particularly preferred viscosities are between 10,000 and 3,000,000 cPs. The most preferred range is between 50,000 and 2,000,000 cPs.

The teaching according to the invention also encompasses that the dimethicones may already be present as emulsion. Here, the corresponding emulsion of the dimethicones can be prepared either according to the preparation of the corresponding dimethicones from these and the customary methods for emulsification known to the person skilled in the art. For this, auxiliaries that can be used for producing the corresponding emulsions are cationic, ionic, nonionic or zwitterionic surfactants, and emulsifiers as auxiliaries. The emulsions of the dimethicones can also be prepared directly by an emulsion polymerization method. Such methods are also well known to the person skilled in the art. In this regard, reference may be made, for example, to the "Encyclopedia of Polymer Science and Engineering," Volume 15, Second Edition, pp.

204 to 308, John Wiley & Sons, Inc. 1989. Reference is made expressly to this standard work.

If the dimethicones according to the invention are used as emulsion, then the droplet size of the emulsified particles is, according to the invention, 0.01 μm to 10,000 μm, preferably 0.01 to 100 μm, very particularly preferably 0.01 to 20 μm and most preferably 0.01 to 10 μm. The particle size here is determined by the light-scattering method. If branched dimethicones are used, then these are to be understood as meaning that branching is greater than coincidental branching which arises by chance as a result of impurities of the particular monomers. For the purposes of the present compound, branched dimethicones are therefore to be understood as meaning that the degree of branching is greater than 0.01%. Preference is given to a degree of branching greater than 0.1% and very particularly preferably greater than 0.5%. The degree of branching here is determined from the ratio of the unbranched monomers, i.e. the amount of monofunctional siloxane, to the branching monomers, i.e. the amount of tri- and tetrafunctional siloxanes. According to the invention, dimethicones with both a low degree of branching and also a high degree of branching may be very particularly preferred.

The dimethicones (S2) are in the compositions according to the invention in amounts of from 0.01 to 10% by weight, preferably 0.01 to 8% by weight, particularly preferably 0.1 to 7.5% by weight and in particular 0.1 to 5% by weight, of dimethicones, based on the composition.

According to the invention, it is also possible that the dimethicones form their own phase in the compositions according to the invention. In this case, it may be appropriate if the composition is temporarily homogenized by shaking directly prior to use. In this case, the amount of dimethicone can be up to 40% by weight, preferably in amounts of up to 25% by weight, based on the total composition.

Dimethicone copolyols (S3) form a further group of preferred silicones. Dimethicone copolyols can be depicted by the following structural formulae:

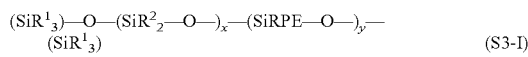
(S3-I)

or by the following structural formula:

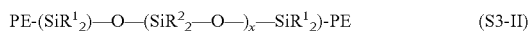
(S3-II)

Branched dimethicone copolyols can be depicted by the structural formula (S3-III):

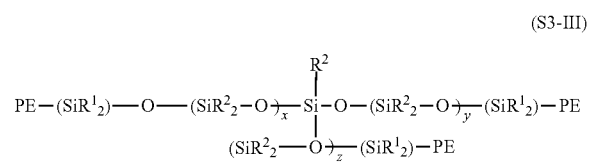
(S3-III)

or by the structural formula (S3-IV):

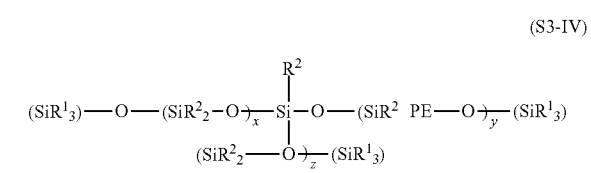
(S3-IV)

The radicals $R^1$ and $R^2$, independently of one another, are in each case hydrogen, a methyl radical, a C2 to C30 linear, saturated or unsaturated hydrocarbon radical, a phenyl radical and/or an aryl radical.

Nonlimiting examples of the radicals represented by $R^1$ and $R^2$ include alkyl radicals, such as methyl, ethyl, propyl, isopropyl, butyl, isobutyl, pentyl, isopentyl, neopentyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halo hydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably, $R^1$ and $R^2$ are an alkyl radical which contains 1 to about 6 carbon atoms, and most preferably $R^1$ and $R^2$ are methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH$ 2-, —$CH_2CH_2OCH_2$—, —$OCH_2CH_2$—, —$OCH_2CH_2CH_2$—, —$CH_2CH(CH_3)C(O)$ $OCH_2$—, —$(CH_2)_3$ $CC(O)OCH_2CH_2$—, —$C_6H_4C_6H_4$—, —$C_6H_4$—$CH_2C_6H_4$—; and —$(CH_2)_3C(O)SCH_2CH_2$—. Preferably, $R^1$ and $R^2$ are methyl, phenyl and C2 to C22-alkyl radicals. The C2 to C22 alkyl radicals are very particularly preferably lauryl, stearyl and behenyl radicals. PE is a polyoxyalkylene radical. Preferred polyoxyalkylene radicals are derived from ethylene oxide, propylene oxide and glycerol. The numbers x, y and z are integers and run, in each case independently of one another, from 0 to 50,000. The molecular weights of the dimethicones are between 1,000 D and 10,000,000 D. The viscosities are between 100 and 10,000,000 cPs measured at 25° C. with the help of a glass capillary viscosimeter according to the Dow Corning Corporate Test method CTM 0004 dated Jul. 20, 1970. Preferred viscosities are between 1,000 and 5,000,000 cPs, very particularly preferred viscosities are between 10,000 and 3,000,000 cPs. The most preferred range is between 50,000 and 2,000,000 cPs.

The teaching according to the invention also encompasses that the dimethicone copolyols may already be present as emulsion. In this connection, the corresponding emulsion of the dimethicone copolyols can be prepared either according to the preparation of the corresponding dimethicone copolyols from these or according to the customary methods for emulsifying known to the person skilled in the art. For this purpose it is possible to use cationic, anionic, nonionic or zwitterionic surfactants and emulsifiers as auxiliaries for preparing the corresponding emulsions. The emulsions of the dimethicone copolyols can also be prepared directly by an emulsion polymerization method. Such methods are also well known to the person skilled in the art. In this regard, reference may be made, for example, to the "Encyclopedia of Polymer Science and Engineering," Volume 15, Second Edition, pp. 204-308, John Wiley & Sons, Inc. 1989. Reference is made expressly to this standard work.

If the dimethicone copolyols according to the invention are used as emulsion, then the droplet size of the emulsified particles is, according to the invention, 0.01 μm to 10,000 μm, preferably 0.01 to 100 μm, very particularly preferably 0.01 to 20 μm and most preferably 0.01 to 10 μm. The particle size here is determined according to the light-scattering method.

If branched dimethicone copolyols are used, then these are to be understood as meaning that the branching is greater than coincidental branching which arises by chance as a result of impurities of the particular monomers. For the purposes of the present compound, branched dimethicone copolyols are therefore to be understood as meaning that the degree of branching is greater than 0.01%. Preference is given to a degree of branching greater than 0.1% and very particularly preferably greater than 0.5%. The degree of branching here is determined from the ratio of unbranched monomers, i.e. the amount of monofunctional siloxane, to the branching monomers, i.e. the amount of tri- and tetrafunctional siloxanes. According to the invention, dimethicone copolyols both with a low degree of branching and also with a high degree of branching may be very particularly preferred.

The dimethicone copolyols (S3) are in the compositions according to the invention in amounts of from 0.01 to 10% by weight, preferably 0.01 to 8% by weight, particularly preferably 0.1 to 7.5% by weight and in particular 0.1 to 5% by weight, of dimethicone copolyol, based on the composition.

According to the invention, it is also possible that the dimethicone copolyols form their own phase in the compositions according to the invention. In this case, the amount of dimethicone copolyol can be up to 40% by weight, preferably in amounts of up to 25% by weight, based on the total composition.

Aminofunctional silicones, also called amodimethicones (S4), are silicones which have at least one (optionally substituted) amino group.

Such silicones can be described, for example, by the formula (S4-I)

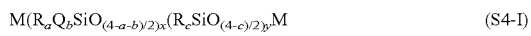  (S4-I)

where, in the above formula, R is a hydrocarbon or a hydrocarbon radical having 1 to about 6 carbon atoms, Q is a polar radical of the general formula —R¹HZ, in which R¹ is a divalent, joining group which is bonded to hydrogen and the radical Z, composed of carbon and hydrogen atoms, carbon, hydrogen and oxygen atoms or carbon, hydrogen and nitrogen atoms, and Z is an organic, aminofunctional radical which contains at least one aminofunctional group; "a" assumes values in the range from about 0 to about 2, "b" assumes values in the range from about 1 to about 3, "a"+"b" is less than or equal to 3, and "c" is a number in the range from about 1 to about 3, and x is a number in the range from 1 to about 2,000, preferably from about 3 to about 50 and most preferably from about 3 to about 25, and y is a number in the range from about 20 to about 10,000, preferably from about 125 to about 10,000 and most preferably from about 150 to about 1,000, and M is a suitable silicone end group, as is known in the prior art, preferably trimethylsiloxy. Nonlimiting examples of the radicals represented by R include alkyl radicals, such as methyl, ethyl, propyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halo hydrocarbon radicals, such as 3-chloropropyl, 4-bromobutyl, 3,3,3-trifluoropropyl, chlorocyclohexyl, bromophenyl, chlorophenyl and the like, and also sulfur-containing radicals, such as mercaptoethyl, mercaptopropyl, mercaptohexyl, mercaptophenyl and the like; preferably, R is an alkyl radical which contains 1 to about 6 carbon atoms, and most preferably R is methyl. Examples of R¹ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$—CH$_6$H$_4$—, —C$_6$H$_4$—CH$_2$C$_6$H$_4$—; and —(CH$_2$)$_3$C(O)SCH$_2$CH$_2$—.

Z is an organic, aminofunctional radical comprising at least one functional amino group. One possible formula for Z is NH(CH$_2$)$_z$NH$_2$, in which z is 1 or more. Another possible formula for Z is —NH(CH$_2$)$_z$(CH$_2$)$_{zz}$NH, in which both z and also zz, independently, are 1 or more, this structure including diamino ring structures such as piperazinyl. Z is most preferably a —NHCH$_2$CH$_2$NH$_2$ radical. Another possible formula for Z is —N(CH$_2$)$_z$(CH$_2$)$_{zz}$NX$_2$ or —NX$_2$, in which each X is selected independently of X$_2$ from the group consisting of hydrogen and alkyl groups having 1 to 12 carbon atoms, and zz is 0.

Q is most preferably a polar, amino-functional radical of the formula —CH$_2$CH$_2$CH$_2$NHCH$_2$CH$_2$NH$_2$. In the formulae, "a" assumes values in the range from about 0 to about 2, "b" assumes values in the range from about 2 to about 3, "a"+"b" is less than or equal to 3, and "c" is a number in the range from about 1 to about 3. The molar ratio of the R$_a$Q$_b$SiO$_{(4-a-b)/2}$ units to the R$_c$SiO$_{(4-c)/2}$ units is in the range from about 1:2 to 1:65, preferably from about 1:5 to about 1:65 and most preferably from about 1:15 to about 1:20. If one or more silicones of the above formula are used, then the various variable substituents in the above formula can be different in the different silicone components which are present in the silicone mixture.

Preferred agents according to the invention are characterized in that they comprise an aminofunctional silicone of the formula (S4-II)

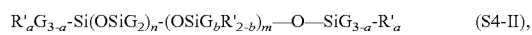  (S4-II), in which:

G is —H, a phenyl group, —OH, —O—CH$_3$, —CH$_3$, —CH$_2$CH$_3$, —CH$_2$CH$_2$CH$_3$, —CH(CH$_3$)$_2$, CH$_2$CH$_2$CH$_2$H$_3$, —CH$_2$CH(CH$_3$)$_2$, —CH(CH$_3$)CH$_2$CH$_3$, —C(CH$_3$)$_3$;

a is a number between 0 and 3, in particular 0;

b is a number between 0 and 1, in particular 1, m and n are numbers whose sum (m+n) is between 1 and 2,000, preferably between 50 and 150, where n preferably assumes values from 0 to 1,999 and in particular from 49 to 149 and m preferably assumes values from 1 to 2,000, in particular from 1 to 10, R' is a monovalent radical selected from

—N(R")—CH$_2$—CH$_2$—N(R")$_2$

—N(R")$_2$

—N$^+$(R")$_3$A$^-$

—N$^+$(R")$_2$A$^-$

—N$^+$H$_2$(R")A$^-$

—N(R")—CH$_2$—CH$_2$—N$^+$R"H$_2$A$^-$, where each R" is identical or different radicals from the group —H, -phenyl, -benzyl, the C$_{1-20}$-alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A an anion which is preferably selected from chloride, bromide, iodide or methosulfate.

Particularly preferred agents according to the invention are characterized in that they contain an aminofunctional silicone of the formula (S4-III)

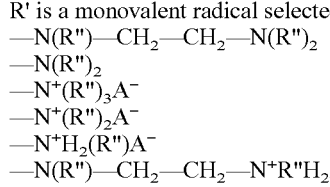  (S4-III)

in which m and n are numbers whose sum (m+n) is between 1 and 2,000, preferably between 50 and 150, where n preferably assumes values from 0 to 1,999 and in particular from 49 to 149 and m preferably assumes values from 1 to 2,000, in particular from 1 to 10.

These silicones are referred to according to the INCI declaration as trimethylsilylamodimethicones.

Particular preference is also given to agents according to the invention which are characterized in that they comprise an aminofunctional silicone of the formula (S4-IV)

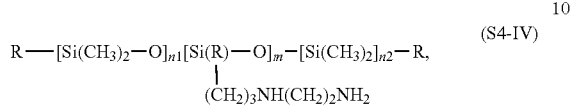
(S4-IV)

in which R is —OH, —O—CH$_3$ or a —CH$_3$ group, and m, n1 and n2 are numbers whose sum (m+n1+n2) is between 1 and 2,000, preferably between 50 and 150, where the sum (n1+n2) preferably assumes values from 0 to 1999 and in particular from 49 to 149 and m preferably assumes values from 1 to 2,000, in particular from 1 to 10.

These silicones are referred to according to the INCI declaration as amodimethicones.

Irrespective of which aminofunctional silicones are used, preference is given to agents according to the invention in which the aminofunctional silicone has an amine number above 0.25 meq/g, preferably above 0.3 meq/g and in particular above 0.4 meq/g. The amine number here is the milliequivalents of amine per gram of the aminofunctional silicone. It can be determined by titration and also quoted in the unit mg of KOH/g.

The amodimethicones (S4) are in the compositions according to the invention in amounts of from 0.01 to 10% by weight, preferably 0.01 to 8% by weight, particularly preferably 0.1 to 7.5% by weight and in particular 0.1 to 5% by weight, of amodimethicone, based on the composition.

It is also possible according to the invention that the amodimethicones form their own phase in the compositions according to the invention. In this case, it may be appropriate if the composition is temporarily homogenized by shaking directly prior to use. In this case, the amount of amodimethicone can be up to 40% by weight, preferably in amounts of up to 25% by weight, based on the total composition.

Only recently, completely new types of polyammonium-polysiloxane compounds have become known in which the siloxane substructures are joined together optionally via ammonium substructures. Such compounds and their use in cosmetic agents are described, for example, in the laid-open specification WO 02/10257.

As silicone, the compositions according to the invention can comprise at least one polyammonium-polysiloxane compound, which is composed as described below. The polyammonium-polysiloxane compounds contain:

a) at least one polyalkylene oxide structural unit of the general formulae:

-A-E-, -E-A-, -A-E-A'- and/or -A'-E-A-, in which:

A is one of the groups: —CH$_2$C(O)O—, —CH$_2$CH$_2$C(O)O—, —CH$_2$CH$_2$CH$_2$C(O)O—, —OC(O)CH$_2$—, —OC(O)CH$_2$CH$_2$— and/or —OC(O)CH$_2$CH$_2$CH$_2$—, A' is: —CH$_2$C(O)—, —CH$_2$CH$_2$C(O)—, —CH$_2$CH$_2$CH$_2$C(O)—, —C(O)CH$_2$—, —C(O)CH$_2$CH$_2$— and/or —C(O)CH$_2$CH$_2$CH$_2$— and E is a polyalkylene oxide group of the general formulae:

where q=1 to 200 and r=0 to 200, where the terminal oxygen atom of group A bonds to the terminal —CH$_2$ group of group E, and the terminal carbonyl carbon atom of group A' bonds to the terminal oxygen atom of group E, in each case to form ester groups, and/or at least one terminal polyalkylene oxide structural unit of the formula -A-E-R$^2$, in which A and E have the meaning specified above, and R$^2$ is H, straight-chain, cyclic or branched C$_1$-C$_{20}$-hydrocarbon radical which may be interrupted by —O—, or —C(O) and substituted by —OH and may be acetylenic, olefinic or aromatic, a2) at least one divalent or trivalent organic radical which contains at least one ammonium group, a3) at least one polysiloxane structural unit of the general formula:

in which S is —Si(R$^1$)$_2$—O[—Si(R$^1$)$_2$—O]$_n$—Si(R$^1$)$_2$— and in which R$^1$ is C$_1$-C$_{22}$-alkyl, C$_1$-C$_{22}$-fluoroalkyl or aryl, n is 0 to 1,000, and if two or more groups S are present in the polysiloxane compound, these may be identical or different, in which K is a divalent or trivalent straight-chain, cyclic or branched C$_2$-C$_{40}$-hydrocarbon radical which may be interrupted by —O—, —N—, —NR$^1$—, —C(O)—, —C(S)—, —N$^+$(R$^3$)— and —N$^+$(R$^1$)(R$^3$) and substituted by —OH, in which R$^1$ is as defined above, or optionally represents a bond to a divalent radical R$^3$, and in which R$^3$ is a monovalent or divalent straight-chain, cyclic or branched C$_1$-C$_{20}$-hydrocarbon radical which may be substituted by —O—, —NH—, —C(O)—, —C(S)— and substituted by —OH, or is -A-E-R$^2$, in which A, E and R is as defined above, where the radicals K may be identical or different from one another, and in the case when K is a trivalent radical, saturation of the third valence takes place via a bond to the above-mentioned organic radical which contains at least one ammonium group, a4) an organic or inorganic acid radical for neutralizing the charges resulting from the ammonium group(s).

The polysiloxane compounds according to the invention are characterized in that they have the above defined components a1) to a4). The polysiloxane compounds are formed here by joining the specified structural units or radicals a1) to a3) to one another. Component a4) serves to neutralize the positive charges resulting from component a2).

The polysiloxane compounds according to the invention may be oligomers or polymeric compounds. Oligomeric compounds here also include the case described below in which the polysiloxane compound has just one repeat unit.

Polymeric polysiloxane compounds according to the invention are naturally formed through alternate linking of divalent radicals.

In the case of the polymeric polysiloxane compounds according to the invention, the terminal atom groups result from the terminal atom groups of the starting materials used. This is known per se to the person skilled in the art.

In a preferred embodiment, the polymeric polysiloxane compounds according to the invention are linear polyammonium-polysiloxane compounds composed of the structural components a1) to a3). Thus, the linear polymeric polysiloxane compounds according to the invention, particularly their linear polymer main chain formed from the repeat units, can be built up by alternately stringing together polyalkylene oxide structural units a1), organic radicals which contain at least one, preferably quaternary ammonium group a2) and polysiloxane structural units a3). This means that the free valences moreover optionally present in the structural components (as can arise in the case of trivalent radicals as component a2) or in the case of trivalent radicals K) preferably do not serve to build up polymeric side chains and/or polymeric branches.

In a further embodiment, the main chain of the linear polymeric polysiloxane compounds according to the invention can be constructed from the organic radicals which contain at least one ammonium group a2) and the polysiloxane structural units a3), and the polyalkylene oxide structural units a1) bind as side chains to the trivalent organic ammonium group radical.

Thus, the following structures, for example, can result:
(polyalkylene oxide structural unit-polysiloxane structural unit-polyalkylene oxide structural unit—preferably quaternary ammonium group radical)$_x$
(polysiloxane structural unit—preferably quaternary ammonium group radical)$_x$—polyalkylene oxide structural unit)$_x$—

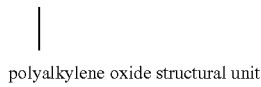

Depending on the molar ratio of the monomeric starting compounds, polysiloxane compounds according to the invention can result which have just one repeat unit. This is known per se to the person skilled in the art. This case leads, for example, to polysiloxane compounds according to the invention with the structure:
(terminal polyalkylene oxide structural unit-quaternary ammonium group radical-polysiloxane structural unit-quaternary ammonium group radical-terminal polyalkylene oxide structural unit).

The polysiloxane compounds according to the invention preferably consist essentially of components a1) to a4), where the polymeric polysiloxane compounds according to the invention naturally have the terminal groups resulting from the reaction of the monomeric starting materials. It is also possible, however, to use monofunctional chain terminators.

The polyalkylene oxide structural units a) may be divalent radicals of the general formulae:

-A-E-, -E-A-, -A-E-A' and/or -A'-E-A.

Here, the radical A is:
—$CH_2C(O)O$—, —$CH_2CH_2C(O)O$—, —$CH_2CH_2CH_2C(O)O$—, —$OC(O)CH_2$—, —$OC(O)CH_2CH_2$— and/or —$OC(O)CH_2CH_2CH_2$—.

The radical A' here is:
—$CH_2C(O)$—, —$CH_2CH_2C(O)$—, —$CH_2CH_2CH_2C(O)$—, —$C(O)CH_2$—, —$C(O)CH_2CH_2$— and/or —$C(O)CH_2CH_2CH_2$—

The polyalkylene oxide group E of the general formulae:
—$[CH_2CH_2O]_q$—$[CH_2CH(CH_3)O]_r$— and/or —$[OCH(CH_3)CH_2]_r$—$[OCH_2CH_2]_q$ where q=1 or 2 to 200 and r=0 to 200 include here all possible ethylene oxide/propylene oxide groups. They may also be random ethylene oxide/propylene oxide copolymer groups or ethylene oxide/propylene oxide block copolymer groups with an arbitrary arrangement of one or more ethylene oxide blocks or propylene oxide blocks.

The binding of the radicals A and A' to the group E takes place such that the terminal oxygen atom of group A bonds to the terminal —$CH_2$ group of group E, and the terminal carbonyl carbon atom of group A' bonds to the terminal oxygen atom of group E, in each case with formation of ester groups.

The polyalkylene oxide structural units a1) may furthermore be monovalent, i.e. terminal polyalkylene oxide structural unit of the formula -A-E-$R^2$, in which A and E have the meaning given above, and $R^2$ is H, straight-chain, cyclic or branched $C_1$-$C_{20}$-hydrocarbon radical which may be interrupted by —O— or —C(O)— and substituted by —OH and be acetylenic, olefinic or aromatic.

Component a2) of which the polysiloxane compounds according to the invention are composed is at least one divalent or trivalent organic radical which contains at least one ammonium group. The bonding of the radical to the other components of the polysiloxane compounds according to the invention preferably takes place via the nitrogen atom of one or more ammonium groups in the organic radical. The terms "divalent" or "trivalent" mean that the organic ammonium radical has two or three free valences for forming bonds in particular to the other components of the polysiloxane compounds according to the invention. The ammonium radical is expediently depicted by an $NH_4^+$ group in which at least two hydrogen atoms are substituted by organic groups. It is preferably a secondary or quaternary, particularly preferably a quaternary, ammonium group. According to the general definition (see e.g., Römpp Chemistry Lexikon), a quaternary ammonium group is a group in which all four hydrogen atoms of an $NH_4^+$ group are replaced by organic radicals.

Component a2) of the polysiloxane compounds according to the invention is at least one polysiloxane structural unit of the general formula:

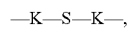

S here is a polysiloxane group of the general formula —Si$(R^1)_2$—O[—Si$(R^1)_2$—O]$_n$—Si$(R^1)_2$—,
in which $R^1$ is $C_1$-$C_{22}$-alkyl, $C_1$-$C_{22}$-fluoroalkyl or aryl, preferably phenyl, n=0 to 1,000, and if two or more groups S are present in the polysiloxane compound, these may be identical or different.

$R^1$ is preferably $C_1$-$C_{18}$-alkyl, $C_1$-$C_{18}$-fluoroalkyl and aryl. Furthermore, $R^1$ is preferably $C_1$-$C_{18}$-alkyl, $C_1$-$C_6$-fluoroalkyl and aryl. Furthermore, $R^1$ is preferably $C_1$-$C_6$-alkyl, $C_1$-$C_6$-fluoroalkyl, more preferably $C_1$-$C_4$-fluoroalkyl, and phenyl. Even more preferably, $R^1$ is methyl, ethyl, trifluoropropyl and phenyl.

For the purposes of the present invention, the term "$C_1$-$C_{22}$-alkyl" means that the aliphatic hydrocarbon groups have 1 to 22 carbon atoms which may be straight-chain or branched. By way of example, methyl, ethyl, propyl, n-butyl, pentyl, hexyl, heptyl, nonyl, decyl, undecyl, isopropyl, neopentyl and 1,2,3-trimethylhexyl may be listed.

For the purposes of the present invention, the term "$C_1$-$C_{22}$-fluoroalkyl" means aliphatic hydrocarbon compounds having 1 to 22 carbon atoms which may be straight-chain or branched and are substituted by at least one fluorine atom. By way of example, monofluoromethyl, monofluoroethyl, 1,1,1-trifluoroethyl, perfluoroethyl, 1,1,1-trifluoropropyl, 1,2,2-trifluorobutyl may be listed.

For the purposes of the present invention, the term "aryl" means unsubstituted phenyl or phenyl substituted one or more times by OH, F, Cl, $CF_3$, $C_1$-$C_6$-alkyl, $C_1$-$C_6$-alkoxy, $C_3$-$C_7$-cycloalkyl, $C_2$-$C_6$-alkenyl or phenyl. The expression can optionally also mean naphthyl.

K is a divalent or trivalent straight-chain, cyclic or branched $C_2$-$C_{40}$-hydrocarbon radical which can be interrupted by —O—, —NH—, —N—, C(O)—, —C(S)—, —N$^+$(R$^3$)—, —NR$^1$—, and —N$^+$(R$^1$)R$^3$)— and substituted by —OH.

"Interrupted" means here that in the case of the divalent radicals, a —CH$_2$— group, in the case of the trivalent radicals a —CH— group of the hydrocarbon radical are replaced by said groups. This is also true for the remainder of the description whenever this designation is used.

The group K bonds to the silicon atom of the group S via a carbon atom.

The group K can, as can be seen above, likewise have preferably quaternary ammonium groups, meaning that ammonium groups in addition to the ammonium groups in said component a2) result in the polysiloxane compounds according to the invention.

The polysiloxane compounds according to the invention can have amino groups, such as, for example, in the radical K. The reaction of the polysiloxane compounds according to the invention with acids leads to their protonation. Such protonated polysiloxane compounds having amino groups are encompassed within the scope of the present invention.

The bonding of component a3), the polysiloxane structural unit —K—S—K—, to the remaining structural components via the radical K preferably does not take place via a nitrogen atom of the radical K.

R$^1$ is as defined above or optionally represents a bond to a divalent radical R$^3$, resulting in a cycle.

R$^3$ is a monovalent or divalent straight-chain, cyclic or branched C$_1$-C$_{20}$-hydrocarbon radical which may be interrupted by —O—, —NH—, —C(O)—, —C(S)— and substituted by —OH, or is -A-E-R$^2$, in which A, E and R$^2$ are as defined above.

The radicals K can be identical or different from one another, and when K is a trivalent radical, saturation of the third valence takes place via a bond to the above-mentioned organic radical which contains at least one ammonium group.

The polysiloxane compounds according to the invention furthermore comprise the component a4), at least one organic or inorganic anionic acid radical for neutralizing the charges resulting from the ammonium group(s). Organic or inorganic acid radicals are radicals which result formally from the cleavage of one or more protons from organic or inorganic acids and include, for example, halides, such as fluoride, chloride, bromide, sulfates, nitrates, phosphates, carboxylates, such as formiate, acetate, propionate etc., sulfonates, sulfates, polyether carboxylates and polyether sulfates etc. Preference is given to chloride. The organic or inorganic anionic acid radicals as component a4) of the polysiloxane compounds according to the invention may be identical or different from one another. Thus, the reaction of the amines with alkyl halides preferentially results in halide ions, whereas, for example carboxylates result from the carboxylic acids which can be added during the reaction of bisepoxides with amines.

In a preferred embodiment of the polysiloxane compounds according to the invention, K is a divalent or trivalent straight-chain, cyclic or branched C$_2$-C$_{40}$-hydrocarbon radical which can be interrupted by —O—, —NH—, —N—, —NR$^1$—, —C(O)—, —C(S)— and substituted by —OH, in which R$^1$ is as defined above, and where the radicals K may be identical or different from one another.

The above-mentioned organic radical which contains at least one preferably quaternary ammonium group is preferably a radical of the general formula:

—N$^1$—F—N$^1$—, in which N$^1$ is a quaternary ammonium group of the general formula —(R$^4$)N$^+$(R$^5$)—, in which R$^4$ is a monovalent or divalent straight-chain, cyclic or branched C$_1$-C$_{20}$-hydrocarbon radical which can be interrupted by —O—, —NH—, —C(O)—, —C(S)— and substituted by —OH, and R$^5$ is a monovalent straight-chain, cyclic or branched C$_1$-C$_{20}$-hydrocarbon radical which can be interrupted by —O—, —NH—, —C(O)—, —C(S)— and substituted by —OH, or is a single bond to a divalent radical R$^4$ or a tetravalent radical F, and the radicals R$^4$ and R$^5$ within the group —N$^1$—F—N$^1$— and in the polysiloxane compound can be identical or different from one another, F is a divalent or tetravalent straight-chain, cyclic or branched C$_2$-C$_{30}$-hydrocarbon radical which can be interrupted by —O—, —NH—, —N—, —C(O)—, —C(S)—, a siloxane chain S where the above-mentioned preferences apply for S, and substituted by —OH.

As regards further details of the definitions of the quaternary ammonium group of the formula —N$^1$—F—N$^1$— (preferred embodiment etc.) reference may be made to the explanations of the first embodiment of the present invention with regard to component a, the polyammonium-polysiloxane compounds in which this group is realized, and which also have validity in this more general context.

The above-mentioned organic radical which contains at least one preferably quaternary ammonium group can furthermore preferably be a radical of the general formula —(R$^6$)N$^+$(R$^7$)—, in which R$^6$ is a monovalent or divalent straight-chain, cyclic or branched C$_1$-C$_{30}$-hydrocarbon radical which can be interrupted by —O—, —NH—, —C(O)—, —C(S)— and substituted by —OH, or R$^6$ is a single bond to a trivalent radical K.

R$^7$ is a monovalent straight-chain, cyclic or branched C$_1$-C$_{20}$-hydrocarbon radical which can be interrupted by —O—, —NH—, —C(O)—, —C(S)— and substituted by —OH, or -A-E-R$^2$, in which -A-E-R$^2$ has the meaning given above, or a single bond to a divalent radical R$^6$ or to a trivalent radical K.

The radicals R$^6$ and R$^7$ may be identical or different from one another.

As regards further details of the definitions of the quaternary ammonium group of the formula —(R$^6$)N$^+$(R$^7$)— (preferred embodiments), reference may be made to the explanations of the second, third and fourth embodiment regarding the polyammonium-polysiloxane compounds, the constituent a), of the present active ingredient complex according to the invention in which this group is realized and which also have validity in this more general context.

The above-mentioned organic radical which contains at least one ammonium group can furthermore preferably be a radical of the general formula:

—N$^5$—F$^1$—N$^5$—, in which N$^5$ is an ammonium group of the general formula

—(R$^{23}$)N$^+$(R$^{24}$)—, wherein

R$^{23}$ is hydrogen, a monovalent or divalent straight-chain, cyclic or branched C$_1$-C$_{20}$-hydrocarbon radical which can be interrupted by —O—, —NH—, —C(O)—, —C(S)— and substituted by —OH, R$^{24}$ is a hydrogen, a monovalent straight-chain, cyclic or branched C$_1$-C$_{20}$ hydrocarbon radical which can be interrupted by —O—, —NH—, —C(O)—, —C(S) and substituted by OH, or is a single bond to a divalent radical R$^{23}$, and the radicals $R^{23}$ and $R^{24}$ within the group $-N^5-F^1N^5-$ and also in the polysiloxane compound may be identical or different from one another, $F^1$ is a divalent straight-chain, cyclic or branched —N hydrocarbon radical which can be interrupted by —O—, —NH—, —C(O)—, —N—, —C(S)— or by a group -E-, and in which a majority of the groups $N^5$ and $F^1$ can in each case be identical to or different from one another.

As regards further details of the definitions of the ammonium group of the formula $-N^5-F^1-N^5-$(preferred embodiments), reference may be made to the explanations of the fifth embodiment regarding component a, the polyammonium-polysiloxane compounds of the present invention, in which this group is realized by way of example and which also have validity in this more general context.

In the text below, the components a) of the active ingredient complex according to the invention, the polyammonium-polysiloxane compounds, are described in more detail by reference to five preferred embodiments of these compounds.

One particular embodiment of the polyammonium-polysiloxane compounds (which is referred to below as the first embodiment of component a) of the active ingredient complex), in which the above-mentioned organic radical which contains at least one preferably quaternary ammonium group as component a2) of the polysiloxane compounds according to the invention constitutes a radical of the general formula:

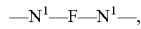

is represented by the polysiloxane compounds of the following general formula (I):

$$-[B-N^1-F-N^1]_m \quad (1)$$

in which m=2 to 500,

B is -A-E-K—S—K-E-A- and additionally optionally -A-E-A'- or -A'-E-A-, in which S, K, -A-E-, -E-A-, -A-E-A'- and -A'-E-A- and $-N^1-F-N^1-$ are as defined above, and the fraction of the group -A-E-A'- or -A'-E-A- in the group B can be chosen such that the mass of -A-E-A'- or -A'-E-A- is from 0 to 90%, preferably 0% or 0.1 to 50% of the mass of the polysiloxane fraction S in the polymer.

The first embodiment of the polyammonium-polysiloxane compounds is preferably linear alkylene oxide-modified polyquaternary polysiloxanes of the general formula (I'), $$-[B-N^1-F-N^1]_m- \quad (I')$$

in which m is 2 to 500,
B is -A-E-K—S—K-E-A-,
S is $-Si(R^1)_2-O[Si(R^1)_2-O]_n-Si(R^1)_2$
$R^1$ is $C_1-C_{22}$-alkyl, $C_1-C_{22}$-fluoroalkyl or aryl,
n is 0 to 1,000,
K is a divalent, straight-chain, cyclic or branched $C_2-C_{20}$-hydrocarbon radical which can be interrupted by —O—, —NH—, $-NR^1-$, —C(O)—, —C(S) and substituted by —OH,
E is a polyalkylene oxide unit of the structure

q is 1 to 200,
r is 0 to 200 and
A is $-CH_2C(O)O-$, $-CH_2CH_2C(O)O-$ or $-CH_2CH_2CH_2C(O)O-$,
$N^1$ is a quaternary ammonium structure $-(R^4)N^+(R^5)-$
$R^4$ is a monovalent or divalent straight-chain, cyclic or branched $C_1-C_{20}$-hydrocarbon radical which can be interrupted by —O—, —NH—, —C(O)—, —C(S)— and substituted by —OH,
$R^5$ is $R^4$ or a single bond to $R^4$ or F, F is a divalent or tetravalent straight-chain, cyclic or branched $C_2-C_{30}$-hydrocarbon radical which can be interrupted by —O—, —NH—, —N—, —C(O)—, —C(S)—, a siloxane chain S, where the preferences specified above apply for S, and substituted by —OH.

The possibility of a tetravalent substructure for F means that F can form a branched or ring system with the bordering $N^1$, so that F is then involved with, in each case, two bonds in the quaternization of both bordering $N^1$. For further illustration, reference may be made to the laid-open specification WO 02/10257, in particular Example 1 therein.

In a further embodiment of the polyammonium-polysiloxane compounds, the possibility of a divalent substructure for $R^4$ means that these cases involve a structure forming cyclic systems in which $R^5$ is in this case a single bond to $R^4$. Examples are morpholinyl and piperidinyl structures.

More preferred embodiments of this first embodiment of the invention and also methods of producing said polysiloxane compounds of the formula (I) and (I') are described below.

$R^4$ is preferably $-CH_3$, $-CH_2CH_3$, $-(CH_2)_2CH_3$, $-(CH_2)_3CH_3$, $-(CH_2)_5CH_3$, $-CH_2CH_2OH$, $-CH_2CH_2NHCO-R^{14}$ or $-CH_2CH_2CH_2NHCO-R^{14}$, in which $R^{14}$ is a straight-chain, cyclic or branched $C_1-C_{18}$-hydrocarbon radical which can be interrupted by —O—, —NH—, —C(O)—, —C(S)— and substituted by —OH.

As mentioned above, $R^4$ and $R^5$ can also together form a cyclic structure of the formulae

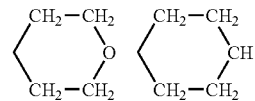

As regards the preferred meanings of $R^1$ in the first embodiment of the polysiloxane compounds, reference may be made to the statements above.

In the first embodiment of the polysiloxane compounds, $R^4$ is preferably a monovalent or divalent straight-chain, cyclic or branched $C_1-C_{16}$, more preferably $C_3-C_{16}$, hydrocarbon radical which can be interrupted by —O—, —NH—, —C(O)—, —C(S)— and substituted by —OH, more preferably a $C_3-C_{16}$ hydrocarbon radical which can be interrupted by —O—, —NH—, $-NR^1-$, —C(O)—, —C(S)— and substituted by —OH in which $R^1$ has the meaning given above.

In the first embodiment of the polysiloxane compounds, F is preferably a divalent or tetravalent straight-chain, cyclic or branched $C_2-C_{20}$-hydrocarbon radical which can be interrupted by —O—, —NH—, —N—, —C(O)—, —C(S), a siloxane chain S, where the preferences given above apply for S, and substituted by —OH.

In a first embodiment of the polysiloxane compounds, K is preferably $-CH_2CH_2CH_2-$, $-(CH_2)_4-$, $-(CH_2)_6-$, $-CH_2CH_2CH_2OCH_2CH(OH)CH_2-$, and $-CH=CHCH_2-$.

In the first embodiment of the polysiloxane compounds, $R^{14}$ is preferably unsubstituted $C_5-C_{17}$-hydrocarbon radicals derived from the corresponding fatty acids or else hydroxylated $C_3-C_{17}$ radicals which can be traced back to hydroxylated carboxylic acids, preferably saccharide carboxylic acids.

In the first embodiment of the polyammonium-polysiloxane compounds which are used in the present invention as active ingredients a) of the active ingredient complex according to the invention, $R^{14}$ is furthermore preferably hydroxylated radicals from the group consisting of

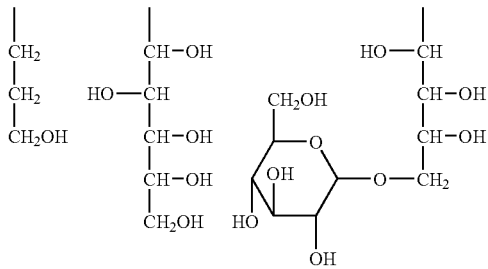

In the first embodiment of the polysiloxane compounds, m is 2 to 100, preferably 2 to 50.

In the first embodiment of the polysiloxane compounds, n is 0 to 1,000, preferably 0 to 100, more preferably 0 to 80 and particularly preferably 10 to 80.

In the first embodiment of the invention, q is 1 to 200, preferably 1 to 50, more preferably 2 to 20 and particularly preferably 2 to 10.

In the first embodiment of the invention, r is 0 to 200, preferably 0 to 100, more preferably 0 to 50 and even more preferably 0 to 20.

As regards the preparation of the polysiloxane-polyammonium compounds according to the invention both of this first embodiment and also all further preferred embodiments of the polysiloxane-polyammonium compounds a) according to the invention of the active ingredient complex according to the invention, reference may be made explicitly to the laid-open specification WO 02/10257.

A particular embodiment of the invention (which is referred to below as a second embodiment of the polysiloxane compounds) is represented by the polysiloxane compounds of the general formula (II),

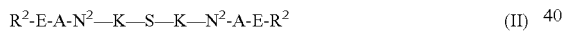

in which
S, K, -A-E-, -E-A- and $R^2$ have the meanings given above, and $N^2$ is an organic radical which contains at least one quaternary ammonium group, of the general formula —$(R^8)N^+(R^9)$—, in which
$R^3$ is a monovalent or divalent straight-chain, cyclic or branched $C_1$-$C_{20}$-hydrocarbon radical which can be interrupted by —O—, —NH—, —C(O)—, —C(S)— and substituted by —OH,
$R^9$ is a monovalent straight-chain, cyclic or branched $C_1$-$C_{20}$-hydrocarbon radical which can be interrupted by —O—, —NH—, —C(O)—, —C(S)— and substituted by —OH, or represents a single bond to a divalent radical $R^3$ or to a trivalent radical K, and the radicals $R^3$ and $R^9$ within the polysiloxane compound of the general formula (II) may be identical to or different from one another.

The polysiloxane compounds of the second embodiment are preferably (a)co-alkylene oxide- and polyquaternary-modified polysiloxanes of the general formula (II'),

in which the designations have the following meanings:
S is —$Si(R^1)_2$—O[—$Si(R^1)_2$—O]$_n$—$Si(R^1)$—
where $R^1$ is $C_1$-$C_{22}$-alkyl, $C_1$-$C_{22}$-fluoroalkyl or aryl,
n is 0 to 1,000, K is a divalent or trivalent straight-chain, cyclic or branched $C_2$-$C_{20}$-hydrocarbon radical which can be interrupted by —O—, —N—, —NH—, —$NR^1$—, —C(O)—, —C(S)— and substituted by —OH,
$N^2$ is a quaternary ammonium structure —$(R^8)N^+(R^9)$—
$R^8$ is a monovalent or divalent straight-chain, cyclic or branched $C_1$-$C_{20}$-hydrocarbon radical which can be interrupted by —O—, —NH—, C(O)—, —C(S)— and substituted by —OH,
$R^9$ is $R^8$ or a single bond to K or $R^8$,
A is —$CH_2C(O)O$—, —$CH_2CH_2C(O)O$— or —$CH_2CH_2CH_2C(O)O$-E is a polyalkylene oxide unit of the structure —$[CH_2CH_2O]_q$—$[CH_2CH(CH_3)O]_r$—
q is 1 to 200
r is 0 to 200 and
$R^{16}$ is H, straight-chain, cyclic or branched $C_1$-$C_{20}$-hydrocarbon radical which can be interrupted by —O— or —C(O)— and substituted by —OH and be acetylenic, olefinic or aromatic.

The possibility of a trivalent substructure for K means here that K can be branched and is then involved with two bonds in the quaternization of $N^2$. The possibility of a divalent substructure for $R^3$ means that these cases involve a structure forming cyclic systems, where $R^9$ is then a single bond to $R^2$.

$R^8$ is preferably —$CH_3$, —$CH_2CH_3$, —$(CH_2)_2CH_3$, —$(CH_2)_3CH_3$, —$(CH_2)_5CH_3$, —$CH_2CH_2OH$— $CH_2CH_2NHCO$—$R^{17}$ or —$CH_2CH_2CH_2NHCO$—$R^{17}$, in which $R^{17}$ is a straight-chain, cyclic or branched $C_1$-$C_{18}$-hydrocarbon radical which can be interrupted by —O—, —NH—, —C(O)—, —C(S)— and substituted by —OH.

As mentioned above, $R^3$ and $R^9$ can also together form a cyclic structure of the formulae:

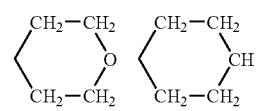

As regards the preferred meanings of $R^1$ in the second embodiment of the polysiloxane compounds, reference may be made to the above statements.

In the second embodiment of the polysiloxane compounds, K is preferably a divalent or trivalent straight-chain, cyclic or branched $C_3$-$C_{16}$-hydrocarbon radical which can be interrupted by —O—, —NH—, —$NR_1$—, —N—, —C(O)—, —C(S)— and substituted by —OH, in which $R^1$ is as defined above.

Radicals of the following structures, for example, are preferred for K:

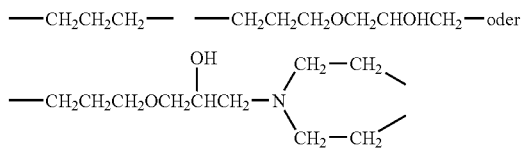

$R^8$ is preferably a monovalent or divalent straight-chain, cyclic or branched $C_1$-$C_{16}$-hydrocarbon radical which can be interrupted by —O—, —NH—, —C(O), —C(S)— and substituted by —OH.

$R^{16}$ is preferably a straight-chain, cyclic or branched $C_1$-$C_{18}$-hydrocarbon radical which can be interrupted by —O— or —C(O)— and substituted by —OH and be acetylenic or olefinic. Furthermore, $R^{16}$ is preferably $C_5$-$C_{17}$-alkyl, —$CH_2CH$=$CH_2$, —$CH_2CH(OH)CH_2OCH_2CH$=$CH_2$, —$CH_2CHH$, —$C(O)CH_3$, —$C(O)CH_2CH_3$.

$R^{17}$ is preferably unsubstituted $C_5$-$C_{17}$-hydrocarbon radicals derived from the corresponding fatty acids or else hydroxylated $C_3$-$C_{17}$ radicals which can be traced back to hydroxylated carboxylic acids, preferably to saccharide carboxylic acids.

$R^{17}$ is particularly preferably selected from the group of

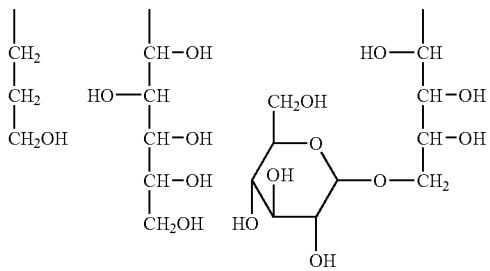

In the second embodiment of the polysiloxane compounds, n is preferably 0 to 200, more preferably 0 to 80, particularly preferably 10 to 80.

In the second embodiment of the polysiloxane compounds, q is preferably 1 to 50, more preferably 2 to 20 and particularly preferably 2 to 10.

In the second embodiment of the polysiloxane compounds, r is preferably 0 to 100 and more preferably 0 to 50.

In the second embodiment of the invention, r is preferably 0 to 20 and more preferably 0 to 10.

As regards the preparation of the polysiloxane compounds according to the invention of the second embodiment, reference may be made to the statements relating to the first preferred embodiment.

One particular embodiment of the polyammonium-polysiloxane compounds a) as essential constituent of the active ingredient complex according to the invention (which is referred to below as the third embodiment of the polysiloxanes) is represented by the polysiloxane compounds of the general formula (III):

$$-[K-S-K-N^3]_m- \quad (III)$$

in which S, K and m are as defined above,
$N^3$ is an organic radical, which contains at least one quaternary ammonium group, of the general formula $$—(R^{10})—N^+(R^{11})—$$

in which $R^{10}$ is a monovalent straight-chain, cyclic or branched $C_1$-$C_{30}$-hydrocarbon radical which can be interrupted by —O—, —NH—, —C(O)—, —C(S)— and substituted by —OH or is a single bond to K,
$R^{11}$ is -A-E-$R^2$, in which -A-E-$R^2$ has the meaning given above.

The polysiloxane compounds of the third embodiment are preferably alkylene oxide-modified polyquaternary polysiloxanes of the general formula (III'), $$[K-S-K-N^3]_m- \quad (III')$$

in which m is 2 to 500,
S is —$Si(R^1)_2$—O[—$Si(R^1)_2$—O]$_n$—$Si(R^1)_2$—
where $R^1$ is $C_1$-$C_{22}$-alkyl, $C_1$-$C_{22}$-fluoroalkyl or aryl,
n=0 to 1,000, $N^3$ is a quaternary ammonium structure
$$—(R^{10})N^+(R^{11})—$$
in which $R^{10}$ is a monovalent or divalent straight-chain, cyclic or branched $C_1$-$C_{30}$-hydrocarbon radical which can be interrupted by —O—, —NH—, —C(O)—, —C(S)— and substituted by —OH or is a single bond to K,
$R^3$ is -A-E- where
A is —$CH_2C(O)O$—, —$CH_2CH_2C(O)O$— or —$CH_2CH_2CH_2C(O)O$— and
E is a polyalkylene oxide unit of the structure $$—[CH_2CH_2O]_q—[CH_2CH(CH_3)O]_r—R^{11}$$

q is from 1 to 200,
r is from 0 to 200,
$R^{13}$ is H, straight-chain, cyclic or branched $C_1$-$C_{20}$-hydrocarbon radical which can be interrupted by —O—, or —C(O)— and substituted by —OH and be acetylenic, olefinic or aromatic, and
K is a divalent or trivalent straight-chain, cyclic or branched $C_2$-$C_{40}$-hydrocarbon radical which can be interrupted by —O—, —NH—, —$NR^1$—, —N—, —C(O)—, —C(S)— and substituted by —OH and contains a quaternary ammonium structure $N^5$, where
$N^5$ in the meaning of —$(R^{19})N^+(R^{20})$—
$R^{19}$ is a monovalent or divalent straight-chain, cyclic or branched $C_1$-$C_{20}$-hydrocarbon radical which can be interrupted by —O—, —NH—, —C(O)—, —C(S)— and substituted by —OH or is a single bond to $R^{10}$, and $R^{20}$ is -A-E-, which is as defined above.

As regards the preparation of the preferred embodiments of the third embodiment of the polysiloxane compounds, reference may explicitly be made, as previously, to the laid-open specification WO 02/10257.

$R^{10}$ and $R^{19}$, independently of one another, are preferably —$CH_3$, —$CH_2CH_3$, —$(CH_2)_2CH_3$, —$(CH_2)_3CH_3$, —$(CH_2)_5CH_3$, —$CH_2CH_2OH$, —$CH_2CH_2NHCOR^{21}$ or —$CH_2CH_2CH_2NHCOR^{21}$, in which $R^{21}$ is a straight-chain, cyclic or branched $C_1$-$C_{18}$-hydrocarbon radical which can be interrupted by —O—, —NH—, —C(O)—, —C(S)— and substituted by —OH.

In one embodiment of the third embodiment of the polysiloxane compounds, a divalent substructure for $R^{10}$ is a structure forming a cyclic system, where $R^{10}$ then has a single bond to K, preferably to a tertiary amino structure or else to the quaternary structure $N^5$ via $R^{19}$.

As regards preferred meanings of $R^1$ in the third embodiment of the polysiloxanes, reference may be made to the statements above.

Preferably, $R^{10}$ is a monovalent or divalent straight-chain, cyclic or branched $C_1$-$C_{25}$-hydrocarbon radical which can be interrupted by —O—, —NH—, —C(O)—, —C(S)— and substituted by —OH.

Preferably, $R^{19}$ is a monovalent or divalent straight-chain, cyclic or branched $C_1$-$C_{25}$-hydrocarbon radical which can be interrupted by —O—, —NH—, —C(O)—, —C(S)— and substituted by —OH.

In the third embodiment of the polysiloxane compounds, K is furthermore preferably a divalent or trivalent straight-chain, cyclic or branched $C_3$-$C_{30}$-hydrocarbon radical which can be interrupted by —O—, —NH—, —$NR^1$—, —N—, —C(O)—, —C(S)— and substituted by —OH, even more preferably K is

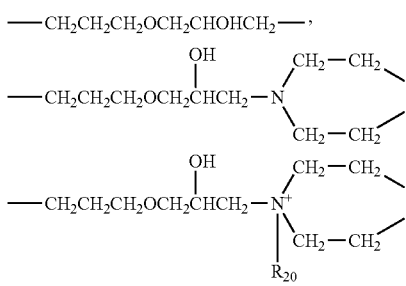

in which $R^{20}$ is as defined above.

In the third embodiment of the polysiloxanes, $R^2$ or $R^{13}$ is preferably a straight-chain, cyclic or branched $C_1$-$C_{18}$-hydrocarbon radical which can be interrupted by —O— or —C(O)— and substituted by —OH and be acetylenic or olefinic. More preferably, $R^2$ or $R^{18}$ is $C_1$-$C_6$-alkyl, —CH$_2$CH=CH$_2$, —CH$_2$CH(OH)CH$_2$OCH$_2$CH=CH$_2$, —CH$_2$CCH, —C(O)CH$_3$ or —C(O)CH$_2$CH$_3$. Preferably, $R^{21}$ is an unsubstituted $C_5$-$C_{17}$-hydrocarbon radical derived from the corresponding fatty acids or else has hydroxylated $C_3$-$C_{17}$ radicals and originates from the group of hydroxylated carboxylic acids, preferably saccharide carboxylic acid. $R^{21}$ is, for example:

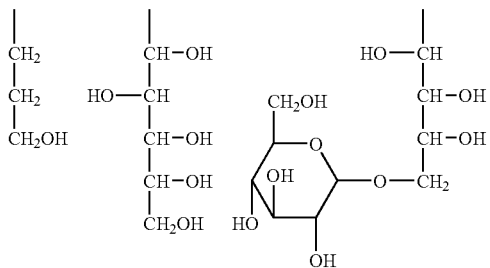

In the third embodiment of the polysiloxanes, m is preferably 2 to 100, and particularly preferably 2 to 50, n is 0 to 100, preferably 0 to 80, and particularly preferably 10 to 80, q is 1 to 50, preferably 2 to 50, particularly preferably 2 to 20, and even more preferably q is 2 to 10, r is 0 to 100, preferably 0 to 50, particularly preferably 0 to 20, and even more preferably r is 0 to 10.

As regards the preparation of the polysiloxane compounds according to the invention of the third embodiment to be used in the active ingredient combination, reference is expediently again made to the laid-open specification WO 02/10257.

One particular embodiment of the polysiloxanes (which is referred to below as fourth embodiment of the polysiloxanes to be used according to the invention) is represented by the polysiloxane compounds of the general formula (IV):

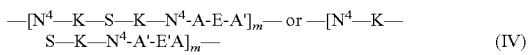

in which m, K, S, -A-E-A' and -A'-E-A- are as defined above, and $N^4$ is an organic radical, which contains at least one quaternary ammonium group, of the general formula —($R^{12}$)$N^+$($R^{13}$)—, in which $R^{12}$ is a monovalent or divalent straight-chain, cyclic or branched $C_1$-$C_{20}$-hydrocarbon radical which can be interrupted by —O—, —NH—, —C(O)—, —C(S)— and substituted by —OH, $R^{13}$ can have the meanings of $R^{12}$, or is a single bond to K or $R^{12}$, and the radicals $R^{12}$ and $R^{13}$ may be identical to or different from one another.

Preferably, the polysiloxane compounds of the fourth embodiment are alkylene oxide-modified polyquaternary polysiloxanes of the general formula (IV'),

in which m=2 to 500,

S is —Si($R^1$)$_2$—O[—Si($R^1$)$_2$—O]—Si($R^1$)$_2$—, in which $R^1$ is $C_1$-$C_{22}$-alkyl, $C_1$-$C_{22}$-fluoroalkyl or aryl, n is 0 to 1,000, K is a divalent or trivalent straight-chain, cyclic or branched $C_2$-$C_{20}$— hydrocarbon radical which may be interrupted by —O—, —NH—, —NR$^1$, —N—, —C(O)—, —C(S)— and substituted by —OH, N is a quaternary ammonium structure —($R^{12}$)$N^+$($R^{13}$)—, in which $R^{12}$ is a monovalent or divalent straight-chain, cyclic or branched $C_1$-$C_{20}$— hydrocarbon radical which may be interrupted by —O—, —NH—, —C(O)—, —C(S)— and substituted by —OH, $R^{13}$ is $R^{12}$ or a single bond to K or $R^{12}$, A is —CH$_2$C(O)O—, —CH$_2$CH$_2$C(O)O— or —CH$_2$CH$_2$CH$_2$C(O)O—

E is a polyalkylene oxide unit of the structure -[CH$_2$CH$_2$O]$_q$—[CH$_2$CH(CH$_3$)O]$_r$— where q=1 to 200 and r=0 to 200.

As regards the production methods, reference may be made to the explanations hitherto.

More preferred embodiments of these fourth embodiment polysiloxanes of the formula (IV) or (IV') are described below.

The possibility of a trivalent substructure for K means that K can be branched and can then be involved with two bonds in the quaternization of $N^4$.

The possibility of a divalent substructure for $R^{12}$ means that in these cases it is a structure forming cyclic systems, where $R^{13}$ is then a single bond to $R^{12}$.

$R^{12}$ is preferably —CH$_3$, —CH$_2$CH$_3$, —(CH$_2$)$_2$CH$_3$, —(CH$_2$)$_3$CH$_3$, —(CH$_2$)$_5$CH$_3$, —CH$_2$CH$_2$OH, —CH$_2$CH$_2$NHCOR$^{22}$ or —CH$_2$CH$_2$CH$_2$NHCOR$^{22}$, in which $R^{22}$ is a straight-chain, cyclic or branched $C_1$-$C_{18}$-hydrocarbon radical which may be interrupted by —O—, —NH—, —C(O)—, —C(S)— and substituted by —OH.

As mentioned above, $R^{12}$ and $R^{13}$ can also together form a cyclic structure of the formulae

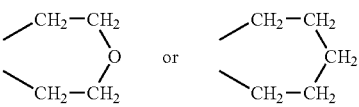

As regards the preferred meanings of $R^1$ in the fourth embodiment of the polysiloxanes, reference may be made to the statements above.

Preferably, $R^{12}$ is a monovalent or divalent straight-chain, cyclic or branched $C_1$-$C_{16}$-hydrocarbon radical which may be interrupted by —O—, —NH—, —C(O)—, —C(S)— and substituted by —OH.

In the fourth embodiment, K is preferably a divalent or trivalent straight-chain, cyclic or branched $C_3$-$C_{16}$-hydrocarbon radical which may be interrupted by —O—, —NH—, —NR$^1$—, —N—, —C(O)—, —C(S)— and substituted by —OH, particularly preferably K is —CH$_2$CH$_2$—, —CH$_2$CH$_2$CH$_2$OCH$_2$CHOHCH$_2$— or

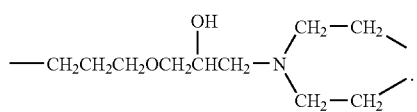

Preferably, $R^{22}$ is an unsubstituted $C_5$-$C_{17}$-hydrocarbon radical which is derived from the corresponding fatty acids or else has hydroxylated $C_3$-$C_{17}$ radicals which can have been traced back to hydroxylated carboxylic acids, preferably saccharide carboxylic acids.

$R^{22}$ is more preferably:

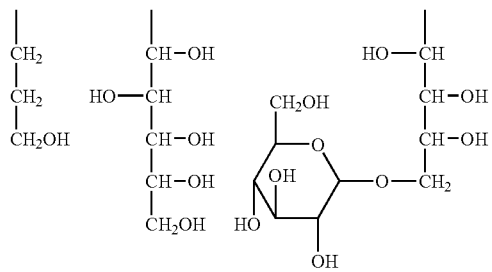

m is preferably 2 to 100, and particularly preferably 2 to 50. n is 0 to 100, preferably 0 to 80, and particularly preferably 10 to 80. q is 1 to 50, preferably 2 to 50, and particularly preferably 2 to 20, even more preferably q is 2 to 10. r is 0 to 100, preferably 0 to 50, and particularly preferably 0 to 20, even more preferably r is 0 to 10.

The term "$C_1$-$C_{22}$-alkyl or $C_1$-$C_{30}$-hydrocarbon radical," as used above, means, for the purposes of the present invention, aliphatic hydrocarbon compounds having 1 to 22 carbon atoms or 1 to 30 carbon atoms which may be straight-chain or branched. By way of example, methyl, ethyl, propyl, n-butyl, pentyl, hexyl, heptyl, nonyl, decyl, undecyl, isopropyl, neopentyl and 1,2,3-trimethylhexyl may be listed.

The term "$C_1$-$C_{22}$-fluoroalkyl" means, as used above, for the purposes of the present invention, aliphatic hydrocarbon compounds having 1 to 22 carbon atoms which may be straight-chain or branched and are substituted by at least one fluorine atom. By way of example, monofluoromethyl, monofluoroethyl, 1,1,1-trifluoroethyl, perfluoroethyl, 1,1,1-trifluoropropyl, 1,2,2-trifluorobutyl may be listed.

For the purposes of the present invention, the term "aryl," as used above, means unsubstituted phenyl or phenyl substituted one or more times by OH, F, Cl, CF3, $C_1$-$C_6$-alkyl, $C_1$-$C_6$-alkoxy, $C_3$-$C_7$-cycloalkyl, $C_2$-$C_6$-alkenyl or phenyl. The expression can optionally also mean naphthyl.

A particular embodiment of the polysiloxanes according to the invention as constituent a) of the active ingredient complex according to the invention (which is referred to below as the fifth embodiment of the polysiloxanes) is represented by the polysiloxanes of the general formula (V):

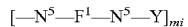

in which
Y is a group of the formula —K—S—K— and -A-E-A'- or -A'-E-A-,
in which m, K, S, -A-E-A'- and -A'-E-A- are as defined above,
the groups K, S, -A-E-A'- and -A'-E-A- within the polysiloxanes of the general formula (V) may be identical to or different from one another, and the molar ratio of the group —K—S—K— and the group -A-E-A'- or -A'-E-A- in the polysiloxane compound of the general formula (V) is from 100:1 to 1:100, $N^5$ is an ammonium group of the general formula —$(R^{23})N^+$($R^{24}$)—, in which
  $R^{23}$ is hydrogen, a monovalent or divalent straight-chain, cyclic or branched $C_1$-$C_{20}$-hydrocarbon radical which may be interrupted by —O—, —NH—, —C(O)—, —C(S)— and substituted by —OH,
  $R^{24}$ is hydrogen, a monovalent straight-chain, cyclic or branched $C_1$-$C_{20}$-hydrocarbon radical which may be interrupted by —O—, —NH—, —C(O)—, C(S)— and substituted by —OH, or is a single bond to a divalent radical $R^{23}$, and the radicals $R^{23}$ and $R^{24}$ within the group —$N^5$—$F^1$—$N^5$- and in the polysiloxane compound may be identical to or different from one another,
$F^1$ is a divalent straight-chain, cyclic or branched hydrocarbon radical which can be interrupted by —O—, —NH—, —N—, —C(O)— or —C(S)— or by a group -E-, in which E is as defined above, and in which a plurality of $N^5$ and $F^1$ may in each case be identical to or different from one another.

The molar ratio of the group —K—S—K— and of the group -A-E-A'- or -A'-E-A- in the polysiloxane compound of the general formula (V) is between 100:1 and 1:100. As indicated in the laid-open specification WO 02/10257, this molar ratio can be controlled through the choice of molar ratio of the starting compounds, in particular the ratio of the α,ω-halocarboxylic acid polyalkylene oxide ester compounds and the polysiloxane bisepoxide compounds used preferably according to the invention. The properties of the product depend essentially on the ratio of the starting materials used, and also the length of the polyalkylene oxide or polysiloxane blocks present therein.

In a preferred embodiment of the fifth embodiment of the polysiloxanes, K is a divalent hydrocarbon radical having at least 4 carbon atoms which has a hydroxyl group and which may be interrupted by an oxygen atom.

In a preferred embodiment of the fifth embodiment of the polysiloxanes, F1 is a divalent straight-chain, cyclic or branched $C_2$-$C_{30}$-hydrocarbon radical which may be interrupted by —O—, —NH—, —N—, —C(O)—, —C(S)— or by a group -E-, in which E is as defined above, and in which the carbon atoms which result from the radical E are not included in the 2 to 30 carbon atoms of the $C_2$-$C_{30}$ hydrocarbon radical.

In a further preferred embodiment of the fifth embodiment of the invention,

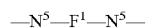

is a group of the formula:

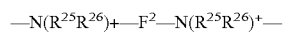

in which
$R^{25}$ is a monovalent or divalent straight-chain, cyclic or branched $C_1$-$C_{20}$-hydrocarbon radical which may be interrupted by —O—, —NH—, —C(O)—, —C(S)— and substituted by —OH, particular preference being given to methyl,
$R^{26}$ is a monovalent straight-chain, cyclic or branched $C_1$-$C_{20}$-hydrocarbon radical which can be interrupted by —O—, —NH—, —C(O)—, —C(S) and substituted by —OH, particular preference being given to methyl, or is a single bond to a divalent radical $R^{25}$, and the radicals $R^{25}$ and $R^{26}$ within the group —$N^5$—$F^2$—$N^5$- and in the polysiloxane compound may be identical to or different from one another, and $F^2$ is a divalent straight-chain, cyclic or branched hydrocarbon radical which may be interrupted by —O—, —NH—, —N—, —C(O)—, —C(S)—.

In an even more preferred embodiment, $F^2$ is a branched, preferably straight-chain $C_1$-$C_6$-alkanediyl group, among which a 1,6-hexanediyl (or hexamethylene) group is preferred.

In a further preferred embodiment of the fifth embodiment of the polysiloxane compounds,

—$N^5$—$F^1$—$N^5$— is a group of the formula:

—$N(R^{27}R^{28})^+$—$F^3$—$N(R^{27}R^{28})^+$— in which
$R^{27}$ and $R^{28}$ are in each case hydrogen, $C_1$-$C_6$-alkyl or hydroxy($C_1$-$C_6$)alkyl, preferably hydrogen, methyl or —$CH_2CH_2OH$, and
$F^3$ is a divalent straight-chain, cyclic or branched hydrocarbon radical which is interrupted by a group -E-, in which E is as defined above.

$F^3$ is particularly preferably a group of the formula

-D-E-D- in which E is as defined above and D is in each case a single bond or a straight-chain or branched $C_1$-$C_6$-alkanediyl group, with the proviso that D is not a single bond when it bonds to a terminal oxygen atom of group E.

Preferably, the group -D-E-D- is represented by a group of the formula

-D-$(OCH_2CH_2)_v$$(OCH_2CH(CH_3))_w$—O-D- in which D is a straight-chain or branched $C_1$-$C_6$-alkanediyl group and r and q are as defined above. In the group -D-$(OCH_2CH_2)_q$$(OCH_2CH(CH_3))_r$—O-D-, the ethylene oxide and propylene oxide units can be arranged arbitrarily, e.g., as random copolymer unit or as block copolymer unit.
v is preferably 1 to 100, more preferably 1 to 70, even more preferably 1 to 40.
w is preferably 0 to 100, more preferably 0 to 70, even more preferably 0 to 40.

In a further preferred embodiment of the fifth embodiment of the invention, the group

—$N^5$—$F^1$—$N^5$ is represented by a group of the formula:

—$N^+R^{25}R^{26}$—$F^2$—$N^{+R25}R^{26}$— and a group of the formula:

—$N^+R^{27}R^{28}$—$F^3$—$N^+R^{27}R^{28}$— in which the substituents in each case have the above meanings.

This means that the polysiloxane compounds of the general formula (V) are composed of two different types of group —$N^5$—$F^1$—$N^5$—.

In this embodiment, the molar ratio of the group

—$N^+R^{25}R^{26}$—$F^2$—$N^+R^{25}R^{26}$— to the group

—$N^+R^{27}R^{28}$—$F^3$—$N^+R^{27}R^{28}$— is expediently 70:30 to 95:5, preferably 80:20 to 90:10.

The polysiloxane compounds of the general formula (V) can be cyclic or linear. In the case of the linear compounds, the terminal groups result either from the bifunctional monomers described below and used for the production, or their functionalized derivatives, or from monoamines which are added during the polymerization as chain terminators. The terminal groups resulting from the use of the monoamine chain terminator are preferably present as ammonium groups, either through quaternization or protonization.

In a further preferred embodiment of the fifth embodiment of the polysiloxanes, K is one of the groups of the formula:

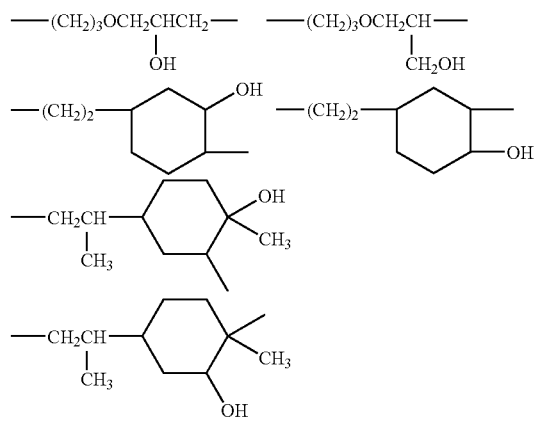

In the fifth embodiment of the polysiloxanes, q is preferably in the range from 1 to 50, in particular 2 to 50, specifically 2 to 20 and very specifically 2 to 10, and r is in the range from 0 to 100, in particular 0 to 50, specifically 0 to 20 and very specifically 0 to 10.

In the fifth embodiment of the invention, the organic or inorganic acid radical for the neutralization of the charges resulting from the ammonium group(s) is expediently selected from inorganic radicals, such as chloride, bromide, hydrogensulfate, sulfate, or organic radicals, such as acetate, propionate, octanoate, decanoate, dodecanoate, tetradecanoate, hexadecanoate, octadecanoate and oleate, where the chloride and bromide mentioned at the beginning preferably result from the reaction of the alkyl halide groups with amine groups. Furthermore, the polysiloxanes of the fifth embodiment are present in protoniated form as amine salts or as amines.

The polysiloxanes of the fifth embodiment of the invention are expediently prepared by one of the methods described in the laid-open specification WO 02/10257.

The polyammonium-polysiloxane compounds described above can be obtained, for example, under the trade name Baysilone® from GE Bayer Silicones. The products with the names Baysilone TP 3911, SME 253 and SFE 839 are preferred here. Very particular preference is given to the use of Baysilone TP 3911 as the active component of the compositions according to the invention.

The polyammonium-polysiloxane compounds described above are used in the active ingredient complex according to the invention in an amount of from 0.01 to 10% by weight, preferably 0.01 to 7.5% by weight, particularly preferably 0.01 to 5.0% by weight, very particularly preferably from 0.05 to 2.5% by weight, in each case based on the total composition.

The ratio of the polyammonium-polysiloxane compounds to the further synergistic active ingredient component is generally according to the invention 1:1000 to 1:2, preferably 1:100 to 1:2, particularly preferably 1:50 to 1:2 and very particularly preferably 1:10 to 1:2.

The invention also encompasses the finding that a mixture of at least two different silicones can be used in the compositions according to the invention. Preferred mixtures of different silicones are, for example, dimethicones and dimethiconols, linear dimethicones and cyclic dimethiconols. A very particularly preferred mixture of silicones consists of at least one cyclic dimethiconol and/or dimethicone, at least one further noncyclic dimethicone and/or dimethiconol, and at least one aminofunctional silicone. If different silicones are used as a mixture, then the mixing ratio is largely variable. However, preference is given to using all silicones used for the mixture in a ratio of 5:1 to 1:5 in the case of a binary mixture. A ratio of 3:1 to 1:3 is particularly preferred. Very particularly preferred mixtures comprise all silicones present in the mixture as largely as possible in a ratio of about 1:1, in each case based on the amounts used in % by weight.

If a mixture of at least two silicones is used, then this mixture is present in the compositions according to the invention in amounts of from 0.01 to 10% by weight, preferably 0.01 to 8% by weight, particularly preferably 0.1 to 7.5% by weight and in particular 0.1 to 5% by weight, of silicone mixture, based on the composition.

The teaching according to the invention also encompasses the fact that a mixture of two or more fatty substances (D) from different classes of fatty substances, at least two different fatty substance classes, can be used in the compositions according to the invention. The preferred mixtures of at least two oil and fat components in this case obligatorily comprise at least one further silicone component. Preferably, the silicone component is in this case selected from the dimethiconols and the amodimethicones.

The total amount of oil and fat components in the compositions according to the invention is usually 0.5-75% by weight, based on the total composition. Amounts of 0.5-35% by weight are preferred according to the invention.

A further group of ingredients that can be used advantageously in the compositions according to the invention is the group of surface-active substances. Surface-active substances are understood as meaning in particular surfactants and emulsifiers and also solubility promoters.

The term surfactants (E) is understood as meaning interface-active substances which can form adsorption layers at surfaces and interfaces or can aggregate in volume phases to give micelle colloids or lyotropic mesophases. A distinction is made between anionic surfactants consisting of a hydrophobic radical and a negatively charged hydrophilic head group, amphoteric surfactants which carry both a negative and also a compensating positive charge, cationic surfactants which, besides a hydrophobic radical, have a positively charged hydrophilic group, and nonionic surfactants which have no charges but strong dipole moments and are highly hydrated in aqueous solution. More detailed definitions and properties of surfactants can be found in "H.-D. Dörfler, Grenzflächen-und Kolloidchemie [Interface and colloid chemistry], VCH Verlagsgesellschaft mbH. Weinheim, 1994." The definition given above can be found on pp. 190 et seq. in this publication. The surfactants specified below are exclusively known compounds. With regard to structure and preparation of these substances, reference may be made to relevant overview works, for example J. Falbe (ed.), "Surfactants in Consumer Products," Springer Verlag, Berlin, 1987, pp. 54-124 or J. Falbe (ed.), "Katalysatoren, Tenside und Mineralöladditive" [Catalysts, surfactants and mineral oil additives]," Thieme Verlag, Stuttgart, 1978, pp. 123-217.

Suitable anionic surfactants (E1) in preparations according to the invention are all anionic surface-active substances suitable for use on the human body. These are characterized by a solubilizing, anionic group, such as, for example, a carboxylate, sulfate, sulfonate or phosphate group, and a lipophilic alkyl group having about 8 to 30 carbon atoms. Additionally, glycol or polyglycol ether groups, ester, ether and amide groups and also hydroxyl groups may be present in the molecule. Typical examples of anionic surfactants are alkylbenzenesulfonates, alkanesulfonates, olefinsulfonates, alkyl ether sulfonates, glycerol ether sulfonates, α-methyl ester sulfonates, sulfo-fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (in particular vegetable products based on wheat) and alkyl (ether) phosphates. If the anionic surfactants comprise polyglycol ether chains, these can have a conventional homolog distribution, but preferably have a narrowed homolog distribution. Examples of particularly suitable anionic surfactants are, in each case in the form of the sodium, potassium and ammonium salts and also the mono-, di- and trialkanolammonium salts having 2 to 4 carbon atoms in the alkanol group, linear and branched fatty acids having 8 to 30 carbon atoms (soaps), ether carboxylic acids of the formula R—O—($CH_2$—$CH_2O$)x—$CH_2$—COOH, in which R is a linear alkyl group having 8 to 30 carbon atoms and x=0 or 1 to 16, acyl sarcosides having 8 to 24 carbon atoms in the acyl group, acyl taurides having 8 to 24 carbon atoms in the acyl group, acyl isethionates having 8 to 24 carbon atoms in the acyl group are skin-friendly surface-active substances that have been known for a long time and which are accessible by esterification of fatty acids with the sodium salt of 2-hydroxyethanesulfonic acid (isethionic acid), e.g., according to the method described in U.S. Pat. No. 3,320,292. Using fatty acids having 8 to 24 carbon atoms, thus, for example, lauric acid, myristic acid, palmitic acid or stearic acid or else technical-grade fatty acid fractions, e.g., the $C_{12}$-$C_{18}$-fatty acid fraction obtainable from coconut fatty acid for this esterification gives the suitable $C_{12}$-$C_{18}$-acyl isethionates preferred according to the invention. It is known to convert the sodium salts of $C_{12}$-$C_{18}$-acyl isethionates to a suitable form for transportation and for use similarly to soaps based on fatty acid by kneading, pelleting, extrusion, cutting and unit compression. In this way, it is possible to produce needles, granules, noodles, bars and manageable toilet soap bars.

sulfosuccinic acid mono- and dialkyl esters having 8 to 24 carbon atoms in the alkyl group and sulfosuccinic acid monoalkyl polyoxyethyl esters having 8 to 24 carbon atoms in the alkyl group and 1 to 6 oxyethyl groups. The sulfosuccinic acid monoalkyl($C_8$-$C_{24}$) ester disodium salts are prepared by a known method, for example, by reacting maleic anhydride with a fatty alcohol having 8-24 carbon atoms to give the maleic acid monoester of the fatty alcohol, and sulfating this with sodium sulfite to give the sulfosuccinic acid ester. Particularly suitable sulfosuccinic acid esters are derived from fatty alcohol fractions having 12-18 carbon atoms as are accessible, for example, from coconut fatty acid or coconut fatty acid methyl ester by hydration.

linear alkanesulfonates having 8 to 24 carbon atoms, linear alpha-olefin sulfonates having 8 to 24 carbon atoms, alpha-sulfo fatty acid methyl esters of fatty acids having 8 to 30 carbon atoms, alkyl sulfates and alkyl polyglycol ether sulfates of the formula R—O(CH$_2$—CH$_2$O)$_x$—OSO$_3$H, in which R is a preferably linear alkyl group having 8 to 30 carbon atoms and x=0 or 1 to 12, mixtures of surface-active hydroxysulfonates as in DE-A-37 25 030, sulfated hydroxyalkyl polyethylene and/or hydroxyalkylene propylene glycol ethers as in DE-A-37 23 354, sulfonates of unsaturated fatty acids having 8 to 24 carbon atoms and 1 to 6 double bonds as in DE-A-39 26 344, esters of tartaric acid and citric acid with alcohols which constitute addition products of about 2-15 molecules of ethylene oxide and/or propylene oxide onto fatty alcohols having 8 to 22 carbon atoms, alkyl and/or alkenyl ether phosphates of the formula (E1-I),

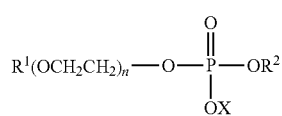

(E1-I)

in which R$^1$ is preferably an aliphatic hydrocarbon radical having 8 to 30 carbon atoms, R$^2$ is hydrogen, a radical (CH$_2$CH$_2$O)$_n$R$^2$ or X, n is numbers from 1 to 10 and X is hydrogen, an alkali metal or alkaline earth metal or NR$^3$R$^4$R$^5$R$^6$, where R$^3$ to R$^6$, independently of one another, are hydrogen or a C$_1$ to C$_4$-hydrocarbon radical, sulfated fatty acid alkylene glycol esters of the formula (E1-II)

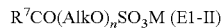

in which R$^7$CO is a linear or branched, aliphatic, saturated and/or unsaturated acyl radical having 6 to 22 carbon atoms, Alk is CH$_2$CH$_2$, CHCH$_3$CH$_2$ and/or CH$_2$CHCH$_3$, n is numbers from 0.5 to 5 and M is a cation, as described in DE-A 197 36 906.5, monoglyceride sulfates and monoglyceride ether sulfates of the formula (E1-III)

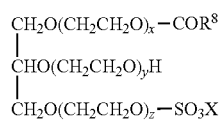

(E1-III)

in which R$^8$CO is a linear or branched acyl radical having 6 to 22 carbon atoms, x, y and z are in total 0 or numbers from 1 to 30, preferably 2 to 10, and X is an alkali metal or alkaline earth metal. Typical examples of monoglyceride (ether) sulfates suitable for the purposes of the invention are the reaction products of lauric acid monoglyceride, coconut fatty acid monoglyceride, palmitic acid monoglyceride, stearic acid monoglyceride, oleic acid monoglyceride and tallow fatty acid monoglyceride, and also their ethylene oxide adducts with sulfur trioxide or chlorosulfonic acid in the form of their sodium salts. Preference is given to using monoglyceride sulfates of the formula (E1-III) in which R$^3$CO is a linear acyl radical having 8 to 18 carbon atoms, as have been described, for example, in EP-B1 0 561 825, EP-B1 0 561 999, DE-A1 42 04 700 or by A. K.

Biswas et al., in J. Am. Oil. Chem. Soc. 37, 171 (1960) and F. U. Ahmed in J. Am. Oil. Chem. Soc. 67, 8 (1990), amide ether carboxylic acids as described in EP 0 690 044, condensation products of a water-soluble salt of a water-soluble protein hydrolysate-fatty acid condensation product. These are produced by condensation of C$_8$-C$_{30}$ fatty acids, preferably of fatty acids having 12-18 carbon atoms with amino acids, mono-, di- and water-soluble oligopeptides and mixtures of such products, as are produced in the hydrolysis of proteins. These protein hydrolysate-fatty acid condensation products are neutralized with a base and are then present preferably as alkali metal, ammonium, mono-, di- or trialkanolammonium salt. Such products have been commercially available for a long time under the trade name Lamepon®, Maypon®, Gluadin®, Hostapon® KCG or Amisoft®.

Preferred anionic surfactants are alkyl sulfates, alkyl polyglycol ether sulfates and ether carboxylic acids having 10 to 18 carbon atoms in the alkyl group and up to 12 glycol ether groups in the molecule, sulfosuccinic acid mono- and dialkyl esters having 8 to 18 carbon atoms in the alkyl group and sulfosuccinic acid monoalkyl polyoxyethyl esters having 8 to 18 carbon atoms in the alkyl group and 1 to 6 oxyethyl groups, monoglyceride sulfates, alkyl and alkylene ether phosphates, and protein fatty acid condensates.

"Zwitterionic surfactants" (E2) is the term used to refer to those surface-active compounds which carry at least one quaternary ammonium group and at least one —COO$^{(-)-}$ or —SO$_3^{(-)}$ group in the molecule. Particularly suitable zwitterionic surfactants are the betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and also cocoacylaminoethyl hydroxyethylcarboxymethyl glycinate. A preferred zwitterionic surfactant is the fatty acid amide derivative known under the INCI name Cocamidopropyl Betaine.

Ampholytic surfactants (E3) are understood as meaning those surface-active compounds which, apart from a C$_8$-C$_{24}$-alkyl or -acyl group in the molecule, comprise at least one free amino group and at least one —COOH— or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxy-ethyl-N-alkylamidopropylglycines, N-alkyltaurines, N-alkylsarcosines, 2-alkylaminopropionic acids and alkylamino acetic acids having in each case about 8 to 24 carbon atoms in the alkyl group. Typical examples of amphoteric and zwitterionic surfactants are alkylbetaines, alkylamidobetaines, aminopropionates, aminoglycinates, imidazoliniumbetaines and sulfobetaines.

Particularly preferred ampholytic surfactants are the N-cocoalkylaminopropionate, the cocoacylaminoethylaminopropionate and the C$_{12}$-C$_{18}$-acylsarcosine.

Nonionic surfactants (E4) contain, as hydrophilic group, e.g., a polyol group, a polyalkylene glycol ether group or a combination of polyol and polyglycol ether group. Such compounds are, for example, addition products of from 2 to 50 mol of ethylene oxide and/or 0 to 5 mol of propylene oxide onto linear and branched fatty alcohols having 6 to 30 carbon atoms, the fatty alcohol polyglycol ethers and the fatty alcohol polypropylene glycol ethers or mixed fatty alcohol polyethers, addition products of from 2 to 50 mol of ethylene oxide and/or 0 to 5 mol of propylene oxide onto linear and branched fatty acids having 6 to 30 carbon atoms, the fatty acid polyglycol ethers and the fatty acid polypropylene glycol ethers and mixed fatty acid polyethers, addition products of from 2 to 50 mol of ethylene oxide and/or 0 to 5 mol of propylene oxide onto linear and branched alkylphenols having 8 to 15 carbon atoms in the alkyl group, the alkylphenol polyglycol ethers and the alkylpolypropylene glycol ethers, and mixed alkylphenol polyethers, addition products of from 2 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group, all terminally capped with a methyl or $C_2$-$C_6$— alkyl radical, such as, for example, the grades available under the trade names Dehydrol® LS, Dehydrol® LT (Cognis), $C_{12}$-$C_{30}$-fatty acid mono- and diesters of addition products of from 1 to 30 mol of ethylene oxide onto glycerol, addition products of from 5 to 60 mol of ethylene oxide onto castor oil and hydrogenated castor oil, polyol fatty acid esters, such as, for example, the commercial product Hydagen® HSP (Cognis) or Sovermol grades (Cognis), alkoxylated triglycerides, alkoxylated fatty acid alkyl esters of the formula (E4-I)

$$R^1CO—(OCH_2CHR^2)_w OR^3 \qquad (E4\text{-}I)$$

in which $R^1CO$ is a linear or branched, saturated and/or unsaturated acyl radical having 6 to 22 carbon atoms, $R^2$ is hydrogen or methyl, $R^3$ is linear or branched alkyl radicals having 1 to 4 carbon atoms and w is numbers from 1 to 20, amine oxides, hydroxy mixed ethers, as are described, for example, in DE-A 19738866, sorbitan fatty acid esters and addition products of ethylene oxide onto sorbitan fatty acid esters, such as, for example, the polysorbates, sugar fatty acid esters and addition products of ethylene oxide onto sugar fatty acid esters, addition products of ethylene oxide onto fatty acid alkanolamides and fatty amines, sugar surfactants of the type of the alkyl and alkenyl oligoglycosides according to formula (E4-II), $$R^4O—[G]_p \qquad (E4\text{-}II)$$

in which $R^4$ is an alkyl or alkenyl radical having 4 to 22 carbon atoms, G is a sugar radical having 5 or 6 carbon atoms and p is numbers from 1 to 10. They can be obtained by the relevant methods of preparative organic chemistry. By way of representation of the extensive literature, reference may be made here to the overview paper by Biermann et al. in Starch 45, 281 (1993), B. Salka in Cosm. Toil. 108, 89 (1993), and J. Kahre et al., in SÖFW-Journal Issue 8, 598 (1995).

The alkyl and alkenyl oligoglycosides can be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula (E4-II) gives the degree of oligomerization (DP), i.e. the distribution of mono- and oligoglycosides and is a number between 1 and 10. Whereas p in the individual molecule must always be an integer and here can in particular assume values p=1 to 6, the value p for a specific alkyl oligoglycoside is an analytically determined calculated parameter which in most cases is a fraction. Preference is given to using alkyl and/or alkenyl oligoglycosides with an average degree of oligomerization p of from 1.1 to 3.0. From an applications point of view, preference is given to those alkyl and/or alkenyl oligoglycosides whose degree of oligomerization is less than 1.7 and in particular is between 1.2 and 1.4. The alkyl or alkenyl radical $R^4$ can be derived from primary alcohols having 4 to 11, preferably 8 to 10, carbon atoms. Typical examples are butanol, caproic alcohol, caprylic alcohol, capric alcohol and undecyl alcohol, and technical-grade mixtures thereof, as are obtained, for example, during the hydration of technical-grade fatty acid methyl esters or in the course of the hydration of aldehydes from the Roelen oxo synthesis. Preference is given to alkyl oligoglucosides of chain length $C_8$-$C_{10}$ (DP=1 to 3), which are produced as forerunning in the distillative separation of technical-grade $C_8$-$C_{18}$ coconut fatty alcohol and may be contaminated with a fraction of less than 6% by weight of $C_{1-2}$-alcohol, and also alkyl oligoglucosides based on technical-grade $C_{9/11}$-oxo alcohols (DP=1 to 3). The alkyl or alkenyl radical $R^{15}$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and technical-grade mixtures thereof, which can be obtained as described above. Preference is given to alkyl oligoglucosides based on hydrogenated $C_{12/14}$ coconut alcohol with a DP of from 1 to 3.

sugar surfactants of the type of fatty acid N-alkylpolyhydroxyalkylamides, a nonionic surfactant of the formula (E4-III),

(E4-III)

in which $R^5CO$ is an aliphatic acyl radical having 6 to 22 carbon atoms, $R^6$ is hydrogen, an alkyl or hydroxyalkyl radical having 1 to 4 carbon atoms and [Z] is a linear or branched polyhydroxyalkyl radical having 3 to 12 carbon atoms and 3 to 10 hydroxyl groups. The fatty acid N-alkylpolyhydroxyalkylamides are known substances which can usually be obtained by reductive amination of a reducing sugar with ammonia, an alkylamine or an alkanolamine and subsequent acylation with a fatty acid, a fatty acid alkyl ester or a fatty acid chloride. With regard to the methods for their preparation, reference may be made to the US patent specifications U.S. Pat. No. 1,985,424, U.S. Pat. No. 2,016,962 and U.S. Pat. No. 2,703,798, and also the International patent application WO 92/06984. An overview of this theme by H. Kelkenberg can be found in Tens. Surf. Det. 25, 8 (1988). Preferably, the fatty acid N-alkylpolyhydroxyalkylamides are derived from reducing sugars having 5 or 6 carbon atoms, in particular from glucose. The preferred fatty acid N-alkylpolyhydroxyalkylamides are therefore fatty acid N-alkylglucamides, as given by the formula (E4-IV):

$$R^7CO—(NR^8)—CH_2—[CH(OH)]_4—CH_2OH \qquad (E4\text{-}IV)$$

As fatty acid N-alkylpolyhydroxyalkylamides, preference is given to using glucamides of the formula (E4-IV) in which $R^8$ is hydrogen or an alkyl group and $R^7CO$ is the acyl radical of caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, arachic acid, gadoleic acid, behenic acid or erucic acid or technical-grade mixtures thereof. Particular preference is given to fatty acid N-alkylglucamides of the formula (E4-IV) which are obtained by reductive amination of glucose with methylamine and subsequent acylation with lauric acid or C12/14 coconut fatty acid or a corresponding derivative. Furthermore, the polyhydroxyalkylamides can also be derived from maltose and palatinose.

The sugar surfactants can be present in the agents used according to the invention preferably in amounts of 0.1-20% by weight, based on the total agent. Amounts of 0.5-15% by weight are preferred, and very particular preference is given to amounts of 0.5-7.5% by weight.

Further typical examples of nonionic surfactants are fatty acid amide polyglycol ethers, fatty amine polyglycol ethers, mixed ethers and mixed formals, protein hydrolysates (in particular vegetable products based on wheat) and polysorbates.

Preferred nonionic surfactants have proven to be the alkylene oxide addition products onto saturated linear fatty alcohols and fatty acids having in each case 2 to 30 mol of ethylene oxide per mole of fatty alcohol or fatty acid as well as the sugar surfactants. Preparations with excellent properties are likewise obtained if they comprise fatty acid esters of ethoxylated glycerol as nonionic surfactants.

These compounds are characterized by the following parameters. The alkyl radical R contains 6 to 22 carbon atoms and may either be linear or branched. Preference is given to primary linear and 2-methyl-branched aliphatic radicals. Such alkyl radicals are, for example, 1-octyl, 1-decyl, 1-lauryl, 1-myristyl, 1-cetyl and 1-stearyl. Particular preference is also given to 1-octyl, 1-decyl, 1-lauryl, 1-myristyl. When using "oxo alcohols" as starting materials, compounds with an uneven number of carbon atoms in the alkyl chain predominate.

The compounds with alkyl groups used as surfactant may in each case be single substances. However, it is generally preferred, when producing these substances, to start from native vegetable or animal raw materials, thus giving mixtures of substances with different alkyl chain lengths that are dependent on the particular raw material.

In the case of the surfactants which constitute addition products of ethylene oxide and/or propylene oxide onto fatty alcohols or derivatives of these addition products, it is possible to use either products with a "normal" homolog distribution or those with a narrowed homolog distribution. "Normal" homolog distribution is understood here as meaning mixtures of homologs which are obtained in the reaction of fatty alcohol and alkylene oxide using alkali metals, alkali metal hydroxides or alkali metal alkoxides as catalysts. Narrowed homolog distributions, on the other hand, are obtained if, for example, hydrotalcites, alkaline earth metal salts of ether carboxylic acids, alkaline earth metal oxides, hydroxides or alkoxides are used as catalysts. The use of products with a narrowed homolog distribution may be preferred.

Additives for further improving the creaminess of the foam and the skin feel during and after application have also proven to be nonionic surfactants, the additional use of which for producing the compositions according to the invention can be recommended: particular preference is therefore given to compositions according to the invention with an additional content of 0.1-20% by weight of nonionic surfactants with an HLB value of 2-18. Such products can be prepared through the addition reaction of ethylene oxide onto e.g., fatty alcohols having 6-30 carbon atoms, onto fatty acids having 6-30 carbon atoms or onto glycerol or sorbitan fatty acid partial esters based on $C_{12}$-$C_{18}$-fatty acids or onto fatty acid alkanolamides. The HLB value means the proportion of hydrophilic groups, e.g., of glycol ether or polyol groups, based on the total molecule and is calculated according to the equation $$HLB = \tfrac{1}{5} \times (100\% \text{ by weight L}),$$

where % by weight L is the weight fraction of lipophilic groups, thus, e.g., of alkyl or acyl groups having 6-30 carbon atoms in the surfactant molecule.

Cationic surfactants (E5) of the quaternary ammonium compound type, the ester quat type, the imidazoline type and the amidoamine type can likewise be used according to the invention. Preferred quaternary ammonium compounds are ammonium halides, in particular chlorides and bromides, such as alkyltrimethylammonium chlorides, dialkyldimethylammonium chlorides and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and also the imidazolium compounds known under the INCI names Quaternium-27 and Quaternium-83. The long alkyl chains of the above-mentioned surfactants preferably have 8 to 30 carbon atoms. Typical examples of cationic surfactants are quaternary ammonium compounds and ester quats, in particular quaternized fatty acid trialkanolamine ester salts.

According to the invention, cationic compounds with behenyl radicals, in particular the substances known under the name benhentrimonium chloride or bromide (docosanyltrimethylammonium chloride or bromide) can be used particularly preferably. Other preferred QAVs have at least two behenyl radicals. These substances are commercially available, for example, under the names Genamin® KDMP (Clariant).

Ester quats are known substances which contain both at least one ester function and also at least one quaternary ammonium group as structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, an N,N-bis(2-palmitoyloxyethyl)dimethylammonium chloride, and Dehyquart® F-75, Dehyquart® C-4046, Dehyquart® L80 and Dehyquart® AU-35 are examples of such ester quats.

As further cationic surfactants, the agents according to the invention can comprise at least one quaternary imidazoline compound, i.e. a compound which has a positively charged imidazoline ring. The formula (E5-V) depicted below shows the structure of these compounds.

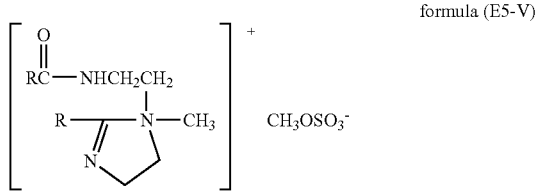

formula (E5-V)

The radicals R, independently of one another, are in each case a saturated or unsaturated, linear or branched hydrocarbon radical with a chain length of 8 to 30 carbon atoms. The preferred compounds of the formula I contain for R in each case the same hydrocarbon radical. The chain length of the radicals R is preferably 12 carbon atoms. Particular preference is given to compounds with a chain length of at least 16 carbon atoms and very particular preference to those with at least 20 carbon atoms. A very particularly preferred compound of formula I has a chain length of 21 carbon atoms. A commercial product of this chain length is known, for example, under the name Quaternium-91. In the formula (E5-V), methosulfate is depicted as counterion. However, according to the invention, the halides, such as chloride, fluoride, bromide, and also phosphates are also encompassed as counterions.

The imidazolines of the formula (E5-V) are present in the compositions according to the invention in amounts of 0.01 to 20% by weight, preferably in amounts of 0.05 to 10% by weight and very particularly preferably in amounts of 0.1 to 7.5% by weight. The very best results are obtained here with amounts of from 0.1 to 5% by weight, in each case based on the total composition of the respective agent.

The alkylamidoamines are usually prepared by amidation of natural or synthetic fatty acids and fatty acid cuts with dialkylaminoamines. One compound from this group of substances that is particularly suitable according to the invention is the stearamidopropyldimethylamine commercially available under the name Tegoamid® S18. The alkylamidoamines can either be present as they are or be converted into a quaternary compound in the composition by protonation in correspondingly acidic solution, although they can also be used as permanently quaternary compound in the compositions according to the invention. Examples of permanently quaternized amidoamines are, for example, the raw materials with the trade name Rewoquat® UTM 50, Lanoquat® DES-50 or Empigen CSC.

The cationic surfactants (E5) are present in the agents used according to the invention preferably in amounts of from 0.05 to 10% by weight, based on the total agent. Amounts of from 0.1 to 5% by weight are particularly preferred.

Anionic, nonionic, zwitterionic and/or amphoteric surfactants, and mixtures thereof, may be preferred according to the invention.

The surfactants (E) are used in amounts of 0.1-45% by weight, preferably 0.5-30% by weight and very particularly preferably from 0.5-25% by weight, based on the total agent used according to the invention.

Furthermore, the surface-active substances include emulsifiers (F). At the phase interface, emulsifiers bring about the formation of water- or oil-stable adsorption layers which protect the dispersed droplets against coalescence and thus stabilize the emulsion. Emulsifiers, like surfactants, are therefore composed of a hydrophobic molecular moiety and a hydrophilic molecular moiety. Hydrophilic emulsifiers form preferably O/W emulsions, and hydrophobic emulsifiers form preferably W/O emulsions. An emulsion is understood as meaning a droplet-like distribution (dispersion) of one liquid in another liquid with the expenditure of energy to produce stabilizing phase interfaces by means of surfactants. The choice of these emulsifying surfactants or emulsifiers is governed here by the substances to be dispersed and the particular outer phase, and also the finely divided nature of the emulsion. More detailed definitions and properties of emulsifiers can be found in H.-D. Dorfler, "Grenzflächen-und Kolloidchemie" [Interface and colloid chemistry], VCH Verlagsgesellschaft mbH. Weinheim, 1994. Emulsifiers that can be used according to the invention are, for example,

- addition products of from 4 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
- $C_{12}$-$C_{22}$-fatty acid mono- and diesters of addition products of from 1 to 30 mol of ethylene oxide onto polyols having 3 to 6 carbon atoms, in particular onto glycerol,
- ethylene oxide and polyglycerol addition products onto methyl glucoside fatty acid esters, fatty acid alkanolamides and fatty acid glucamides,
- $C_8$-$C_{22}$-alkyl mono- and oligoglycosides and ethoxylated analogs thereof, where degrees of oligomerization of from 1.1 to 5, in particular 1.2 to 2.0, and glucose as sugar component are preferred,
- mixtures of alkyl (oligo)glucosides and fatty alcohols, for example the commercially available product Montanov® 68,
- addition products of from 5 to 60 mol of ethylene oxide onto castor oil and hydrogenated castor oil,
- partial esters of polyols having 3-6 carbon atoms and saturated fatty acids having 8 to 22 carbon atoms,
- sterols. Sterols are understood as meaning a group of steroids which carry a hydroxyl group on carbon atom 3 of the steroid backbone and are isolated either from animal tissue (zoosterols) or from vegetable fats (phytosterols). Examples of zoosterols are cholesterol and lanosterol. Examples of suitable phytosterols are ergosterol, stigmasterol and sitosterol. Steryls are also isolated from fungi and yeasts, the mycosterols.
- Phospholipids. These are understood primarily as meaning the glucose phospholipids which are obtained, for example, as lecithins or phosphatidylcholines from e.g., egg yoke or plant seeds (e.g., soybeans).
- Fatty acid esters of sugars and sugar alcohols, such as sorbitol,
- polyglycerols and polyglycerol derivatives, such as, for example, polyglycerol poly-12hydroxystearate (commercial product Dehymuls® PGPH),
- linear and branched fatty acids having 8 to 30 carbon atoms and the Na, K, ammonium, Ca, Mg and Zn salts thereof.

An addition of an emulsifier known per se of the water-in-oil type in an amount of about 1-5% by weight has also proven particularly advantageous. This is a mixed ester which constitutes a condensation product of a pentaerythritol di-fatty acid ester and a citric acid di-fatty alcohol ester, as described in more detail in DE patent specification 11 65 574. Through the addition of such mixed esters, a particularly creamy, fine-bubbled foam and a pleasant skin feel is achieved upon application of the body cleansing agent.

The agents according to the invention comprise the emulsifiers preferably in amounts of 0.1-25% by weight, in particular 0.5-15% by weight, based on the total agent.

The compositions according to the invention can preferably comprise at least one nonionogenic emulsifier with an HLB value of from 8 to 18, according to the definitions given in Römpp Chemistry Lexikon (ed. J. Falbe, M. Regitz), 10th Edition, Georg Thieme Verlag Stuttgart, N.Y., (1997), p. 1764. Nonionogenic emulsifiers with an HLB value of 10-15 may be particularly preferred according to the invention.

Surface-active substances preferred according to the invention are the mild surface-active substances. The mildness of surfactants and emulsifiers can be determined using various methods. For example, the neutral red test, the HET-CAM test, the human skin model or the BUS (bovine udder skin) model are used for this purpose. A common feature of all of the test methods is that measurement is, n principle, made against a standard on which the results are based.

According to these test methods, the following preferred surface-active substances have proven to be mild to particularly mild:

- ethercarboxylic acids of the formula R—O—($CH_2$—$CH_2O)_x$—$CH_2$—COOH, in which R is a linear alkyl group having 8 to 30 carbon atoms and x=0 or 1 to 16,
- acyl sarcosides having 8 to 24 carbon atoms in the acyl group,
- acyl taurides having 8 to 24 carbon atoms in the acyl group,
- acyl isethionates having 8 to 24 carbon atoms in the acyl group,
- sulfosuccinic acid mono- and dialkyl esters having 8 to 24 carbon atoms in the alkyl group and sulfosuccinic acid monoalkyl polyoxyethyl esters having 8 to 24 carbon atoms in the alkyl group and 1 to 6 oxyethyl groups,
- esters of tartaric acid and citric acid with alcohols, which constitute addition products of about 2-15 molecules of ethylene oxide and/or propylene oxide onto fatty alcohols having 8 to 22 carbon atoms,
- alkyl and/or alkenyl ether phosphates of the formula (E1-I),
- monoglyceride sulfates and monoglyceride ether sulfates of the formula (E1-III),
- amide ether carboxylic acids as described in EP 0 690 044,
- condensation products of a water-soluble salt of a water-soluble protein hydrolysate-fatty acid condensation product,
- addition products of from 5 to 60 mol of ethylene oxide onto castor oil and hydrogenated castor oil,
- polyol fatty acid esters, such as, for example, the commercial product Hydragen® HSP (Cognis) or Sovermol grades (Cognis),
- amine oxides,
- hydroxy mixed ethers, as are described, for example, in DE-A 19738866,
- sorbitan fatty acid esters and addition products of ethylene oxide onto sorbitan fatty acid esters, such as, for example, the polysorbates,
- sugar fatty acid esters and addition products of ethylene oxide onto sugar fatty acid esters,
- addition products of ethylene oxide onto fatty acid alkanolamides and fatty amines, sugar surfactants of the alkyl and alkenyl oligoglycoside type according to formula (E4-II),
- ester quats,
- alkylamidoamines and quaternized alkylamidoamines.
- $C_8$-$C_{22}$-alkyl mono- and oligoglycosides and ethoxylated analogs thereof, where degrees of oligomerization of from 1.1 to 5, in particular 1.2 to 2.0, and glucose as sugar component are preferred,
- mixtures of alkyl (oligo)glucosides and fatty alcohols, for example the commercially available product Montanov® 68,
- addition products of from 5 to 60 mol of ethylene oxide onto castor oil and hydrogenated castor oil,
- partial esters of polyols having 3-6 carbon atoms with saturated fatty acids having 8 to 22 carbon atoms,
- sterols, sterols is understood as meaning a group of steroids which carry a hydroxyl group on carbon atom 3 of the steroid backbone and are isolated either from animal tissue (zoosterols) or from vegetable fats (phytosterols). Examples of zoosterols are cholesterol and lanosterol. Examples of suitable phytosterols are ergosterol, stigmasterol and sitosterol. Steryls are also isolated from fungi and yeasts, the mycosterols.
- Phospholipids. These are understood primarily as meaning the glucose phospholipids, which are obtained, for example, as lecithins or phosphatidylcholines from e.g., egg yoke or plant seeds (e.g., soybeans).
- Fatty acid esters of sugars and sugar alcohols, such as sorbitol,
- polyglycerols and polyglyerol derivatives, such as, for example, polyglycerol poly-12-hydroxystearate (commercial product Dehymuls® PGPH).

The teaching according to the invention also encompasses the fact that these particularly mild surface-active substances can either be used individually or else mixed in the active ingredient combination according to the invention.

A very particular advantage of using these particular surface-active substances in the compositions according to the invention is that the cosmetic agents produced therewith have quite exceptional foaming behavior, outstanding creaminess, excellent foam stability, and a very high foam volume. This is even the case if the high-foaming surface-active substances, such as, for example, alkyl sulfates or alkyl ether sulfates, are largely dispensed with. To largely dispense with alkyl ether sulfates and alkyl sulfates means that the fraction of these surface-active substances is at most 5% by weight, based on the total composition. Preferably, the fraction of alkyl ether sulfate and/or alkyl sulfate is only 2% by weight.

The agent according to the invention can furthermore comprise a protein hydrolysate and/or derivative thereof (P).

As a result, in particular an increase in the mildness and the skin compatibility, but also, if desired, a fine creamy foam is achieved upon application of the powders according to the invention. This foam, which is very fine and creamy in structure and feels extremely pleasant, is achieved here in all compositions in which in particular surface-active substances are present as further ingredients. The effectiveness of the agent according to the invention is further increased here through the simultaneous use of polymers and/or penetration agents and swelling auxiliaries. In these cases, following application of the particular composition, significantly more protein hydrolysate or derivative thereof also remains on the surface of the hair, which leads to an improved effect. As a result, the hair structure is significantly strengthened and smoothed. This effect can also be clearly demonstrated using objective effect demonstrations such as, for example, measurement of the combing forces of wet and dry hair, measurement of the tear forces or measurement of the torsion angle on the hair. Confirmation of these results can also be found in the results for the consumer tests.

Protein hydrolysates are product mixtures which are obtained by acid-, base- or enzyme-catalyzed degradation of protein. According to the invention, the term "protein hydrolysates" is also understood as meaning total hydrolysates and also individual amino acids and derivatives thereof, and mixtures of different amino acids. Furthermore, according to the invention, polymers composed of amino acids and amino acid derivatives are understood under the term "protein hydrolysates." The latter include, for example, polyalanine, polyasparagine, polyserine etc. Further examples of compounds that can be used according to the invention are L-alanyl-L-proline, polyglycine, glycyl-L-glutamine or D/L-methionine-S-methylsulfonium chloride. According to the invention, β-amino acids and derivatives thereof, such as β-alanine, anthranilic acid or hippuric acid can also be used. The molecular weight of the protein hydrolysates that can be used according to the invention is between 75, the molecular weight for glycine, and 200,000, preferably the molecular weight is 75 to 50,000 and very particularly preferably 75 to 20,000 Daltons. The present teaching according to the invention also encompasses the fact that in the case of the amino acids these may be present in the form of derivatives, such as, for example, the N-acyl derivatives, the N-alkyl or the O-esters. In the case of the N-acyl derivatives, the acyl group is a formyl radical, an acetyl radical, a propionyl radical, a butyryl radical or the radical of a straight-chain, branched or unbranched, saturated or unsaturated fatty acid with a chain length of from 8 to 30 carbon atoms. In the case of an N-alkyl derivative, the alkyl group may be linear, branched, saturated or unsaturated and has a carbon chain length of from 1 to 30 carbon atoms. In the case of the O-esters, the alcohols on which the esterification is based are methanol, ethanol, isopropanol, propanol, butanol, isobutanol, pentanol, neopentanol, isopentanol, hexanols, heptanols, caprylic or caproic alcohol, octanols, nonanols, decanols, dodecanols, lauranols, in particular saturated or unsaturated, linear or branched alcohols with a carbon chain length of from 1 to 30 carbon atoms. The amino acids can be simultaneously derivatized both on the N atom and also on the O atom. The amino acids can also be used in salt form, in particular as mixed salts together with food acids. This may be preferred according to the invention.

Examples of amino acids and derivatives thereof as protein hydrolysates according to the invention are: alanine, arginine, carnitine, creatine, cystathionine, cysteine, cystine, cystinoic acid, glycine, histidine, homocysteine, homoserine, isoleucine, lanthionine, leucine, lysine, methionine, norleucine, norvaline, ornithine, phenylalanine, proline, hydroxyproline, sarcosine, serine, threonine, tryptophan, thyronine, tyrosine, valine, aspartic acid, asparagine, glutamic acid and glutamine. Preferred amino acids are alanine, arginine, glycine, histidine, lanthionine, leucine, lysine, proline, hydroxyproline, serine and asparagine. Very particular preference is given to using alanine, glycine, histidine, lysine, serine and arginine. Glycine, histidine, lysine and serine are most preferably used.

According to the invention, protein hydrolysates either of vegetable origin or animal origin or marine or synthetic origin can be used.

Animal protein hydrolysates are, for example, elastine, collagen, keratin, silk and milk protein hydrolysates, which may also be present in the form of salts. Such products are sold, for example, under the trade names Dehylan® (Cognis), Promois® (Interorgans), Collapuron® (Cognis), Nutrilan® (Cognis), Gelita-Sol® (Deutsche Gelatine Fabriken Stoess & Co), Lexein® (Inolex)® (Croda).

According to the invention, preference is given to the use of protein hydrolysates of vegetable origin, e.g., soy, almond, pea, potato and wheat protein hydrolysates. Such products are available, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Further protein hydrolysates preferred according to the invention are of maritime origin. These include, for example, collagen hydrolysates of fish or algae, and also protein hydrolysates of mussels and pearl hydrolysates.

Pearls from mussels consist essentially of inorganic and organic calcium salts, trace elements and proteins. Pearls can be obtained in a simple manner from cultivated mussels. Mussels can be cultivated both in freshwater and also in seawater. This can have an effect on the ingredients of the pearls. According to the invention, preference is given to a pearl extract which originates from mussels cultivated in seawater or saltwater. The pearls consist largely of aragonite (calcium carbonate), conchiolin and albuminoid. The latter constituents are proteins. Furthermore, magnesium and sodium salts, inorganic silicon compounds and also phosphates are also present in pearls.

To produce the pearl extract, the pearls are pulverized. The pulverized pearls are then extracted using customary methods. Extractants that can be used for producing the pearl extracts are water, alcohols, and mixtures thereof. In this connection, water is understood as meaning either demineralized water, or seawater. Among the alcohols, preference is given here to lower alcohols, such as ethanol and isopropanol, but in particular polyhydric alcohols such as glycerol, diglycerol, triglycerol, polyglycerol, ethylene glycol, propylene glycol and butylenes glycol, either as the sole extractant or else in a mixture with demineralized water or seawater. Pearl extracts based on water/glycerol mixtures have proven particularly suitable. Depending on the extraction conditions, the pearl proteins (conciloin and albuminoid) can be present largely in the native state or already partially or largely in the form of protein hydrolysates. Preference is given to a pearl extract in which conchiolin and albuminoid are already present in partially hydrolyzed form. The essential amino acids of these proteins are glutamic acid, serine, alanine, glycine, asparatic acid and phenylalanine. In a further particularly preferred embodiment, it may be advantageous if the pearl extract is additionally enriched with at least one or more of these amino acids. In the most preferred embodiment, the pearl extract is enriched with glutamic acid, serine and leucine.

Furthermore, depending on the extraction conditions, in particular depending on the choice of extractant, a greater or lesser fraction of minerals and trace elements is present in the extract. A preferred extract comprises organic and/or inorganic calcium salts and also magnesium and sodium salts, inorganic silicon compounds and/or phosphates. A very particularly preferred pearl extract comprises at least 75%, preferably 85%, more preferably 90% and very particularly preferably 95%, of all of the ingredients of the naturally occurring pearls.

Examples of pearl extracts according to the invention are the commercial products Pearl Protein Extract BG® or Crodarom® Pearl.

In the cosmetic compositions, one of the pearl extracts described above is present in an amount of at least 0.01 to 20% by weight.

Preference is given to using amounts of the extract of from 0.01 to 10% by weight, very particularly preferably amounts of from 0.01 to 5% by weight, based on the total cosmetic composition.

A further very particular protein hydrolysate is obtained from silk.

Silk is a cosmetically very interesting fiber protein. Silk is understood as meaning the fibers of the cocoon of the mulberry silk worm (*Bombyx mori* L). The raw silk fiber consists of a double thread fibroin. Sericin holds this double fiber together as cementing substance. Silk consists of 70-80% by weight of fibroin, 19-28% by weight of sericin, 0.5-1% by weight of fat and 0.5-1% by weight of dyes and mineral constituents.

The essential constituents of sericin are, at about 46% by weight, hydroxyamino acids. The sericin consists of a group of 5 to 6 proteins. The essential amino acids of sericin are serine (Ser, 37% by weight), aspartate (Asp, 26% by weight), glycine (Gly, 17% by weight), alanine (Ala), leucine (Leu) and tyrosine (Tyr).

Water-insoluble fibroin is a type of scleroprotein with long-chain molecular structure. The main constituents of fibroin are glycine (44% by weight), alanine (26% by weight) and tyrosine (13% by weight). A further essential structural feature of fibroin is the hexapeptide sequence Ser-Gly-Ala-Gly-Ala-Gly.

Technically, it is possible in an easy way to separate the two silk proteins from one another. It is thus no surprise that both sericin and also fibroin are each known in their own right as raw materials for use in cosmetic products. Furthermore, protein hydrolysates and derivatives based on each of the individual silk proteins are known raw materials in cosmetic agents. Thus, for example, sericin is sold as such by Pentapharm Ltd. as a commercial product by the name Sericin Code 303-02. Fibroin is also much more often supplied commercially as protein hydrolysate with varying molecular weights. These hydrolysates are understood in particular as "silk hydrolysates." Thus, for example, hydrolyzed fibroin with average molecular weights between 350 and 1,000 is sold under the trade name Promois® Silk. DE 31 39 438 A1 describes colloidal fibroin solutions as additive in cosmetic agents.

The positive properties of the silk protein derivatives from sericin and fibroin are each known in their own right in the literature. Thus, the sales brochure of Pentapharm describes the cosmetic effects of sericin on the skin as irritation-relieving, hydrogenating and film-forming. The properties of a shampoo comprising sericin as care component are referred to in the "Arztlichen Kosmetologie" 17, 91-110 (1987) by W. Engel et al. The effect of a fibroin derivative is described, for example in DE 31 39 438 A1, as caring and softening for the hair. However, in none of the cited publications is there even the nearest indication of a synergistic increase in the positive effects of the silk proteins and derivatives thereof upon simultaneous use of sericin and fibroin or their derivatives and/or hydrolysates upon simultaneous use of the polyammonium-polysiloxane compound according to the invention.

According to the invention the following can preferably be used as active ingredients:
native sericin,
hydrolyzed and/or further derivatived sericin, such as, for example, commercial products with the INCI names sericin, hydrolyzed sericin, or hydrolyzed silk,
a mixture of the amino acids serine, aspartate and glycine and/or their methyl, propyl, isopropyl, butyl, isobutyl esters, their salts, such as, for example, hydrochlorides, sulfates, acetates, citrates, tartrates, where in this mixture the serine and/or derivatives thereof are present to 20-60% by weight, the aspartate and/or derivatives thereof are present to 10-40% by weight and the glycine and/or derivatives thereof are present to 5-30% by weight, with the proviso that the amounts of these amino acids and/or derivatives thereof preferably add up to 100%,
and mixtures thereof.

According to the invention, the following can furthermore be used as active ingredients:
native fibroin converted to a soluble form,
hydrolyzed and/or further derivatized fibroin, particularly partially hydrolyzed fibroin which comprises the amino acid sequence Ser-Gly-Ala-Gly-Ala-Gly as main constituent,
the amino acid sequence Ser-Gly-Ala-Gly-Ala-Gly,
a mixture of the amino acids glycine, alanine and tyrosine and/or their methyl, propyl, isopropyl, butyl, isobutyl esters, their salts, such as, for example, hydrochlorides, sulfates, acetates, citrates, tartrates, where in this mixture the glycine and/or its derivatives are present in amounts of 20-60% by weight, the alanine and its derivatives are present in amounts of 10-40% by weight and the tyrosine and its derivatives are present in amounts of 0 to 25% by weight, with the proviso that the amounts of these amino acids and/or derivatives thereof preferably add up to 100% by weight,
and mixtures thereof.

If both silk protein hydrolysates and/or derivatives thereof are used simultaneously in the compositions according to the invention of the agent according to the invention, it may be preferred according to the invention that at least one of the two silk constituents, fibroin or sericin, is used in the native form or at least in a form that has been rendered soluble. According to the invention, it is also possible to use a mixture of two or more silk protein hydrolysates and/or derivatives thereof.

If a mixture of at least two silk hydrolysates and/or derivatives thereof is used, it may be preferred according to the invention that the two silk protein hydrolysates are used in the ratio of 10:90 to 70:30, in particular 15:85 to 50:50 and very particularly 20:80 to 40:60, based on their particular contents of active substance in the preparations according to the invention.

The derivatives of the hydrolysates of sericin and fibroin include both anionic and cationized protein hydrolysates. The protein hydrolysates of sericin and fibroin according to the invention and the derivatives produced therefrom can be obtained from the corresponding proteins by chemical hydrolysis, in particular alkaline or acidic hydrolysis, by enzymatic hydrolysis and/or a combination of both types of hydrolysis. The hydrolysis of proteins generally gives a protein hydrolysate with a molecular weight distribution of about 100 Daltons ranging up to several thousand Daltons. Preference is given to those protein hydrolysates of sericin and fibroin and/or derivatives thereof whose underlying protein moiety has a molecular weight of from 100 to 25,000 Daltons, preferably 250 to 10,000 Daltons. Furthermore, cationic protein hydrolysates of sericin and fibroin are also to be understood as meaning quaternized amino acids and mixtures thereof. The quaternization of the protein hydrolysates or of the amino acids is often carried out using quaternary ammonium salts such as, for example, N,N-dimethyl-N-(n-alkyl)-N-(2-hydroxy-3-chloro-n-propyl)ammonium halides. Furthermore, the cationic protein hydrolysates can also be yet further derivatized. Typical examples of the cationic protein hydrolysates and derivatives according to the invention are the products specified under the INCI names in the "International Cosmetic Ingredient Dictionary and Handbook," (Seventh Edition 1997, The Cosmetic, Toiletry, and Fragrance Association 1101 17th Street, N.W., Suite 300, Washington, D.C. 20036-4702) and commercially available products: Cocodimonium Hydroxypropyl Hydrolyzed Silk, Cocodimonium Hydroxypropyl Silk Amino Acids, Hydroxypropyltrimonium Hydrolyzed Silk, Lauryldimonium Hydroxypropyl Hydrolyzed Silk, Steardimonium Hydroxypropyl Hydrolyzed Silk, Quaternium-79 Hydrolyzed Silk. Typical examples of the anionic protein hydrolysates and derivatives according to the invention are the products specified under the INCI names in the "International Cosmetic Ingredient Dictionary and Handbook," (Seventh Edition 1997, The Cosmetic, Toiletry, and Fragrance Association 1101 17th Street, N.W., Suite 300, Washington, D.C. 20036-4702) and commercially available products: Potassium Cocoyl Hydrolyzed Silk, Sodium Lauroyl Hydrolyzed Silk or Sodium Stearoyl Hydrolyzed Silk. Finally, typical examples of the derivatives of sericin and fibroin that can be used according to the invention are the products that are commercially available under the INCI names: Ethyl Ester of Hydrolyzed Silk and Hydrolyzed Silk PG-Propyl Methylsilanediol. Furthermore, according to the invention it is possible, although not necessarily preferred, to use the commercially available products with the INCI names Palmitoyl Oligopeptide, Palmitoyl Pentapeptide-3, Palmitoyl Pentapeptide-2, Acetyl Hexapeptide-1, Acetyl Hexapeptide-3, Copper Tripeptide-1, Hexapeptide-1, Hexapeptide-2, MEA-Hydrolyzed Silk.

In the agents used according to the invention, the silk protein hydrolysates and/or derivatives thereof are present in amounts of 0.001-10% by weight, based on the total agent. Amounts of 0.005 to 5% by weight, in particular 0.01 to 3% by weight, are very particularly preferred.

Although the use of the protein hydrolysates is preferred as such, it is also possible to use instead amino acid mixtures that may have been obtained in another way. The use of derivatives of the protein hydrolysates, for example in the form of their fatty acid condensation products, is likewise possible. Such products are sold, for example, under the names Lamepon® (Cognis), Lexein® (Inolex), Crolastin® (Croda) or Cortein® (Croda).

The teaching according to the invention encompasses all isomeric forms, such as cis, trans isomers, diastereomers and chiral isomers.

According to the invention, it is also possible to use a mixture of two or more protein hydrolysates (P).

The protein hydrolysates (P) are present in the agents in concentrations of from 0.001% by weight up to 20% by weight, preferably from 0.05% by weight up to 15% by weight and very particularly preferably in amounts of from 0.05% by weight up to 5% by weight.

Furthermore, in a very particularly preferred embodiment of the invention, the UV filters (I) can be used. As regards their structure and their physical properties, the UV filters to be used according to the invention are not subject to any general limitations. Rather, all of the UV filters that can be used in the cosmetic sector and whose absorption maximum is in the UVA region (315-400 nm), in the UVB region (280-315 mm) or in UVC region (<280 nm) are suitable. UV filters with an absorption maximum in the UVB region, in particular in the region of about 280 to about 300 nm, are particularly preferred.

The UV filters used according to the invention can be selected, for example, from substituted benzophenones, p-aminobenzoic acid esters, diphenylacrylic acid esters, cinnamate acid esters, salicylic acid esters, benzimidazoles and o-aminobenzoic acid esters.

Examples of UV filters that can be used according to the invention are 4-aminobenzoic acid, N,N,N-trimethyl-4-(2-oxoborn-3-ylidenemethyl)aniline methylsulfate, 3,3,5-trimethylcyclohexyl salicylate (homosalate), 2-hydroxy-4-methoxybenzophenone (benzophenone-3; Univul® M 40, Uvasorb®MET, Neo Heliopan®BB, Eusolex®4360), 2-phenylbenzimidazole-5-sulfonic acid and its potassium, sodium and triethanolamine salts (phenylbenzimidazolesulfonic acid; Parsol® HS; Neo Heliopan®Hydro), 3,3'-(1,4-phenylenedimethylene)bis(7,7-dimethyl-2-oxobicyclo[2.2.1] hept-1-ylmethanesulfonic acid) and salts thereof, 1-(4-tert-butyphenyl)-3-(4-methoxyphenyl)propane-1,3-dione (butylmethoxydibenzoylmethane; Parsol® 1789, Eusolex® 9020), α-(2-oxoborn-3-ylidene)toluene-4-sulfonic acid and salts thereof, ethoxylated ethyl 4-aminobenzoate (PEG-25 PABA; Uvinul®P 25), 2-ethylhexyl 4-dimethylaminobenzoate (octyl dimethyl PABA; Uvasorb®DMO, Escalol®507, Eusolex®6007), 2-ethylhexyl salicylate (octyl salicylate; Escalol®587, Neo Heliopan®OS, Uvinul®O18), isopentyl 4-methoxycinnamate (isoamyl p-methoxycinnamate; Neo Heliopan®E 1000), 2-ethylhexyl 4-methoxycinnamate (octyl methoxycinnamate; Parsol®MCX, Escalol®557, Neo Heliopan®AV), 2-hydroxy-4-methoxybenzophenone-5-sulfonic acid and the sodium salt thereof (benzophenone-4; Uvinul®MS 40; Uvasorb®S 5), 3-(4'-methylbenzylidene)-D,L-camphor (4-methylbenzylidene camphor; Parsol®5000, Eusolex®6300), 3-benzylidenecamphor, 4-isopropylbenzyl salicylate, 2,4,6-trianilino(p-carbo-2'-ethylhexyl-1'-oxy)-1, 3,5-triazine, 3-imidazol-4-ylacrylic acid and the ethyl ester thereof, polymers of N-{(2 and 4)[2-oxoborn-3-ylidenemethyl]benzyl}acrylamide, 2,4-dihydroxybenzophenone (benzophenone-1; Uvasorb®20H, Uvinul®400), 2-ethylhexyl ester of 1,1'-diphenylacrylonitrilic acid (octocrylene; Eusolex®OCR, Neo Heliopan® type 303, Uvinl®N 539 SG), menthyl o-aminobenzoate (menthyl anthranilate; Neo Heliopan®MA), 2,2',4,4'-tetrahydroxybenzophenone (benzophenone-2; Uvinul®D-50), 2,2'-dihydroxy-4,4'-dimethoxybenzophenone (benzophenone-6), 2,2'-dihydroxy-4,4'-dimethoxybenzophenone-5 sodium sulfonate and 2'-ethylhexyl 2-cyano-3,3-diphenylacrylate. Preference is given to 4-aminobenzoic acid, N,N,N-trimethyl-4-(2-oxoborn-3-ylidenemethyl)aniline methylsulfate, 3,3,5-trimethylcyclohexyl salicylate, 2-hydroxy-4-methoxybenzophenone, 2-phenylbenzimidazole-5-sulfonic acid and its potassium, sodium and triethanolamine salts, 3,3'-(1,4-phenylenedimethylene)bis(7,7-dimethyl-2-oxobicyclo[2.2.1] hept-1-ylmethanesulfonic acid) and salts thereof, 1-(4-tert-butylphenyl)-3-(4-methoxyphenyl)propane-1,3-dione, α-(2-oxoborn-3-yl-idene)toluene-4-sulfonic acid and salts thereof, ethoxylated ethyl 4-aminobenzoate, 2-ethylhexyl 4-dimethylaminobenzoate, 2-ethylhexyl salicylate, isopentyl 4-methoxycinnamate, 2-ethylhexyl 4-methoxycinnamate, 2-hydroxy-4-methoxybenzophenone-5-sulfonic acid and the sodium salts thereof, 3-(4'-methylbenzylidene)-D,L-camphor, 3-benzylidenecamphor, 4-isopropylbenzyl salicylate, 2,4,6-trianilino(p-carbo-2'-ethylhexyl-1'-oxy)-1,3,5-triazine, 3-imidazol-4-ylacrylic acid and the ethyl ester thereof, polymers of N-{(2 and 4)[2-oxoborn-3-ylidenemethyl] benzyl}acrylamide. According to the invention, very particular preference is given to 2-hydroxy-4-methoxybenzophenone, 2-phenylbenzimidazole-5-sulfonic acid and the potassium, sodium and triethanolamine salts thereof, 1-(4-tert-butylphenyl)-3-(4-methoxy-phenyl)propane-1,3-dione, 2-ethylhexyl 4-methoxycinnamate and 3-(4'-methylbenzylidene)-D,L-camphor.

Preference is given to those UV filters whose molar extinction coefficient at the absorption maximum is above 15,000, in particular above 20,000.

Furthermore, it has been found that in the case of structurally similar UV filters, in many cases the water-insoluble compound within the scope of the teaching according to the invention has the higher effect compared with those water-soluble compounds which differ from it by virtue of one or more additional ionic groups. For the purposes of the invention, water-insoluble is to be understood as meaning those UV filters which dissolve in water at 20° C. to not more than 1% by weight, in particular to not more than 0.1% by weight.

Furthermore, these compounds should be soluble in customary cosmetic oil components at room temperature to at least 0.1% by weight, in particular to at least 1% by weight. The use of water-insoluble UV filters can therefore be preferred according to the invention.

According to a further embodiment of the invention, preference is given to those UV filters which have a cationic group, in particular a quaternary ammonium group.

These UV filters have the general structure U-Q.

The structural moiety U here is a group that absorbs UV rays. This group can in principle be derived from the known above-mentioned UV filters that can be used in the cosmetics sector by replacing a group, generally a hydrogen atom, of the UV filter by a cationic group Q, in particular by a quaternary ammonium function.

Compounds from which the structural moiety U can be derived are, for example,
   substituted benzophenones,
   p-aminobenzoic acid esters,
   diphenylacrylic acid esters,
   cinnamic acid esters,
   salicylic acid esters,
   benzimidazoles and
   o-aminobenzoic acid esters.

Structural moieties U which are derived from the cinnamide or from the N,N-dimethylaminobenzamide are preferred according to the invention.

The structural moieties U can in principle be chosen so that the absorption maximum of the UV filters can lie either in the UVA region (315-400 nm) or in the UVB region (280-315 nm) or in the UVC region (<280 nm). UV filters with an absorption maximum in the UVB region, in particular in the range from about 280 to about 300 nm, are particularly preferred.

Furthermore, the structural moiety U is selected, also depending on structural moiety Q, preferably such that the molar extinction coefficient of the UV filter at the absorption maximum is above 15,000, in particular above 20,000.

The structural moiety Q contains, as cationic group, preferably a quaternary ammonium group. This quaternary ammonium group can in principle be bonded directly to the structural moiety U such that the structural moiety U constitutes one of the four substituents of the positively charged nitrogen atom. However, one of the four substituents on the positively charged nitrogen atom is preferably a group, in particular an alkylene group having 2 to 6 carbon atoms, which functions as linkage between the structural moiety U and the positively charged nitrogen atom.

Advantageously, the group Q has the general structure $-(CH_2)_x-N^+R^1R^2R^3X^-$, in which x is an integer from 1 to 4, $R^1$ and $R^2$, independently of one another, are $C_{1-4}$-alkyl groups, $R^3$ is a $C_{1-22}$-alkyl group or a benzyl group and $X^-$ is a physiologically compatible anion. Within the context of this general structure, x is preferably 3, $R^1$ and $R^2$ are in each case a methyl group, and $R^3$ is either a methyl group or a saturated or unsaturated, linear or branched hydrocarbon chain having 8 to 22, in particular 10 to 18, carbon atoms.

Physiologically compatible anions are, for example, inorganic anions, such as halides, in particular chloride, bromide and fluoride, sulfate ions and phosphate ions, and also organic anions, such as lactate, citrate, acetate, tartrate, methosulfate and tosylate.

Two preferred UV filters with cationic groups are the compounds, available as commercial products, cinnamic acid amidopropyltrimethylammonium chloride (Incroquat® UV-283) and dodecyldimethylaminobenzamidopropyldimethylammonium tosylate (Escalol® HP 610).

The teaching according to the invention also encompasses the use of a combination of two or more UV filters. Within the scope of this embodiment, the combination of at least one water-insoluble UV filter with at least one UV filter with a cationic group is preferred.

The UV filters (I) are present in the agents used according to the invention usually in amounts of 0.1-5% by weight, based on the total agent. Amounts of 0.4-2.5% by weight are preferred.

The effect of the agents according to the invention can furthermore be increased through a 2-pyrrolidinone-5-carboxylic acid and derivatives thereof (J). The invention therefore further provides the use of derivatives of 2-pyrrolidinone-5-carboxylic acid. Preference is given to the sodium, potassium, calcium, magnesium or ammonium salts in which the ammonium ion carries one to three $C_1$- to $C_4$-alkyl groups besides hydrogen. The sodium salt is very particularly preferred. The amounts used in the agents according to the invention are 0.05 to 10% by weight, based on the total agent, particularly preferably 0.1 to 5% by weight, and in particular 0.1 to 3% by weight.

The use of vitamins, provitamins and vitamin precursors and derivatives thereof (K) has likewise proven to be advantageous. Vitamins, provitamins and vitamin precursors which are assigned to the groups A, B, C, E, F and H are particularly preferred here.

The use of the vitamins, provitamins and vitamin precursors and derivatives thereof (K) as active ingredients has likewise proven very particularly advantageous. Following treatment with these very particularly preferred components, the skin leaves behind an essentially more cared for, more vital, stronger impression with significantly improved shine and a very good feel both in the wet and also in the dry state. Furthermore, this active ingredient influences the regeneration and restructuring of the affected skin and of the stripped hair, leads to regulation of the fat level so that the skin thus treated and the hair refats more slowly and does not have a tendency towards superfatting. Additionally, this active ingredient exhibits an antiflammatory and skin-calming effect. Finally split hair is regenerated and repaired by these active ingredients. These active ingredients are able to penetrate into the hair and to strengthen and repair the hair from the inside outwards. This "repair effect" can be demonstrated objectively by means of DSC measurements. These effects can also be demonstrated subjectively, for example, in the consumer test.

The group of substances referred to as Vitamin A includes retinol (Vitamin $A_1$) and 3,4-didehydroretinol (Vitamin $A_2$). β-Carotene is the provitamin of retinol. Suitable as Vitamin A component are, according to the invention, for example Vitamin A acid and esters thereof, Vitamin A aldehyde and Vitamin A alcohol, and esters thereof, such as the palmitate and the acetate. The agents according to the invention comprise the Vitamin A component preferably in amounts of 0.05-1% by weight, based on the total preparation.

The Vitamin B group or the Vitamin B complex includes, inter alia,
   Vitamin $B_1$ (thiamine)
   Vitamin $B_2$ (riboflavin)
   Vitamin $B_3$. This name often covers the compounds nicotinic acid and nicotinamide (niacinamide). According to the invention, preference is given to nicotinamide, which is present in the agents used according to the invention preferably in amounts of 0.05 to 1% by weight, based on the total agent.
   Vitamin $B_5$ (pantothenic acid, panthenol and pantolactone). Within the scope of this group, preference is given to using panthenol and/or pantolactone. Derivatives of panthenol which can be used according to the invention are, in particular, the esters and ethers of panthenol, and also cationically derivatized panthenols. Individual representatives are, for example, panthenol triacetate, panthenol monoethyl ether and its monoacetate, and also the cationic panthenol derivatives disclosed in WO 92/13829. The specified compounds of the Vitamin $B_5$ type are present in the agents according to the invention preferably in amounts of 0.05-10% by weight, based on the total agent. Amounts of 0.1-5% by weight are particularly preferred.

Vitamin $B_6$ (pyridoxine and pyridoxamine and pyridoxal).

Vitamin C (ascorbic acid). Vitamin C is used in the agents according to the invention preferably in amounts of from 0.1 to 3% by weight, based on the total agent. Use in the form of the palmitic acid ester, the glucosides or phosphates may be preferred. Use in combination with tocopherols may likewise be preferred.

Vitamin E (tocopherols, in particular $\alpha$-tocopherol). Tocopherol and its derivatives, which include, in particular, the esters, such as the acetate, the nicotinate, the phosphate and the succinate, are present in the agents according to the invention preferably in amounts of 0.05-1% by weight, based on the total agent.

Vitamin F. The term "Vitamin F" is usually understood as meaning essential fatty acids, in particular linoleic acid, linolenic acid and arachidonic acid.

Vitamin H. Vitamin H is the compound (3aS,4S,6aR)-2-oxohexahydrothienol[3,4-d]imidazole-4-valeric acid, for which, however, the trivial name biotin has meanwhile caught on. Biotin is present in the agents according to the invention preferably in amounts of from 0.0001 to 1.0% by weight, in particular in amounts of from 0.001 to 0.01% by weight.

Preferably, the agents according to the invention comprise vitamins, provitamins and vitamin precursors from groups A, B, E and H. Panthenol, pantolactone, pyridoxine and its derivatives, and also nicotinamide and biotin are particularly preferred.

Finally, further synergistic advantages arise through the use of plant extracts (L) in the compositions according to the invention. The use of these substances is therefore particularly advantageous.

Combinations of this type bring about a pleasant scent both of the shaped cosmetic composition and also of the skin and hair treated therewith. In this connection, it may even be possible to dispense with the addition of further perfume oils and fragrances.

Furthermore, this active ingredient combination according to the invention also has a favorable influence on the moisture level in the skin. Furthermore, it exhibits an anti-inflammatory and skin-calming effect if, for example, camomile or valerian is used.

Usually, these extracts are produced by extraction of the whole plant. However, in individual cases, it may also be preferred to produce the extracts exclusively from flowers and/or leaves of the plant.

With regard to the plant extracts that can be used according to the invention, reference is made in particular to the extracts which are listed in the table starting on page 44 of the 3rd Edition of the introduction to the ingredients declaration of cosmetic agents, published by the Industrieverband Körperpflege-und Waschmittel e.V. (IKW), Frankfurt.

According to the invention, the extracts from green tea, oak bark, stinging nettle, hamamelis, hops, henna, camomile, burdock, horsetail, hawthorn, linden blossom, almond, aloe vera, spruce needle, horse chestnut, sandalwood, juniper, coconut, mango, apricot, lime, wheat, kiwi, melon, orange, grapefruit, sage, rosemary, birch, mallow, valerian, lady's smock, wild thyme, yarrow, thyme, Melissa, restharrow, coltsfoot, marshmallow, meristem, ginseng, coffee, cocoa, moringa and ginger root, in particular, are preferred.

Particular preference is given to the extracts from green tea, oak bark, stinging nettle, hamamelis, hops, camomile, burdock, horsetail, linden blossom, almond, aloe vera, coconut, mango, apricot, lime, wheat, kiwi, melon, orange, grapefruit, sage, rosemary, birch, lady's smock, wild thyme, yarrow, valerian, coffee, cocoa, moringa, restharrow, meristem, ginseng and ginger root.

Of very particular suitability for the use according to the invention are the extracts from green tea, almond, aloe vera, coconut, mango, apricot, lime, wheat, kiwi and melon.

Extractants for producing the specified plant extracts which may be used are water, alcohols and mixtures thereof. Among the alcohols, preference is given here to lower alcohols, such as ethanol and isopropanol, but in particular polyhydric alcohols, such as ethylene glycol and propylene glycol, both as the sole extractant or else in a mixture with water. Plant extracts placed on water/propylene glycol in the ratio 1:10 to 10:1 have proven to be particularly suitable.

According to the invention, the plant extracts can be used either in pure form or in dilute form. If they are used in dilute form, they usually comprise about 2-80% by weight of active substance and, as solvent, the extractant or extractant mixture used during their isolation.

In addition, it may be preferred to use mixtures of two or more, in particular of two, different plant extracts in the agents according to the invention.

Additionally, it may prove advantageous if penetration auxiliaries and/or swelling agents (M) are present in the agents according to the invention. These auxiliaries ensure better penetration of active ingredients into the keratin fibers or help the keratin fibers to swell. These include, for example, urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol propylene glycol ethers, for example propylene glycol monoethyl ethers, carbonates, hydrogen carbonates, diols and triols, and in particular 1,2-diols and 1,3-diols such as, for example, 1,2-propanediol, 1,2-pentanediol, 1,2-hexanediol, 1,2-dodecanediol, 1,3-propanediol, 1,6-hexaendiol, 1,5-pentanediol, 1,4-butanediol.

Finally, experimental findings show that the agents according to the invention are particularly highly suitable for depositing perfume oils or fragrances on the skin and the hair in an increased amount. At the same time, the perfume oils and fragrances remain on the skin or the hair much longer. This leads to increased acceptance of such compositions with the consumer. These results are particularly relevant for compositions such as styling products and hair-fixing and hair-setting products.

A further group of very particularly preferred further ingredients of cosmetic compositions comprising the active ingredient combination (A) according to the invention are perfumes. The excellent and completely surprisingly positive results of compositions comprising the active ingredient combination (A) according to the invention and perfumes have already been described in detail above.

The term "perfume" means perfume oils, fragrances and odorants. Perfume oils that may be mentioned are mixtures of natural and synthetic odorants.

Natural odorants are extracts of flowers (lily, lavender, rose, jasmine, neroli, ylang ylang), stems and leaves (geranium, petuli, petitgrain), fruits (anise, coriander, caraway, juniper), fruit peels (bergamot, lemon, orange), roots (mace, angelica, celery, cardamom, costus, iris, calmus), woods (pinewood, sandalwood, guaiac wood, cedar wood, rosewood), herbs and grasses (tarragon, lemongrass, sage, thyme, camomile), needles and branches (spruce, fir, pine, dwarf-pine), resins and balsams (galbanum, elemi, benzoe, myrrh, olibanum, opoponax).

Also suitable are animal raw materials, such as, for example, civet and castoreum.

Typical synthetic odorant compounds are products of the ester type, ether type, aldehyde type, ketone type, alcohol type and hydrocarbon type. Odorant compounds of the ester type are, for example, benzyl acetate, phenoxyethyl isobutyrate, p-tert-butylcyclohexyl acetate, linalyl acetate, dimethyl benzyl carbinyl acetate, phenylethyl acetate, linalyl benzoate, benzyl formate, ethylmethyl phenylglycinate, allyl cyclohexyl propionate, styrallyl propionate, cyclohexyl salicylate, floramat, melusate, jasmecyclate and benzyl salicylate. The ethers include, for example, benzyl ethyl ether and ambroxan, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethol, citronellol, eugenol, isoeugenol, geraniol, linalool, phenylethyl alcohol and terpineol, and the hydrocarbons include primarily the terpenes and balsams such as limonene and pinene.

However, preference is given to using mixtures of different odorants which together produce a pleasing scent note. Essential oils of relatively low volatility, which are mostly used as aroma components, are also suitable as perfume oils, e.g., sage oil, camomile oil, oil of cloves, Melissa oil, mint oil, cinnamon leaf oil, linden blossom oil, juniperberry oil, vetiver oil, oliban oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange blossom oil, orange peel oil, sandalwood oil, neroliol, allyl amyl glycolate, cyclovertal, lavandin oil, clary sage oil, β-damascone, geranium oil bourbon, cyclohexyl salicylate, Vertofix Coeur, Iso-E-Super, Fixolide NP, evernly, iraldein gamma, phenylacetic acid, geranyl acetate, benzyl acetate, rose oxide, romillate, irotyl and floramat, alone or in mixtures.

Further examples of odorants which may be in the compositions according to the invention can be found, for example, in S. Arctander, Perfume and Flavor Materials, vol. I and II, Montclair, N.J., 1969, self-published, or K. Bauer, D. Garbe and H. Surburg, Common Fragrance and Flavor Materials, 3rd Edition, Wiley-VCH, Weinheim 1997.

In order to be detectable, an odorant must be volatile where, besides the nature of the functional groups and the structure of the chemical compound, the molar mass also plays an important role. Thus, most odorants have molar masses up to about 200 Daltons, whereas molar masses of 300 Daltons and above are more of an exception. On account of the varying volatility of odorants, the odor of a perfume or fragrance composed of two or more odorants changes during evaporation, the odor impressions being divided into top note, middle note or body, and end note or dry out. Since the odor perception is also based to a large degree on the odor intensity, the top note of a perfume or fragrance does not consist merely of relatively volatile compounds, while the end note consists to a large degree of less volatile, i.e. tenacious, odorants.

Tenacious odorants which can advantageously be used for the purposes of the present invention are, for example, the essential oils, such as angelica root oil, anise oil, arnica flowers oil, basil oil, bay oil, bergamot oil, champak blossom oil, noble fir oil, noble fir cone oil, elemi oil, eucalyptus oil, fennel oil, pine needle oil, galbanum oil, geranium oil, ginger grass oil, guaiac wood oil, gurjun balsa oil, helichrysum oil, ho oil, ginger oil, iris oil, cajeput oil, calmus oil, camomile oil, camphor oil, canaga oil, cardamom oil, cassia oil, scotch fir oil, copaiba balsam oil, coriander oil, spearmint oil, caraway oil, cumin oil, lavender oil, lemon grass oil, lime oil, mandarin oil, Melissa oil, ambrette oil, myrrh oil, oil of cloves, neroli oil, niaouli oil, olibanum oil, orange oil, origanum oil, palmarosa oil, patchouli oil, peru balsam oil, petitgrain oil, pepper oil, peppermint oil, pimento oil, pine oil, rose oil, rosemary oil, sandalwood oil, celery oil, lavender spike oil, star anise oil, terpentine oil, thuja oil, thyme oil, verbena oil, vetiver oil, juniperberry oil, absinth oil, wintergreen oil, ylang ylang oil, ysop oil, cinnamon oil, cinnamon leaf oil, citronellol, lemon oil, and cypress oil.

However, the higher-boiling or solid odorants of natural or synthetic origin can also advantageously be used for the purposes of the present invention as tenacious odorants or odorant mixtures, i.e. fragrances. These compounds include the compounds specified below, and mixtures thereof: ambrettolide, -amylcinnamaldehyde, anethole, anisaldehyde, anise alcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valerate, borneol, bornyl acetate, -bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, methyl heptynecarboxylate, heptaldehyde, hydroquinone dimethyl ether, hydroxycinnamaldehyde, hydroxycinanmyl alcohol, indole, irone, isoeugenol, isoeugenol methyl ether, isosafrol, jasmone, camphor, carvacrol, carvone, p-cresol methyl ether, coumarin, p-methoxyacetophenone, methyl n-amyl ketone, methyl methylanthranilate, p-methylacetophenone, methyl chavicol, p-methylquinoline, methyl naphthyl ketone, methyl-n-nonylacetaldehyde, methyl-n-nonyl ketone, muscone, -naphthol ethyl ether, -naphthol methyl ether, nerol, nitrobenzene, n-nonylaldehyde, nonyl alcohol, n-octylaldehyde, p-oxyacetophenone, pentadecanolide, -phenylethyl alcohol, phenylacetaldehyde dimethyl acetal, phenylacetic acid, pulegone, safrol, isoamyl salicylate, methyl salicylate, hexyl salicylate, cyclohexyl salicylate, santalol, scatol, terpineol, thymene, thymol, -undelactone, vanillin, veratrum aldehyde, cinnamaldehyde, cinnamyl alcohol, cinnamic acid, ethyl cinnamate, benzyl cinnamate.

The more readily volatile odorants which can advantageously be used for the purposes of the present invention include, in particular, the lower-boiling odorants of natural or synthetic origin which can be used alone or in mixtures. Examples of readily volatile odorants are alkyl isothiocyanates (alkyl mustard oils), butanedione, limonene, linalool, linayl acetate and propionate, menthol, methone, methyl-n-heptenone, phellandrene, phenylacetaldehyde, terpinyl acetate, citral, citronellal.

All of the above-mentioned odorants can be used on their own or in a mixture according to the present invention with the advantages already given.

If the boiling points of the individual odorants are significantly below 300° C., then a preferred embodiment of the invention is present where preferably at least 50% of the contained fragrances have a boiling point below 300° C., advantageously at least 60%, in a further advantageous manner at least 70%, in a yet more advantageous manner at least 80%, in an entirely advantageous manner at least 90%, in particular even 100%.

Boiling points below 300° C. are advantageous because the fragrances in question would have too low a volatility at higher boiling points. However, in order to be able to "exude" at least proportionately from the particle and to develop scent, a certain volatility of the fragrances is advantageous.

It has already been observed earlier that some unstable perfume constituents are sometimes not readily compatible with carrier material and, following incorporation into the carrier, decompose at least proportionately, particularly if the carrier is a porous mineral carrier, such as, for example, clay, or zeolite, in particular dehydrated and/or activated zeolite. Unstable fragrances for the purposes of this invention can be identified by incorporating a perfume composition comprising at least 6 fragrances in activated/dehydrated zeolite X and storing the resulting sample for 24 hours at room temperature. The fragrances are then extracted with acetone and analyzed by means of gas chromatography in order to determine the stability. For the purposes of this invention, a fragrance is termed unstable if at least 50% by weight, preferably at least 65% by weight, advantageously at least 80% by weight, in particular at least 95% by weight, of the fragrance have decomposed into degradation products and cannot be produced again during the extraction.

If less than 15% by weight, preferably less than 8% by weight, advantageously less than 6% by weight, more advantageously less than 3% by weight, of unstable perfume are present in the agent according to the invention, based on the total amount of perfume, which is ad/absorbed in/on the particles, then a preferred embodiment of the invention is present where the unstable perfume includes in particular the group of allyl alcohol esters, esters of secondary alcohols, esters of tertiary alcohols, allylic ketones, condensation products of amines and aldehydes, acetals, ketals and mixtures of the above.

If the perfume which is ad/absorbed in/on the particles comprises at least 4, advantageously at least 5, in a further advantageous manner at least 6, in a yet further advantageous manner at least 7, in a yet more advantageous manner at least 8, preferably at least 9, in particular at least 10, different odorants, then a preferred embodiment of the invention is present.

If the logP value of the perfume components which are ad/absorbed in/on the particles is essentially at least 2, preferably at least 3 or more, so that thus at least 40%, advantageously at least 50%, in a further advantageous manner at least 60%, in a yet more advantageous manner at least 70%, preferably at least 80%, in particular 90%, of the perfume components satisfy this log requirement, then a preferred embodiment of the invention is present.

The logP value is a measure of the hydrophobicity of the perfume components. It is the $\log^{10}$ of the partition coefficient between n-octanol and water. The octanol/water partition coefficient of a perfume constituent is the ratio between its equilibrium concentrations in water and octanol. A perfume constituent with a higher partition coefficient P is more hydrophobic. The specified conditions for the logP are therefore advantageous because it is thereby ensured that the fragrances can be better retained in the pores of the carrier material and also better precipitate onto objects which are treated with the particles (for example directly through treatment with a detergent formulation which comprises the particles according to the invention). The logP value of many perfume constituents is quoted in the literature; for example, the Pomona 92 database, available from Daylight Chemical Information Systems, Inc. (Daylog CIS), Irvine, Calif., contains many such values together with references to the original literature. The logP values can also be calculated, for example with the "ClogP" program from the above-mentioned company Daylight CIS. For calculated logP values, the term used is usually "ClogP values." Within the scope of this invention, the term "logP values" also includes the ClogP values. Preferably, ClogP values should then be used for estimating hydrophobicity if there are no experimental logP values for certain perfume constituents.

If desired, the perfume can also be combined with a perfume fixative. It is assumed that perfume fixatives are able to slow the evaporation of the more highly volatile fractions of perfumes.

According to a further preferred embodiment, the perfume which is ab/adsorbed in/on the carrier material includes a perfume fixative, preferably in the form of diethyl phthalates, musk (derivatives), and mixtures of these, the amount of fixative being preferably 1 to 55% by weight, advantageously 2 to 50% by weight, more advantageously 10 to 45% by weight, in particular 20 to 40% by weight, of the total amount of perfume.

According to a further preferred embodiment, the particles comprise an agent that increases the viscosity of liquids, in particular of perfume, preferably PEG (polyethylene glycol), advantageously with a molecular weight of from 400 to 2,000, where the agent increasing the viscosity is present preferably in amounts of from 0.1 to 20% by weight, advantageously from 0.15 to 10% by weight, in a further advantageous manner from 0.2 to 5% by weight, in particular from 0.25 to 3% by weight, based on the particles.

It has been found that agents increasing the viscosity of liquids, in particular of perfume, make a further contribution to the stabilization of the perfume in the particles if nonionic surfactant is present at the same time.

Agents increasing the viscosity are preferably polyethylene glycols (abbreviation: PEG), which can be described by the general formula (I):

$$H-(O-CH_2-CH_2)_n-OH \qquad (I),$$

in which degree of polymerization n can vary from about 5 up to >100,000, corresponding to molar masses from 200 to 5,000,000 gmol$^{-1}$. The products with molar masses below 25,000 g/mol are referred to here as actual polyethylene glycols, whereas high molecular weight products are often referred to in the literature as polyethylene oxides (abbreviation: PEOX). The preferably used polyethylene glycols can have a linear or branched structure, with linear polyethylene glycols in particular being preferred, and be terminally capped.

Particularly preferred polyethylene glycols include those with relative molecular masses between 400 and 2,000. In particular, it is also possible to use polyethylene glycols which are per se present in liquid state at room temperature and a pressure of 1 bar; we are talking here primarily of polyethylene glycol with a relative molecular mass of 200, 400 and 600.

The perfumes are generally added to the total composition in an amount of from 0.05 to 5% by weight, preferably from 0.1 to 2.5% by weight, particularly preferably from 0.2 to 1.5% by weight, based on the total composition.

The perfumes can be added to the compositions in liquid form, neat or diluted with a solvent for perfumings. Suitable solvents for this are, for example, ethanol, isopropanol, diethylene glycol monoethyl ether, glycerol, propylene glycol, 1,2-butylene glycol, dipropylene glycol, diethyl phthalate, triethyl citrate, isopropyl myristate etc.

Furthermore, the perfumes for the compositions according to the invention can be adsorbed on a carrier substance which ensures both fine distribution of the odorants within the product and also controlled release upon use. Carriers of this type may be porous inorganic materials such as light sulfate, silica gels, zeolites, gypsums, clays, clay granules, aerated concrete etc., or organic materials, such as woods or cellulose-based materials.

The perfume oils for the compositions according to the invention can also be present in microcapsulated form, spray-dried form, as inclusion complexes or as extrusion products and be added to the compositions to be perfumed in this form.

Optionally, the properties of the perfume oils modified in this way can be further optimized with regard to a more targeted scent release by "coating" with suitable materials, for which purpose preferably wax-like plastics, such as, for example, polyvinyl alcohol, are used.

The consumer may, upon perceiving the cosmetic compositions, in particular caused by an esthetically pleasing packaging, optionally in combination with aromatic scent notes, associate the composition according to the invention with a food such as, for example, confectionary or beverages. As a result of this association, it is not impossible, especially with children, to in principle rule out oral administration or swallowing of the cosmetic composition. In a preferred embodiment, therefore, the compositions according to the invention comprise a bitter substance in order to prevent swallowing or accidental ingestion. According to the invention, preference is given here to bitter substances which are soluble in water at 20° C. to at least 5 g/l.

As regards an undesired interaction with scent components that may be present in the cosmetic compositions, in particular a change in the scent note perceived by the consumer, the ionogenic bitter substances have proven superior to the non-ionogenic substances. Ionogenic bitter substances, preferably consisting of organic cation(s) and organic anion(s), are therefore preferred for the preparations according to the invention.

Bitter substances that are exceptionally suitable according to the invention are quaternary ammonium compounds which contain an aromatic group both in the cation and also in the anion. Such a compound is the benzyldiethyl((2,6-xylylcarbamoyl)methyl)ammonium benzoate commercially available, for example, under the trade name Bitrex® and Indigestin®. This compound is also known under the name denatonium benzoate.

The bitter substance is present in the shaped bodies according to the invention in amounts of from 0.0005 to 0.1% by weight, based on the shaped body. Particular preference is given to amounts of from 0.001 to 0.05% by weight.

For the purposes of the invention, short-chain carboxylic acids (N) can advantageously additionally have a supporting effect. For the purposes of the invention, short-chain carboxylic acids and derivatives thereof are understood as meaning carboxylic acids which may be saturated or unsaturated and/or straight-chain or branched or cyclic and/or aromatic and/or heterocyclic and have a molecular weight of less than 750. For the purposes of the invention, preference may be given to those saturated or unsaturated straight-chain or branched carboxylic acids with a chain length of from 1 to 16 carbon atoms in the chain, and very particular preference to those with a chain length of from 1 to 12 carbon atoms in the chain.

For the purposes of the invention, short-chain carboxylic acids (N) can advantageously be used as ingredient b) in the active ingredient complex (A). For the purposes of the invention, short-chain carboxylic acids and derivatives thereof are understood as meaning carboxylic acids which may be saturated or unsaturated and/or straight-chain or branched or cyclic and/or aromatic and/or heterocyclic and have a molecular weight of less than 750. For the purposes of the invention, preference may be given to saturated or unsaturated straight-chain or branched carboxylic acids with a chain length of from 1 to 16 carbon atoms in the chain, and very particular preference to those with a chain length of from 1 to 12 carbon atoms in the chain.

One use of the short-chain carboxylic acids is the adjustment of the pH of the cosmetic compositions according to the invention. However, the active ingredient complex (A) according to the invention leads to improved skin smoothness and to improved skin structure and also to a smoothed hair structure.

Besides the short-chain carboxylic acids themselves according to the invention and listed above by way of example, it is also possible to use their physiologically compatible salts according to the invention. Examples of such salts are the alkali metal, alkaline earth metal, zinc salts and ammonium salts, which, for the purposes of the present application, are to be understood as including the mono-, di- and trimethyl-, -ethyl- and -hydroxyethyl-ammonium salts. However, it is likewise possible to also use acids neutralized with alkaline-reacting amino acids, such as, for example, arginine, lysine, ornithine and histidine. The sodium, potassium, ammonium and arginine salts are preferred salts. Furthermore, for formulation reasons, it may be preferred to select the carboxylic acid as active ingredient (b) from the water-soluble representatives, in particular the water-soluble salts.

The very particularly preferred active ingredients (b) according to the invention include the hydroxycarboxylic acids and in turn here in particular the dihydroxy-, trihydroxy- and polyhydroxycarboxylic acids, and also the dihydroxy-, trihydroxy- and polyhydroxy-di-, tri- and polycarboxylic acids.

Examples of particularly suitable hydroxycarboxylic acids are glycolic acid, glyceric acid, lactic acid, malic acid, tartaric acid or citric acid. The teaching according to the invention also encompasses that these acids are used in the form of mixed salts, for example with amino acids. This may be preferred according to the invention.

The teaching according to the invention encompasses all isomeric forms, such as cis, transisomers, diastereomers and chiral isomers.

According to the invention, it is also possible to use a mixture of two or more active ingredients (b).

For the purposes of the invention, the short-chain carboxylic acids can have one, two, three or more carboxy groups. For the purposes of the invention, preference is given to carboxylic acids with two or more carboxy groups, in particular di- and tricarboxylic acids. The carboxy groups can be present completely or partially as ester, acid anhydride, lactone, amide, imidic acid, lactam, lactim, dicarboximide, carbohydrazide, hydrazone, hydroxam, hydroxime, amidine, amide oxime, nitrile, phosphonic or phosphate ester. The carboxylic acids according to the invention can be substituted along the carbon chain or the ring backbone. The substituents of the carboxylic acids according to the invention are to include, for example, $C_1$-$C_8$-alkyl, $C_2$-$C_8$-alkenyl, aryl, aralkyl and aralkenyl, hydroxymethyl, $C_2$-$C_8$-hydroxyalkyl, $C_2$-$C_8$-hydroxyalkenyl, aminomethyl, $C_2$-$C_8$-aminoalkyl, cyano, formyl, oxo, thioxo, hydroxyl, mercapto, amino, carboxy or imino groups. Preferred substituents are $C_1$-$C_8$-alkyl, hydroxymethyl, hydroxyl, amino and carboxy groups. Particular preference is given to substituents in the □ position. Very particularly preferred substituents are hydroxy, alkoxy and amino groups, where the amino function may optionally be further substituted by alkyl, aryl, aralkyl and/or alkenyl radicals. Furthermore, likewise preferred carboxylic acid derivatives are the phosphonic and phosphate esters.

Examples of carboxylic acids according to the invention are formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluoyl acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-naphthalenepentaacetic acid, malonaldehydic acid, 4-hydroxyphthalamidic acid, 1-pyrazolecarboxylic acid, gallic acid or propanetricarboxylic acid, a dicarboxylic acid selected from the group formed by compounds of the general formula (N-I):

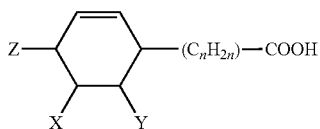

(N-I)

in which Z is a linear or branched alkyl or alkenyl group having 4 to 12 carbon atoms, n is a number from 4 to 12, and one of the two groups X and Y is a COOH group and the other is hydrogen or a methyl or ethyl radical, dicarboxylic acids of the general formula (N-I) which additionally also carry 1 to 3 methyl or ethyl substituents on the cyclohexene ring, and dicarboxylic acids which are formed from the dicarboxylic acids according to formula (N-I) formally by addition of one molecule of water onto the double bond in the cyclohexene ring.

Dicarboxylic acids of the formula (N-I) are known in the literature.

A preparation process can be found, for example, in U.S. Pat. No. 3,753,968. The German patent specification 22 50 055 discloses the use of these dicarboxylic acids in liquid soap masses. The German laid-open specification 28 33 291 discloses deodorizing agents which comprise zinc salts or magnesium salts of these dicarboxylic acids. Finally, the German laid-open specification 35 03 618 discloses agents for washing and rinsing the hair in which, through addition of these dicarboxylic acids, a noticeably improved hair cosmetic effect of the water-soluble ionic polymers present in the agent is obtained. Finally, the German laid-open specification 197 54 053 discloses hair-treatment agents which have care effects.

The dicarboxylic acids of the formula (N-I) can be prepared, for example, by reacting polyunsaturated dicarboxylic acids with unsaturated monocarboxylic acids in the form of a Diels-Alder cyclization. The process usually starts from a polyunsaturated fatty acid as dicarboxylic acid component. Preference is given to the linoleic acid obtainable from natural fats and oils. As monocarboxylic acid component, preference is given in particular to acrylic acid, but also, for example, methacrylic acid and crotonic acid. Usually, in reactions according to Diels-Alder, isomer mixtures are formed in which one component is present in excess. According to the invention, these isomer mixtures can be used just as much as the pure compounds.

Besides the preferred dicarboxylic acids according to formula (N-I), according to the invention it is also possible to use those dicarboxylic acids which differ from the compounds according to formula (N-I) by 1 to 3 methyl or ethyl substituents on the cyclohexyl ring or are formed from these compounds formally by adding one molecule of water to the double bond of the cyclohexene ring.

The dicarboxylic acid (mixture) which forms by reacting linoleic acid with acrylic acid has proven particularly effective according to the invention. This is a mixture of 5- and 6-carboxy-4-hexyl-2-cyclohexene-1-octanoic acid. Such compounds are commercially available under the names WestvacoDiacid® 1550 and Westvaco Diacid® 1595 (manufacturer: Wetsvaco).

Besides the short-chain carboxylic acids according to the invention themselves and listed above by way of example, it is also possible to use their physiologically compatible salts according to the invention. Examples of such salts are the alkali metal, alkaline earth metal, zinc salts and also ammonium salts, which, for the purposes of the present application are understood to include the mono-, di- and trimethyl-, -ethyl- and -hydroxyethyl-ammonium salts. However, for the purposes of the invention, very particular preference may be given to using acids neutralized with alkali-reacting amino acids, such as, for example, arginine, lysine, ornithine and histidine. Furthermore, it may be preferred, for formulation reasons, to select the carboxylic acid from the water-soluble representatives, in particular the water-soluble salts.

Furthermore, it is preferred according to the invention to use hydroxycarboxylic acids and here in turn in particular the dihydroxy, trihydroxy and polyhydroxycarboxylic acids, and also the dihydroxy-, trihydroxy- and polyhydroxy-di-, tri- and polycarboxylic acids together in the agents. In this connection, it has been found that, besides the hydroxycarboxylic acids, also the hydroxycarboxylic acid esters and also the mixtures of hydroxycarboxylic acids and esters thereof may be very particularly preferred. Preferred hydroxycarboxylic acid esters are, for example, full esters of glycolic acid, lactic acid, malic acid, tartaric acid or citric acid. Further fundamentally suitable hydroxycarboxylic acid esters are esters of β-hydroxypropionic acid, of tartronic acid, of D-gluconic acid, of sugar acid, of mucic acid or of glucuronic acid. Suitable as alcohol component of these esters are primary, linear or branched aliphatic alcohols having 8-22 carbon atoms, thus, for example, fatty alcohols or synthetic fatty alcohols. Here, the esters of C12-C15-fatty alcohols are particularly preferred. Esters of this type are commercially available, for example, under the trade name Cosmacol® from EniChem, Augusta Industriale. Particularly preferred polyhydroxypolycarboxylic acids are polylactic acid and polytartaric acid, and esters thereof.

According to the invention, it is very particularly preferred to use the food acids as short-chain carboxylic acids for the purposes of the invention.

The active ingredients (b) according to the invention are present in the agents in concentrations of from 0.01% by weight to 20% by weight, preferably from 0.05% by weight to 15% by weight and very particularly preferably in amounts of from 0.1% by weight to 5% by weight.

Further very particularly preferred nature-analogous substances of the agents according to the invention are polyhydroxy compounds.

For the purposes of the invention, polyhydroxy compounds (C) are understood as meaning all substances which meet the definition in Römpp's Lexikon of Chemistry, version 2.0 on the CD-ROM Edition of 1999, Verlag Georg Thieme. According to this, polyhydroxy compounds are to be understood as meaning organic compounds with at least two hydroxyl groups. In particular, for the purposes of the present invention, these are to be understood as including:

polyols with at least two hydroxy groups, such as, for example, trimethylolpropane, carbohydrates, sugar alcohols and sugars, and salts thereof, in particular monosaccharides, disaccharides, trisaccharides and oligosaccharides, where these may also be present in the form of aldoses, ketoses and/or lactoses, and protected by customary —OH and —NH protective groups known in the literature, such as, for example, the triflate group, the trimethylsilyl group or acyl groups, and also furthermore in the form of the methyl ethers and as phosphate esters, aminodeoxy sugars, deoxy sugars, thio sugars, where these may also be present in the form of aldoses, ketoses and/or lactoses, and also protected by customary —OH and —NH protective groups known in the literature, such as, for example, the triflate group, the trimethylsilyl group or acyl groups, and furthermore in the form of the methyl ethers and as phosphate esters.

Among these, very particular preference is given to monosaccharides having 3 to 8 carbon atoms, such as, for example, trioses, tetroses, pentoses, hexoses, heptoses and octoses, where these may be present also in the form of aldoses, ketoses and/or lactoses, and also protected by customary —OH and —NH protective groups known in the literature, such as, for example, the triflate group, the trimethylsilyl group or acyl groups, and also furthermore in the form of the methyl ethers and as phosphate esters, Furthermore very particular preference is given to oligosaccharides having up to 50 monomer units, where these may also be present in the form of aldoses, ketoses and/or lactoses, and protected by customary —OH and —NH protective groups known in the literature, such as, for example, the triflate group, the trimethylsilyl group, and furthermore may be present in the form of the methyl ethers and as phosphate esters.

By way of example of the polyols according to the invention, mention may be made of sorbitol, inositol, mannitol, tetritols, pentitols, hexitols, threitol, erythritol, adonitol, arabitol, xylitol, dulcitol, erythrose, threose, arabinose, ribose, xylose, lyxose, glucose, galactose, mannose, allose, altrose, gulose, idose, talose, fructose, sorbose, psicose, tegatose, deoxyribose, glucosamine, galactosamine, rhamnose, digitoxose, thioiglucose, saccharose, lactose, trehalose, maltose, celloboise, melibiose, gestiobiose, rutinose, raffinose, and cellotriose. Furthermore, reference may be made to the relevant specialist literature, such as, for example, Beyer-Walter, Lehrbuch der organischen Chemie [Textbook of organic chemistry], S. Hirzel Verlag Stuttgart, 19th Edition, Section III, pp. 393 et seq.

Preferred polyhydroxy compounds are sorbitol, inositol, mannitol, threitol, erythreitol, erythrose, threose, arabinose, ribose, xylose, glucose, galactose, mannose, allose, fructose, sorbose, deoxyribose, glucosamine, galactosamine, sacchrose, lactose, trehalose, maltose and cellobiose. Particular preference is given to using glucose, galactose, mannose, fructose, deoxyribose, glucosamine, sucrose, lactose, maltose and cellobiose. However, very particular preference is given to the use of glucose, galactose, mannose, fructose, sucrose, lactose, maltose or cellobiose.

The teaching according to the invention encompasses all isomeric forms, such as cis and trans isomers, diastereomers, epimers, anomers and thiral isomers.

According to the invention, it is also possible to use a mixture of two or more active ingredients (C).

The active ingredients (C) according to the invention are present in the agents in concentrations of from 0.01% by weight to 20% by weight, preferably from 0.05% by weight to 15% by weight and very particularly preferably in amounts of from 0.1% by weight to 10% by weight.

In a particularly preferred embodiment, at least one polyhydroxy compound with at least 2OH groups is present as active ingredient b). Among these compounds, preference is given to those with 2 to 12OH groups and in particular those with 2, 3, 4, 5, 6 or 10OH groups.

Polyhydroxy compounds with 2OH groups are, for example, glycol ($CH_2(OH)CH_2OH$) and other 1,2-diols, such as H—$(CH_2)_n$CH(OH)$CH_2$OH where n=1, 2, 3, 4, 5, 6, 7, 8, 9, 10, 11, 12, 13, 14, 15, 16, 17, 18, 19, 20. 1,3-Diols such as H—$(CH_2)_n$—CH(OH)$CH_2CH_2$OH where n=1, 2, 3, 4, 5, 6, 7, 8, 9, 10, 11, 12, 13, 14, 15, 16, 17, 18, 19, 20 can also be used according to the invention. The (n,n+1)- and (n,n+2)-diols with nonterminal OH groups can likewise be used.

Important representatives of polyhydroxy compounds with 2OH groups are also the polyethylene glycols and polypropylene glycols.

Among the polyhydroxy compounds with 3OH groups, glycerol has prominent significance.

In summary, preference is given to agents according to the invention in which the polyhydroxy compound is selected from ethylene glycol, propylene glycol, polyethylene glycol, polypropylene glycol, glycerol, glucose, fructose, pentaerythritol, sorbitol, mannitol, xylitol and their mixtures.

Irrespective of the type of polyhydroxy compound having at least 2OH groups used, preference is given to agents according to the invention which, based on the weight of the agent, comprise 0.01 to 5% by weight, preferably 0.05 to 4% by weight, particularly preferably 0.05 to 3.5% by weight and in particular 0.1 to 2.5% by weight, of polyhydroxy compound(s).

With particular preference, the agents according to the invention can additionally comprise polyethylene glycol ether of the formula (IV)

$$H(CH_2)_k(OCH_2CH_2)_nOH \qquad (IV)$$

in which k is a number between 1 and 18, particularly preferably the values 0,10, 12,16 and 18, and n is a number between 2 and 20, particularly preferably the values 2, 4, 5, 6, 7, 8, 9, 10, 12 and 14. Among these, preference is given to the alkyl derivatives of diethylene glycol, of triethylene glycol, of tetraethylene glycol, of pentaethylene glycol, of hexaethylene glycol, of heptaethylene glycol, of octaethylene glycol, of nonaethylene glycol, of decaethylene glycol, of dodecaethylene glycol and of tetradecaethylene glycol, and also the alkyl derivatives of dipropylene glycol, of tripropylene glycol, of tetrapropylene glycol, of pentapropylene glycol, of hexapropylene glycol, of hepta propylene glycol, of octapropylene glycol, of nonapropylene glycol, of decapropylene glycol, of dodecapropylene glycol and of tetradecapropylene glycol, where, among these, the methyl, ethyl, propyl, n-butyl, n-pentyl, n-hexyl, n-heptyl, n-octyl, n-nonyl, n-decyl, n-undecyl, n-dodecyl and n-tetradecyl derivatives are preferred.

It has been found that mixtures of "short-chain" polyalkylene glycol ethers with such "long-chain" polyalkylene glycol ethers have advantages. In this connection, "short-chain and long-chain" refers to the degree of polymerization of the polyalkylene glycol. Particular preference is given to mixtures of polyalkylene glycol ethers with a degree of oligomerization of 5 or less with polyalkylene glycol ethers with a degree of oligomerization of 7 or more. Preference is given to mixtures of alkyl derivatives of diethylene glycol, of triethylene glycol, of tetraethylene glycol, of pentaethylene glycol, of dipropylene glycol, of tripropylene glycol, of tetrapropylene glycol or of pentapropylene glycol with alkyl derivatives of hexaethylene glycol, of heptaethylene glycol, of octaethylene glycol, of nonaethylene glycol, of decaethylene glycol, of dodecaethylene glycol, of hexapropylene glycol, of heptapropylene glycol, of octapropylene glycol, of nonapropylene glycol, of decapropylene glycol, of dodecapropylene glycol or of tetradecapropylene glycol, where in both cases the n-octyl, n-decyl, n-dodecyl and n-tetradecyl derivatives are preferred.

Particularly preferred agents according to the invention are characterized in that it comprises at least one polyalkylene glycol ether (IV a) of the formula (IV) in which n is the numbers 2, 3, 4 or 5 and at least one polyalkylene glycol ether (IV b) of the formula (IV) in which n is the numbers 10, 12, 14 or 16, where the weight ratio (IV b) to (IV a) is 10:1 to 1:10, preferably 7.5:1 to 1:5 and in particular 5:1 to 1:1.

A very particularly diverse and interesting group of cosmetic active ingredients are polyhydroxy compounds. The use according to the invention of polyhydroxy compounds as active ingredient with the other components according to the invention can therefore be particularly preferred. For the purposes of the invention, polyhydroxy compounds are understood as meaning all substances which satisfy the definition in Römpp's Lexikon of Chemistry, Edition of 1999, Verlag Georg Thieme. According to this, polyhydroxy compounds are to be understood as meaning organic compounds with at least two hydroxy groups. For the purposes of the present invention, these are to be understood in particular as meaning:

polyols with at least two hydroxy groups, and with a carbon chain of from 2 to 30 carbon atoms, such as, for example, trimethylolpropane, ethoxylates and/or propoxylates having 1 to 50 mol of ethylene oxide and/or propylene oxide of the above-mentioned polyols, carbohydrates, sugar alcohols and sugars, and salts thereof, in particular monosaccharides, disaccharides, trisaccharides and oligosaccharides, where these may also be present in the form of aldoses, ketoses and/or lactoses, and protected by customary —OH and —NH protective groups known in the literature, such as, for example, the triflate group, the trimethylsilyl group or acyl groups, and also furthermore in the form of the methyl ethers and as phosphate esters, aminodeoxy sugars, deoxy sugars, thio sugars, where these may also be present in the form of aldoses, ketoses and/or lactoses, and protected by customary —OH and —NH protective groups known in the literature, such as, for example, the triflate group, the trimethylsilyl group or acyl groups, and also furthermore in the form of the methyl ethers and as phosphate esters, among these, preference is given to monosaccharides having 3 to 8 carbon atoms, such as, for example, trioses, tetroses, pentoses, hexoses, heptoses and octoses, where these may also be present in the form of aldoses, ketoses and/or lactoses, and protected by customary —OH and —NH protective groups known in the literature, such as, for example, the triflate group, the trimethylsilyl group or acyl groups, and also furthermore in the form of the methyl ethers and as phosphate esters.

Furthermore, preference is given to oligosaccharides having up to 50 monomer units, where these may also be present in the form of aldoses, ketoses and/or lactoses, and protected by customary —OH and —NH protective groups known in the literature, such as, for example, the triflate group, the trimethylsilyl group or acyl groups, and also furthermore in the form of the methyl ethers and as phosphate esters.

Very particularly preferred polyols of the present invention are polyols with 2 to 12 carbon atoms in the molecular backbone. These polyols may be straight-chain, branched, cyclic and/or unsaturated. The hydroxy groups here are very particularly preferably terminally adjacent or terminally separated from one another by the radical of the chain. Examples of these polyols are: glycol, polyethylene glycol up to a molecular weight up to 1,000 Daltons, neopentyl glycol, partial glycerol ethers with a molecular weight up to 1,000 Daltons, 1,2-propanediol, 1,3-propanediol, glycerol, 1,2-butanediol, 1,3-butanediol, 1,4-butanediol, 1,2,3-butanetriol, 1,2,4-butanetriol, pentanediols, for example, 1,2-pentanediol, 1,5-pentanediol, hexanediols, 1,2-hexanediol, 1,6-hexanediol, 1,2,6-hexanetriol, 1,4-cyclohexanediol, 1,2-cyclohexanediol, heptanediols, 1,2-heptanediol, 1,7-heptanediol, octanediols, 1,2-octanediol, 1,8-octanediol, 2-ethyl-1,3-hexanediol, octanedienols, decadienols, dodecanediols, 1,2-dodecanediol, 1,12-dodecanediol, 1,12-dodecanediol with 10 mol of EO, dodecadienols.

Furthermore, examples of the polyols according to the invention that may be mentioned are sorbitol, inositol, mannitol, tetritols, pentitols, hexitols, threitol, erythritol, adonitol, arabitol, xylitol, dulcitol, erythrose, threose, arabinose, ribose, xylose, lyxose, glucose, galactose, mannose, allose, altrose, gulose, idose, talose, fructose, sorbose, psicose, tegatose, deoxyribose, glucosamine, galactosamine, rhamnose, digitoxose, thioglucose, saccharose, lactose, trehalose, maltose, cellobiose, melibiose, gestiobiose, rutinose, raffinose and cellotriose. Furthermore, mention may be made to the relevant specialist literature, such as, for example, Beyer-Walter, Lehrbuch der organischen Chemie [Textbook of organic chemistry], S. Hirzel Verlag Stuttgart, 19th Edition, Section III, pp. 393 et seq.

The teaching according to the invention encompasses all isomeric forms, such as cis and transisomers, diastereomers, epimers, anomers and chiral isomers.

According to the invention, it is also possible to use a mixture of two or more polyols (B).

The polyols (B) according to the invention are present in the agents in concentrations of from 0.01% by weight to 20% by weight, preferably from 0.05% by weight to 15% by weight and very particularly preferably in amounts of from 0.1% by weight to 10% by weight.

Furthermore, the classes of substances listed in annex 6, section A and B of the Cosmetics Ordinance are used. Particular preference is given to mild preservation. The following substances and mixtures thereof are used for this purpose:

aromatic alcohols, such as, for example, phenoxyethanol, benzyl alcohol, phenethyl alcohol, phenoxyisopropanol, parabens, for example methylparaben, ethylparaben, propylparaben, butylparaben, isobutylparaben 1,2-alkanediols having 5 to 22 carbon atoms in the carbon chain, such as, for example, 1,2-pentanediol, 1,2-hexanediol, 1,2-heptanediol, 1,2-decanediol, 1,2-dodecanediol, 1,2-hexadecanediol, organic acids and physiologically compatible salts thereof, such as, for example, citric acid, lactic acid, acetic acid, benzoic acid, sorbic acid, salicylic acid, dehydroacetic acid.

Further optional ingredients which can be used in cosmetic compositions together with the active ingredient complex (A) according to the invention are preservatives. Suitable preservatives are, for example:

- aromatic alcohols, such as, for example, phenoxyethanol, benzyl alcohol, phenethyl alcohol, phenoxyisopropanol,
- aldehydes, such as, for example, formaldehyde solution and paraformaldehyde, glutaraldehyde
- parabens, for example methylparaben, ethylparaben, propylparaben, butylparaben, isobutylparaben
- 1,2-alkanediols having 5 to 22 carbon atoms in the carbon chain, such as, for example, 1,2-pentanediol, 1,2-hexanediol, 1,2-heptanediol, 1,2-decanediol, 1,2-dodecanediol, 1,2-hexadecanediol,
- compounds that cleave off formaldehyde, such as, for example, DMDM hydantoin, diazolidinylurea
- halogenated compounds, such as, for example, isothiazolinones, such as, for example, methylchloroisothiazolinone/methylisothiazolinones, triclosan, triclocarban, iodopropynyl butylcarbamate, 5-bromo-5-nitro-1,3-dioxane, chlorhexidine digluconate and chlorhexidine acetate, 2-bromo-2-nitropropane-1,3-diol, methyldibromoglutaronitrile,
- inorganic compounds, such as, for example, sulfites, boric acid and borates, bisulfites,
- cationic substances, such as, for example, Quaterium-15, benzylakonium chloride, benzethonium chloride, polyaminopropylbiguanide,
- organic acids and physiologically compatible salts thereof, such as, for example, citric acid, lactic acid, acetic acid, benzoic acid, sorbic acid, salicylic acid, dehydroacetic acid
- active ingredients with additional effects such as, for example, zinc pyrithione, piroctone olamine,
- antioxidants, such as, for example, BHT (butylated hydroxytoluene), BHA (butylated hydroxyanisole), propyl gallate, t-butylhydroquinone,
- complexing agents, such as, for example, EDTA and derivatives thereof, HEDTA and derivatives thereof, etidronic acid and salts thereof,
- and mixtures of the substances listed above.

In a further particularly preferred type of the composition according to the invention, the water activity in the compositions according to the invention can also be reduced to the extent that growth of microorganisms can no longer take place. For this, glycerol and sorbin in particular are used.

The active ingredient complex (A) according to the invention in the compositions according to the invention contributes to the preservation being possible in an excellent manner using the mild preservative additives. However, the complete omission of preservatives is also possible and preferred according to the invention.

The amounts of preservatives are from 0 to 5% by weight, preferably from 0-2% by weight, particularly preferably from 0-1% by weight and very particularly preferably from 0-0.8% by weight, based on the total amount of the composition.

Further optional ingredients of the compositions according to the invention are deodorant active ingredients.

The active ingredient combination (A) according to the invention increases significantly, in an analytically detectable manner, the deposition of deodorant active ingredients on the skin. In the panel test, this is evident inter alia from a significantly longer-lasting effect.

Esterase inhibitors can be added as deodorant active ingredients. These are preferably trialkyl citrates, such as trimethyl citrate, tripropyl citrate, triisopropyl citrate, tributyl citrate and in particular triethyl citrate (Hydagen® CAT, COGNIS). The substances inhibit the enzyme activity and thereby reduce the formation of odor. It is likely here that cleavage of the citric acid ester results in the liberation of the free acid which lowers the pH on the skin to the extent that the enzymes are thereby inhibited. Further substances which are suitable as esterase inhibitors are dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate. Antibacterial active ingredients which influence the microbial flora and kill off sweat-decomposing bacteria, or inhibit their growth, may likewise be present in the stick preparations. Examples thereof are chitosan, phenoxyethanol and chlorhexidine gluconate. 5-Chloro-2-(2,4-dichlorophenoxy)phenol has also proven particularly effective; this is sold under the brand Irgasan® by Ciba-Geigy, Basel/CH.

Further very particularly preferred optional ingredients of the compositions which comprise the active ingredient combination (A) according to the invention are dye precursors. Dye precursors are oxidation dye precursors of the developer type (X1) and coupler type (X2), natural and synthetic direct dyes (Y) and precursors of nature-analogous dyes, such as indole and indoline derivatives, and mixtures of representatives of one or more of these groups.

Oxidation dye precursors of the developer type (X1) and coupler type (X2), natural and synthetic direct dyes (Y) and precursors of nature-analogous dyes, such as indole and indoline derivatives and mixtures of representatives of one or more of these groups can be used as such.

The oxidation dye precursors of the developer type (X1) used are usually primary aromatic amines with a further free or substituted hydroxy or amino group located in the para or ortho position, diaminopyridine derivatives, heterocyclic hydrazones, 4-aminopyrazole derivatives, and 2,4,5,6-tetraminopyrimidine and derivatives thereof. Suitable developer components are, for example, p-phenylenediamine, p-tolylenediamine, p-aminophenol, o-aminophenol, 1-(2'-hydroxyethyl)-2,5-diaminobenzene, N,N-bis(2-hydroxyethyl)-p-phenylenediamine, 2-(2,5-diaminophenoxy)ethanol, 4-amino-3-methylphenol, 2,4,5,6-tetraminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxymethylamino-4-aminophenol, bis(4-aminophenyl)amine, 4-amino-3-fluorophenol, 2-aminomethyl-4-aminophenol, 2-hydroxymethyl-4-aminophenol, 4-amino-2-((diethylamino)methyl)phenol, bis(2-hydroxy-5-aminophenyl)methane, 1,4-bis(4-amino-phenyl)diazacycloheptane, 1,3-bis(N (2-hydroxyethyl)-N-(4-aminophenylamino))-2-propanol, 4-amino-2-(2-hydroxyethoxy)phenol, 1,10-bis(2,5-diaminophenyl)-1,4,7,10-tetraoxadecane, and 4,5-diaminopyrazole derivatives as in EP 0 740 741 and WO 94/08970, such as, for example, 4,5-diamino-1-(2'-hydroxyethyl)pyrazole. Particularly advantageous developer components are p-phenylenediamine, p-tolylenediamine, p-aminophenol, 1-(2'-hydroxyethyl)-2,5-diaminobenzene, 4-amino-3-methylphenol, 2-aminomethyl-4-aminophenol, 2,4,5,6-tetraminopyrimidine, 2-hydroxy-4,5,6-triaminopyrimidine, 4-hydroxy-2,5,6-triaminopyrimidine.

The oxidation dye precursors of the coupler type (X2) used are generally m-phenylenediamine derivatives, naphthols, resorcinol and resorcinol derivatives, pyrazolones and m-aminophenol derivatives. Examples of such coupler components are m-aminophenol and derivatives thereof, such as, for example, 5-amino-2-methylphenol, 5-(3-hydroxypropylamino)-2-methylphenol, 3-amino-2-chloro-6-methylphenol, 2-hydroxy-4-aminophenoxyethanol, 2,6-di-methyl-3-aminophenol, 3-trifluoroacetylamino-2-chloro-6-methylphenol, 5-amino-4-chloro-2-methylphenol, 5-amino-4-methoxy-2-methlphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-(ethylamino)-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2-hydroxyethylamino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methyl-benzene, di- and trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, methylenedioxybenzene derivatives, such as, for example, 1-hydroxy-3,4-methylenedioxybenzene, 1-amino-3,4-methylenedioxybenzene and 1-(2'-hydroxyethyl)amino-3,4-methylenedioxybenzene.

Particularly suitable coupler components are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

Direct dyes are usually nitrophenylenediamines, nitroaminophenols, azo dyes, anthraquinones or indophenols. Particularly suitable direct dyes are the compounds known under the International names or trade names HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17, and also 1,4-bis(β-hydroxyethyl)amino-2-nitrobenzene, 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene.

Naturally occurring direct dyes are, for example, henna red, henna neutral, camomile blossom, sandalwood, black tea, buckthorn bark, sage, logwood, madder root, catechu, sedre and alkanna root.

It is not required that the oxidation dye precursors or the direct dyes are each single compounds. Rather, further components may also be present in the hair colorants according to the invention, as a result of the preparation method for the individual dyes, in secondary amounts provided these do not adversely affect the coloring result or have to be excluded for other reasons, e.g., toxicological reasons.

The precursors of nature-analogous dyes used are, for example, indoles and indolines, and physiologically compatible salts thereof. Preference is given to using those indoles and indolines which have at least one hydroxy or amino group, preferably as substituent on the six-membered ring. These groups can carry further substituents, e.g., in the form of an etherification or esterification of the hydroxy group or an alkylation of the amino group. 5,6-Dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxyindoline, 6-aminoindoline and 4-aminoindoline, and 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole have particularly advantageous properties.

Within this group, particular emphasis is to be placed on N-methyl-5,6-dihydroxyindoline, N-ethyl-5,6-dihydroxyindoline, N-propyl-5,6-dihydroxyindoline, N-butyl-5,6-dihydroxyindoline and in particular 5,6-dihydroxyindoline, and also N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline and indole derivatives in the colorants used within the scope of the method according to the invention can be used either as free bases or else in the form of their physiologically compatible salts with inorganic or organic acids, e.g., the hydrochlorides, the sulfates and hydrobromides.

When using dye precursors of the indoline or indole type, it may be preferred to use these together with at least one amino acid and/or at least one oligopeptide. Preferred amino acids are aminocarboxylic acids, in particular α-aminocarboxylic acids and ω-aminocarboxylic acids. Among the α-aminocarboxylic acids, arginine, lysine, ornithine and histidine are in turn particularly preferred. A very particularly preferred amino acid is arginine, in particular in free form, but also used as hydrochloride.

Both the oxidation dye precursors and also the direct dyes and the precursors of nature-analogous dyes are present in the agents according to the invention preferably in amounts of from 0.01 to 20% by weight, preferably 0.1 to 5% by weight, in each case based on the total agent.

The advantage which is achieved by the active ingredient combination (A) according to the invention in conjunction with the dye precursors is a significantly improved deposition of the dye precursors on the hair. In addition to increased deposition on the hair, the active ingredient complex according to the invention also brings about more rapid penetration into the hair. Furthermore, the desired hair color develops more quickly. The application time of the composition can be shortened by at least 10% for the same color result. Shortening the application time is possible with the combination according to the invention up to 40% with the same color result. All of these effects are achieved with a simultaneously increased wash resistance of the developed hair color. The invention encompasses the teaching that, on account of the achieved effects, on the other hand the concentration of dyes can also be significantly reduced. This is of great importance on the one hand in relation to costs, but on the other hand this also means a considerable improvement in the dermatological compatibility of the overall composition.

The very particularly preferred composition of the invention therefore relates to cosmetic compositions for coloring skin and hair, comprising the active ingredient complex (A) according to the invention and the dye precursor, and also the use of this agent and a method for coloring hair using this agent.

Hair colorants, particularly if the coloration takes place oxidatively, whether with atmospheric oxygen or other oxidizing agents such as hydrogen peroxide, are usually rendered weakly acidic to alkaline, i.e. to pH values in the range from about 5 to 11. For this purpose, the colorants comprise alkalizing agents, usually alkali metal or alkaline earth metal hydroxides, ammonia or organic amines. Preferred alkalizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine, and also alkali metal and alkaline earth metal hydroxides. In particular, monoethanolamine, triethanolamine, and 2-amino-2-methylpropanol and 2-amino-2-methyl-1,3-propanediol are preferred within this group. The use of ω-amino acids, such as ω-aminocaproic acid, as alkalizing agent is also possible.

If the development of the actual hair colors takes place in the course of an oxidative process, then customary oxidizing agents, such as, in particular, hydrogen peroxide or its addition products onto urea, melamine or sodium borate can be used. However, oxidation with atmospheric oxygen as the sole oxidizing agent may be preferred. Furthermore, it is possible to carry out the oxidation with the help of enzymes, the enzyme being used both for generating oxidizing percompounds, and also for boosting the effect of a small amount of oxidizing agent present, or else enzymes are used which transfer electrons from suitable developer components (reducing agents) to atmospheric oxygen. Preference is given here to oxidases such as tyrosinase, ascorbate oxidase and laccase, but also glucose oxidase, uricase or pyruvate oxidase. Furthermore, mention may be made of the procedure to enhance the effect of small amounts (e.g., 1% and less, based on the total agent) of hydrogen peroxide through peroxidases.

The preparation of the oxidizing agent is then expediently mixed with the dye precursors directly prior to coloring the hair with the preparation. The resulting ready-to-use hair coloring preparation should preferably have a pH in the range from 6 to 10. Application of the hair colorants in a weakly alkaline medium is particularly preferred. The application temperatures can be in a range between 15 and 40° C., preferably at the temperature of the scalp. After a contact time of about 5 to 45 minutes, in particular 15 to 30 minutes, the hair colorant is removed from the hair to be colored by rinsing. After washing with a shampoo is dispensed with if a carrier with a high content of surfactant, e.g., a coloring shampoo, has been used.

Particularly in the case of hair that is difficult to color, the preparation containing the dye precursors can be applied to the hair without prior mixing with the oxidation component. After a contact time of from 20 to 30 minutes and optionally after an interim rinse, the oxidation component is then applied. After a further contact time of from 10 to 20 minutes, the hair is then rinsed and, if desired, after shampooed. In this embodiment, according to a first variant in which the prior application of the dye precursors should bring about better penetration into the hair, the corresponding agent is adjusted to a pH of from about 4 to 7. According to a second variant, an air oxidation is firstly aimed for, where the applied agent preferably has a pH of from 7 to 10. During the subsequent accelerated post oxidation, the use of acidically rendered peroxidisulfate solutions as oxidizing agent may be preferred.

Furthermore, the development of the coloration can be supported and increased by adding certain metal ions to the agent. Such metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Of particular suitability here are $Zn^{2+}$, $Cu^{2+}$ and $Mn^{2+}$. The metal ions can in principle be used in the form of any desired physiologically compatible salt. Preferred salts are the acetates, sulfates, halides, lactates and tartrates. Through use of these metal salts it is possible both to accelerate the development of the coloration and also to influence the color nuance in a targeted manner.

In a further embodiment of the teaching according to the invention, it may be preferred to incorporate the active ingredient complex (A) directly into the colorant or tint, i.e. to use the active ingredient complex (A) according to the invention in combination with dyes and/or dye precursors.

Additionally, it may prove advantageous and the synergistic effects of the active ingredient combination (A) according to the invention yet further increase when penetration auxiliaries and/or swelling agents (M) are present. These substances can bring about better penetration of active ingredients into the skin to be treated or the hair to be treated. In this regard, examples include urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol and propylene glycol ethers, for example propylene glycol monoethyl ether, carbonates, hydrogencarbonates, diols and triols, and in particular 1,2-diols and 1,3-diols, such as, for example, 1,2-propanediol, 1,2-pentanediol, 1,2-hexanediol, 1,2-dodecanediol, 1,3-propanediol, 1,6-hexanediol, 1,5-pentanediol, 1,4-butanediol.

Dyes that can be used for coloring the compositions are the substances approved and suitable for cosmetic purposes, as listed, for example, in the publication "Cosmetic colorants" of the Dyes Commission of the German Research Society, Verlag Chemie, Weinheim, 1984, pp. 81-106. These dyes are usually used in concentrations of 0.001 to 0.1% by weight, based on the total mixture.

The pH of the preparations according to the invention can in principle be at values of 2-11. Depending on the purpose and the use of the composition according to the invention, the pH is selected and adjusted in a very targeted manner. For colorants, it is, for example, preferably between 5 and 11, with values from 6 to 10 being particularly preferred. For cleaning compositions, it is, for example, between 4 and 7.5, preferably between 4 and 6.

To establish this pH, virtually any acid or base can be used for cosmetic purposes. Preferred bases are ammonia, alkali metal hydroxides, monoethanolamine, triethanolamine and N,N,N',N-tetrakis(2-hydroxypropyl)ethylenediamine.

Usually, food acids are used as acids. Food acids are understood as meaning those acids which are consumed in the course of customary food consumption and have positive effects on the human organism. Food acids are, for example, acetic acid, lactic acid, tartaric acid, citric acid, malic acid, ascorbic acid and gluconic acid. For the purposes of the invention, the use of citric acid and lactic acid is particularly preferred.

It has furthermore been found that the effect of the active ingredient according to the invention in the agents according to the invention can be further increased in combination with substances which comprise primary or secondary amino groups. Examples of such amino compounds that may be mentioned are ammonia, monoethanolamine, 2-amino-2-methyl-1-propanol, 2-amino-2-methylpropanediol, and basic amino acids such as, for example, lysine, arginine or histidine. These amines can also be used in the form of the corresponding salts with inorganic and/or organic acids, such as, for example, as ammonium carbonate, ammonium citrate, ammonium oxalate, ammonium tartrate or lysine hydrochloride. The amines are used together with the active ingredient according to the invention in ratios of 1:10 to 10:1, preferably 3:1 to 1:3 and very particularly preferably in stoichiometric amounts.

Protic solvents, such as, for example, water, and alcohols may also be present in the compositions according to the invention. The alcohols used are all alcohols that can be used without physiological issues, for example methanol, ethanol, isopropanol, propanol, butanol, isobutanol, glycol, glycerol and mixtures thereof with one another. The proportion of protic solvents makes up the composition according to the invention in each case to 100 parts by weight. Preferably, at least 30% by weight of protic solvents, particularly preferably at least 50% by weight and very particularly preferably at least 75% by weight and most preferably at least 85% by weight, of protic solvents are present in the compositions according to the invention.

If the compositions according to the invention are solid compositions, such as soaps, syndets, combibars or shaped bodies, however, the fraction of protic solvents should remain below 10% by weight of the solid mass. Preferably, about 2-10% by weight of protic solvents are present in the solid masses.

With regard to further optional components and the amounts of these components used, reference is expressly made to the relevant handbooks known to the person skilled in the art, e.g., the aforementioned Monograph by K. H. Schrader and also cosmetic ingredients for the multiphase soaps according to the invention are known per se (Soaps and Detergents, Luis Spitz, ISBN 0-935315-71-2 and Production of Toilet Soap, D. Osteroth, ISBN 3-921956-55-2).

Besides the active ingredient complex (A) obligatorily required according to the invention and the further aforementioned preferred components, these preparations can in principle comprise all further components known to the person skilled in the art for such cosmetic agents.

Further active ingredients, auxiliaries and additives are, for example,
- thickeners, such as agar agar, guar gum, alginates, xanthan gum, gum Arabic, karaya gum, carob seed flour, linseed gums, dextrans, cellulose derivatives, e.g., methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol,
- hair-conditioning compounds, such as phospholipids, for example soy lecithin, egg lecithin and cephalins,
- dimethyl isosorbide and cyclodextrins,
- symmetrical and asymmetrical, linear and branched dialkyl ethers having in total between 12 and 36 carbon atoms, in particular 12 and 24 carbon atoms, such as, for example, di-n-octyl ether, di-n-decyl ether, di-n-nonyl ether, di-n-undecyl ether and di-n-dodecyl ether, n-hexyl n-octyl ether, n-octyl n-decyl ether, n-decyl n-undecyl ether, n-undecyl n-dodecyl ether and n-hexyl n-undecyl ether, and di-tert-butyl ether, diisopentyl ether, di-3-ethyldecyl ether, tert-butyl n-octyl ether, isopentyl n-octyl ether and 2-methylpentyl n-octyl ether,
- active ingredients that improve fiber structure, in particular mono-, di- and oligosaccharides, such as, for example, glucose, galactose, fructose, fruit sugar and lactose,
- phospholipids, for example soy lecithin, egg lecithin and cephalins,
- quaternized amines, such as methyl-1-alkylamidoethyl-2-alkylimidazolinium methosulfate,
- antidandruff active ingredients such as piroctone olamine, zinc omadine and climbazole,
- active ingredients such as allantoin and bisabolol,
- cholesterol,
- complexing agents, such as EDTA, NTA, β-alaninediacetic acid, iminodisuccinic acid and salts thereof, etidronic acid and salts thereof and phosphonic acids,
- swelling and penetration substances, such as primary, secondary and tertiary phosphates,
- opacifiers, such as latex, styrene/PVP and styrene-acrylamide copolymers
- pearlizing agents, such as ethylene glycol mono- and distearate, and PEG-3 distearate,
- pigments,
- reducing agents such as, for example, thioglycolic acid and derivatives thereof, thiolactic acid, cysteamine, thiomalic acid and α-mercaptoethanesulfonic acid,
- antioxidants.

As regards further optional components and the amounts of these components used, reference is expressly made to the relevant handbooks known to the person skilled in the art, e.g., the aforementioned Monograph by K. H. Schrader.

With regard to the way according to which the active ingredient complex according to the invention is applied to the keratin fibers, in particular the human hair, there are in principle no restrictions.

Preparations remaining on the hair have proven to be effective and can therefore constitute preferred embodiments of the teaching according to the invention. According to the invention preparations remaining on the hair are understood as meaning those which are not rinsed out of the hair again in the course of treatment after a period of from a few seconds to one hour with the help of water or an aqueous solution. Instead, the preparations remain on the hair until the next hair wash, i.e. generally more than 12 hours.

According to further preferred embodiments, the agents according to the invention can, for example, be setting agents such as hair-setting compositions, setting foams, styling gels and blow-waving compositions.

The present invention further provides the use of a preparation according to the invention for the restructuring of keratin fibers, in particular human hair.

Alternatively, the preparation can also be applied to the skin and/or the hair and left there until the next skin or hair wash. The present invention therefore further provides a method of treating skin or hair in which a preparation according to the invention is applied to the skin and/or the hair and left there until the next wash.

Preferred methods of the last-mentioned type are characterized in that the next wash takes place longer than 24 hours after the application of the preparation according to the invention to the skin and/or the hair.

The invention claimed is:

1. An article comprising (1) a solid hair setting treatment composition comprising (a) at least 1.0% by weight of at least one film-forming and/or setting polymer, (b) at least 0.1% by weight of a dissolution accelerator; and (2) a mill or grater for grating the hair setting treatment composition and dispensing the composition as a granule or a powder.

2. The article of claim 1 wherein the composition is ground to a powder or granulated prior to dispensation from the article.

3. The article of claim 1 wherein the film-forming and/or setting polymer is selected from the group consisting of Acrylates/t-Butylacrylamide Copolymer, Octylacrylamide/Acrylates/Butylaminoethyl Methacrylate Copolymer, Polyurethane-1, Polyvinylcaprolactam, VP/VA Copolymer and mixtures thereof.

4. The article of claim 1 wherein the dissolution accelerator is a gas-evolving component.

5. The article of claim 4 wherein the gas-evolving component is a composition comprising mono-, di- or tribasic acids having a $pK_a$ value of from 1.0 to 6.9 and alkali metal silicates, carbonates, hydrogen carbonates, and/or mixtures thereof.

6. The article of claim 5 wherein the acids are homopolymers of acrylic acid or copolymers of acrylic acid and maleic acid.

7. The article of claim 4 wherein the dissolution accelerator is a gas which is a gas incorporated into the hair setting treatment composition.

8. The article of claim 7 wherein the gas is selected from the group consisting of air, carbon dioxide, $N_2O$, and oxygen.

9. The article of claim 1 wherein the article is in the form of a brush.

10. The article of claim 1 wherein the composition is in the form of a granule or a powder.

11. The article of claim 1 wherein the composition is dispensed as an aerosol.

12. The article of claim 1 wherein the composition is in the form of a solid block body.

* * * * *